US007910566B2

(12) United States Patent
Feinstein

(10) Patent No.: US 7,910,566 B2
(45) Date of Patent: Mar. 22, 2011

(54) PREVENTION AND TREATMENT OF ACUTE RENAL FAILURE AND OTHER KIDNEY DISEASES BY INHIBITION OF P53 BY SIRNA

(75) Inventor: Elena Feinstein, Rehovot (IL)

(73) Assignee: Quark Pharmaceuticals Inc., Fremont, CA (US)

( * ) Notice: Subject to any disclaimer, the term of this patent is extended or adjusted under 35 U.S.C. 154(b) by 0 days.

(21) Appl. No.: 12/006,722

(22) Filed: Jan. 4, 2008

(65) Prior Publication Data
US 2009/0105173 A1   Apr. 23, 2009

Related U.S. Application Data

(63) Continuation-in-part of application No. 11/655,610, filed on Jan. 18, 2007.

(60) Provisional application No. 60/781,037, filed on Mar. 9, 2006, provisional application No. 60/854,503, filed on Oct. 25, 2006.

(51) Int. Cl.
*A61K 48/00* (2006.01)
*C07H 21/02* (2006.01)
*C07H 21/04* (2006.01)

(52) U.S. Cl. ..................... 514/44; 536/23.1; 536/24.5

(58) Field of Classification Search .................. None
See application file for complete search history.

(56) References Cited

U.S. PATENT DOCUMENTS

| | | | |
|---|---|---|---|
| 4,497,817 A | 2/1985 | Murase et al. |
| 5,898,031 A | 4/1999 | Crooke |
| 6,107,094 A | 8/2000 | Crooke |
| 6,372,249 B1 | 4/2002 | Smith et al. |
| 6,506,559 B1 | 1/2003 | Fire et al. |
| 6,593,353 B1 | 7/2003 | Gudkov et al. |
| 6,982,277 B2 | 1/2006 | Gudkov et al. |
| 7,008,956 B2 | 3/2006 | Gudkov et al. |
| 7,012,087 B2 | 3/2006 | Gudkov et al. |
| 7,781,575 B2 | 8/2010 | Khvorova et al. |
| 2002/0019425 A1 | 2/2002 | Gudkov et al. |
| 2004/0014956 A1 | 1/2004 | Woolf et al. |
| 2004/0180351 A1 | 9/2004 | Giese et al. |
| 2004/0209832 A1 | 10/2004 | McSwiggen et al. |
| 2005/0080246 A1 | 4/2005 | Allerson et al. |
| 2005/0222224 A1 | 10/2005 | Gudkov et al. |
| 2006/0069056 A1 | 3/2006 | Feinstein et al. |
| 2006/0217329 A1 | 9/2006 | Feinstein |
| 2007/0031844 A1 | 2/2007 | Khvorova et al. |
| 2007/0185047 A1 | 8/2007 | Bhat et al. |
| 2008/0108583 A1 | 5/2008 | Feinstein et al. |
| 2008/0287382 A1 | 11/2008 | Feinstein et al. |
| 2009/0082291 A1 | 3/2009 | Feinstein et al. |
| 2010/0029746 A1 | 2/2010 | Feinstein et al. |

FOREIGN PATENT DOCUMENTS

| | | |
|---|---|---|
| EP | 0 430 334 A1 | 6/1991 |
| WO | WO 00/44895 | 8/2000 |
| WO | WO 01/36646 A1 | 5/2001 |
| WO | WO 01/75164 A2 | 10/2001 |
| WO | WO 02/44321 A2 | 6/2002 |
| WO | WO 02/55693 | 7/2002 |
| WO | WO 03/070918 A2 | 8/2003 |
| WO | WO 03/074654 A2 | 9/2003 |
| WO | WO 2004/015107 A2 | 2/2004 |
| WO | WO 2004/031237 A1 | 4/2004 |
| WO | WO 2004/045543 | 6/2004 |
| WO | WO 2006/035434 A2 | 4/2006 |

OTHER PUBLICATIONS

Amarzguioui et al. (2003), "Tolerance for mutations and chemical modifications in a siRNA," Nucleic Acids Research, 31(2): 589-595, 2003.
Barik, Sailen (2005). "Silence of the Transcripts; RNA Interference In Medicine," J. Mol. Med. 83:764-773.
Bartel, David P. et al. (2004). "MicroRNAs: Genomics Biogenesis, Mechanism, and Function," Cell, 116:281-297.
Bernstein, Emily et al. (2001). "Role For a Bidentate Ribonuclease in the Initiation Step of RNA Interference," Nature, 409:363-366.
Bertrand et al. (2002). "Comparison of antisense oligonucleotides and siRNAs in cell culture and in vivo," Biochemical and Biophysical Research Communications, 296:1000-1004.
Bitko, Vira et al. (2004). "Inhibition of Respiratory Viruses By Nasally Administered siRNA," Nature Medicine, 11(1):50-55.
Botchkarev, V.A., et al., (2000). "p53 Is Essential for Chemotherapy-induced Hair Loss," Cancer Res. 60:5002-5006.
Brummelkamp, Thijn R. et al. (2002). "A System For Stable Expression of Short Interfering RNAs in Mammalian Cells," Science, 296: 550-553.
Caplen, Natasha J. et al. (2001). "Specific Inhibition of Gene Expression By Small Double-Stranded RNAs in Invertebrate Vertebrate Systems," PNAS, 98(17):9742-9747.
Chakraborty, Chiranjib (2007). "Potentiality of Small Interfering RNAs (siRNA) as Recent Therapeutic Targets for Gene-Silencing," Current Drug Targets, 8:469-482.
Chalk, Alistair M. et al., (2004). "Improved and Automated Prediction of Effective siRNA," Biochemical and Biophysical Research Communications, 319:264-274.
Chernov, M.V. and Stark, G.R., (1997). "The p53 activation and apoptosis induced by DNA damage are reversibly inhibited by salicylate," Oncogene 14:2503-2510.
Cotsarelis, G. and Millar, S.E., (2001). "Towards a molecular understanding of hair loss and its treatment," Trends Mol. Med. 7(7):293-301.

(Continued)

*Primary Examiner* — Amy Bowman
(74) *Attorney, Agent, or Firm* — John P. White; Cooper & Dunham LLP

(57) ABSTRACT

The invention relates to a double-stranded compound, preferably an oligoribonucleotide, which down-regulates the expression of a human p53 gene. The invention also relates to a pharmaceutical composition comprising the compound, or a vector capable of expressing the oligoribonucleotide compound, and a pharmaceutically acceptable carrier. The present invention also contemplates a method of treating a patient suffering from acute renal failure or other kidney diseases comprising administering to the patient the pharmaceutical composition in a therapeutically effective dose so as to thereby treat the patient.

5 Claims, 8 Drawing Sheets

OTHER PUBLICATIONS

Czauderna F, Fechtner M, Dames S, Aygün H, Klippel A, Pronk GJ, Giese K, Kaufmann J. (2003). "Structural variations and stabilising modifications of synthetic siRNAs in mammalian cells," Nucleic Acids Res. 31(11):2705-16.

Elbashir, Sayda M. et al. (2001). "RNA Interference is Mediated by 21- and 22-nucleotide RNAs," Genes & Development, 15:188-200.

Elbashir, Sayda M. et al. (2001). "Duplexes of 21-nucleotide RNAs mediated RNA interference in cultured mammalian cells," Nature, 411:494-498.

Elbashir SM, Martinez J, Patkaniowska A, Lendeckel W, Tuschl T. (2001). "Functional anatomy of siRNAs for mediating efficient RNAi in Drosophila melanogaster embroyo lysate," EMBO J. 20(23):6877-88.

Fire, Andrew et al., (1998). "Potent and Specific Genetic Interference by Double-stranded RNA in Caenorhabditis elegans," Nature, 391:806-811.

Gottlieb, T.M., et al., (1996). "p53 in growth control and neoplasia," Biochim Biophys Acta 1287:77-102.

Holen et al., (2002). Positional effects of short interfering RNAs targeting the human coagulation trigger Tissue Factor, Nucleic Acids Research, 30(8):1757-1766.

Komarov, P.G., et al., (1999). "A Chemical Inhibitor of p53 That Protects Mice from the Side Effects of Cancer Therapy," Science 285:1733-1737.

Komarova, E.A., et al., (1997). 'Transgenic mice with p53-responsive lacZ: p53 activity varies dramatically during normal development and determines radiation and drug sensitivity in vivo, EMBO J. 16(6):1391-1400.

Lee, Youngtae et al., (2003). "The nuclear RNase III Drosha initiates microRNA processing," Nature, 425:415-419.

Levenkova, Natasha et al., (2004). "Gene specific siRNA selector," Bioinformatics, 20(3):430-432.

Mahato et al. (2005). "Modulation of gene expression by antisense and antigene oligodeoxynucleotides and small interfering RNA", Expert Opinion on Drug Delivery, 2(1):3-28.

McManus, Michael T. and Sharp, Phillip A., (2002). "Gene Silencing in Mammals by Small Interfering RNAs," Genetics, 3:737-747.

Prakash TP, Allerson CR, Dande P, Vickers TA, Sioufi N, Jarres R, Baker BF, Swayze EE, Griffey RH, Bhat B. (2005). "Positional effect of chemical modifications on short interference RNA activity in mammalian cells," J Med Chem. 48(13):4247-53.

Scherer et al. (2003). "Approaches for the sequence-specific knockdown of mRNA," Nat. Biotechnol., 21 (12):1457-1465.

Schomber et al. (2004). "Gene silencing by lentivirus-mediated delivery of siRNA in human CD34+ cells," Blood, 103(12):4511-4513.

Sioud, Moudly and Leirdal, Marianne, (2004). "Potential Design Rules and Enzymatic Synthesis of siRNAs," Methods in Molecular Biology, 252:457-468.

Steele, R.J.C., et al., (1998). "The p53 tumour suppressor gene," Br. J. Surg. 85:1460-1467.

Supavekin, S., et al., (2003). "Differential gene expression following early renal ischemia/reperfusion," Kidney Int. 63:1714-1724.

Tekippe, M., et al., (2003). "Expansion of hematopoietic stem cell phenotype and activity in Trp53-null mice," Exp. Hematol. 31:521-527.

Tolentino, Michael J. et al., (2004). "Intravitreal Injection of Vascular Endothelial Growth Factor Small Interfering RNA Inhibits Growth and Leakage in a Nonhuman Primate, Laser-induced Model of Choroidal Neovascularization," Retina, The Journal of Retinal and Vitreous Diseases, 24(1):132-138.

Ui-Tei, Kumiko et al., (2004). "Guidelines for the selection of highly effective siRNA sequences for mammalian and chick RNA interference," Nucleic Acids Research, 32(3):936-948.

Wang, J. et al., (2003). "A Peptide Inhibitor of c-Jun N-Terminal Kinase Protects against Both Aminoglycoside and Acoustic Trauma-Induced Auditory Hair Cell Death and Hearing Loss," The J. of Neuroscience, 23(24):8596-8607.

Wlodarski, P., et al., (1998). "Role of p53 in Hematopoietic Recovery After Cytotoxic Treatment9," Blood 91(8):2998-3006.

Zhang, M. et al., (2003). "Pifithrin-$\alpha$ Supresses p53 and Protects Cochlear and Vestibular Hair Cells From Cisplatin-Induced Apoptosis," Neuroscience, 120:191-205.

Zhang et al. (2004). "Targeted Gene Silencing by Small Interfering RNA-Based Knock-Down Technology", Current Pharmaceutical Biotechnology, vol. 5:1-7.

Office Action issued on Mar. 23, 2001 in connection with U.S. Appl. No. 09/493,527, filed Jan. 28, 2000.

Office Action issued on Jul. 2, 2001 in connection with U.S. Appl. No. 09/493,527, filed Jan. 28, 2000.

Office Action issued on Dec. 28, 2001 in connection with U.S. Appl. No. 09/947,757, filed Sep. 6, 2001.

Office Action issued on Jun. 6, 2002 in connection with U.S. Appl. No. 09/493,527, filed Jan. 28, 2000.

Office Action issued on Feb. 12, 2003 in connection with U.S. Appl. No. 09/880,417, filed Jun. 13, 2001.

Office Action issued on Mar. 26, 2003 in connection with U.S. Appl. No. 09/947,757, filed Sep. 6, 2001.

Office Action issued on Jul. 15, 2003 in connection with U.S. Appl. No. 09/947,757, filed Sep. 6, 2001.

Office Action issued on Oct. 9, 2003 in connection with U.S. Appl. No. 09/880,417, filed Jun. 13, 2001.

Office Action issued on Nov. 19, 2003 in connection with U.S. Appl. No. 09/947,757, filed Sep. 6, 2001.

Office Action issued on Apr. 6, 2004 in connection with U.S. Appl. No. 10/350,560, filed Jan. 24, 2003.

Office Action issued on Jul. 9, 2004 in connection with U.S. Appl. No. 09/880,417, filed Jun. 13, 2001.

Office Action issued on Jul. 13, 2004 in connection with U.S. Appl. No. 09/947,757, filed Sep. 6, 2001.

Office Action issued on Nov. 26, 2004 in connection with U.S. Appl. No. 09/947,757, filed Sep. 6, 2001.

Office Action issued on Sep. 9, 2004 in connection with U.S. Appl. No. 10/352,597, filed Jan. 28, 2003.

Office Action issued on Jan. 3, 2005 in connection with U.S. Appl. No. 10/350,560, filed Jan. 24, 2003.

Office Action issued on Apr. 21, 2005 in connection with U.S. Appl. No. 10/352,597, filed Jan. 28, 2003.

Office Action issued on Oct. 30, 2007 in connection with U.S. Appl. No. 11/136,231, filed May 24, 2005.

Office Action issued on Nov. 9, 2006 in connection with U.S. Appl. No. 11/237,598, filed Sep. 27, 2005.

Response to Office Action issued on Nov. 9, 2006 in connection with U.S. Appl. No. 11/237,598, filed Dec. 8, 2006.

Office Action issued on Mar. 14, 2007 in connection with U.S. Appl. No. 11/237,598, filed Sep. 27, 2005.

Response to Office Action issued on Mar. 14, 2007 in connection with U.S. Appl. No. 11/237,598, filed Sep. 14, 2007.

Office Action issued on Dec. 3, 2007 in connection with U.S. Appl. No. 11/237,598, filed Sep. 27, 2005.

Advisory Action issued on Jun. 2, 2008 in connection with U.S. Appl. No. 11/237,598, filed Sep. 27, 2005.

Office Action issued on Oct. 28, 2008 in connection with U.S. Appl. No. 11/237,598, filed Sep. 27, 2005.

Office Action issued on Aug. 19, 2009 in connection with U.S. Appl. No. 11/237,598, filed Sep. 27, 2005.

Notice of Allowance issued on Nov. 18, 2009 in connection with U.S. Appl. No. 11/237,598, filed Sep. 27, 2005.

Communication under Rule 112 EPC issued by the European Patent Office on Dec. 16, 2003 in connection with European Patent Application No. 00914455.1.

Communication pursuant to Article 96(2) EPC issued by the European Patent Office on Feb. 12, 2004 in connection with European Patent Application No. 00914455.1.

Communication pursuant to Article 96(2) EPC issued by the European Patent Office on Aug. 19, 2004 in connection with European Patent Application No. 00914455.1.

Communication pursuant to Article 96(2) EPC issued by the European Patent Office on May 13, 2005 in connection with European Patent Application No. 00914455.1.

Result of consultation issued by the European Patent Office on Oct. 25, 2005 in connection with European Patent Application No. 00914455.1.

Communication pursuant to Article 96(2) EPC issued by the European Patent Office on Mar. 10, 2006 in connection with European Patent Application No. 00914455.1.

Communication pursuant to Article 96(2) EPC issued by the European Patent Office on Oct. 24, 2006 in connection with European Patent Application No. 00914455.1.

International Search Report issued by the International Searching Authority (ISA/US) on Dec. 3, 2007 in connection with International Application No. PCT/IL05/01035.

International Preliminary Report on Patentability issued by the International Searching Authority (ISA/US) on Apr. 2, 2009 in connection with International Application No. PCT/IL05/01035.

Written Opinion of the International Searching Authority (ISA/US) issued on Dec. 3, 2007 in connection with International Application No. PCT/IL05/01035.

Non-final Office Action issued on May 1, 2008 in connection with U.S. Appl. No. 11/655,610, filed Jan. 18, 2007.

Non-final Office Action issued on Oct. 2, 2008 in connection with U.S. Appl. No. 11/655,610, filed Jan. 18, 2007.

Notice of Allowance mailed on Apr. 7, 2009 in connection with U.S. Appl. No. 11/655,610, filed Jan. 18, 2007.

Non-final Office Action issued on Oct. 28, 2008 in connection with U.S. Appl. No. 11/237,598, filed Sep. 27, 2005.

Second Written Opinion issued by the Australian Patent Office on May 26, 2009 in connection with Singaporean Application No. 0702035-7.

Examination Report issued by the Australian Patent Office on Dec. 22, 2008 in connection with New Zealand Patent Application No. 553987.

Office Action issued by the Russian Patent Office on Jul. 20, 2009 in connection with Russian Patent Application No. 2007116168.

Final Office Action issued on Aug. 19, 2009 in connection with U.S. Appl. No. 11/237,598, filed Sep. 27, 2005.

Search Report issued by the Australian Patent Office on May 14, 2008 in connection with Singaporean Application/Patent No. 0702035-7.

Written Opinion issued by the Australian patent Office on May 14, 2008 in connection with Singaporean Application/Patent No. 0702035-7.

Pending claims in Elena Feinstein, et al., U.S. Appl. No. 11/827,199, filed Jul. 10, 2007.

Pending claims in Elena Feinstein et al., U.S. Appl. No. 12/008,578, filed Jan. 11, 2008.

Pending claims in U.S. Appl. No. 12/459,617, filed Jul. 1, 2009.

Molitoris et al (2009). "siRNA Targeted to p53 Attenuates Ischemic and Cisplatin-Induced Acute Kidney Injury". J. Am. Soc. Nephrol, published online May 21, 2009.

Cheng, Qing-Li et al. (2000), "Effects of ICAM-1 antisense oligonucleotide on the tubulointerstitium in mice with unilateral ureteral obstruction," Kidney International, vol. 57: 183-190.

Van de Water, Femke M. et al. (2006). "Intravenously administered short interfering RNA accumulates in the Kidney and selectively suppresses gene function in renal proximal tubules," Drug Metabolism and Disposition. 34:1393-1397.

Notice of Allowance mailed on Nov. 18, 2009 in connection with Elena Feinstein et al., U.S. Appl. No. 11/237,598, filed Sep. 27, 2005 and allowed claims.

Request for Continued Examination filed on Mar. 11, 2010, in connection with Elena Feinstein et al., U.S. Appl. No. 11/237,598, filed Sep. 27, 2005.

Non-final Official Action issued on May 10, 2010, in connection with Elena Feinstein et al., U.S. Appl. No. 11/237,598, filed Sep. 27, 2005.

Notice of Allowance mailed on Jul. 22, 2010 in connection with Elena Feinstein et al., U.S. Appl. No. 11/827,199, filed Jul. 10, 2007 and allowed claims.

Preliminary amendment to the claims filed on Sep. 10, 2010 in connection with Elena Feinstein et al., U.S. Appl. No. 12/008,578, filed Jan. 11, 2008.

Amendment after notice of allowance filed on Sep. 22, 2010 in connection with Elena Feinstein et al., U.S. Appl. No. 11/655,610, filed Jan. 18, 2007.

Non-final Official Action issued on May 27, 2010, in connection with Elena Feinstein et al., U.S. Appl. No. 12/459,617, filed Jul. 1, 2009.

Non-final Official Action issued on Oct. 4, 2010, in connection with Elena Feinstein et al., U.S. Appl. No. 12/008,578, filed Jan. 11, 2008.

Figure 1

Homo sapiens tumor protein p53 (Li-Fraumeni syndrome) (TP53), mRNA
gi|8400737|ref|NM_000546.2

| | | | | | | | |
|---|---|---|---|---|---|---|---|
| Hum-TP53 | 1 | ACTTGTCATG | GCGACTGTCC | AGCTTTGTGC | CAGGAGCCTC | GCAGGGGTTG ATGGGATTGG GGTTTTCCCC | 70 |
| Hum-TP53 | 71 | TCCCATGTGC | TCAAGACTGG | CGCTAAAAGT | TTTGAGCTTC | TCAAAAGTCT AGAGCCACCG TCCAGGGAGC | 140 |
| Hum-TP53 | 141 | AGGTAGCTGC | TGGGCTCCGG | GGACACTTTG | CGTTCGGGCT | GGGAGCGTGC TTTCCACGAC GGTGACACGC | 210 |
| Hum-TP53 | 211 | TTCCCTGGAT | TGGCAGCCAG | ACTGCCTTCC | GGGTCACTGC | CATGGAGGAG CCGCAGTCAG ATCCTAGCGT | 280 |
| Hum-TP53 | 281 | CGAGCCCCCT | CTGAGTCAGG | AAACATTTTC | AGACCTATGG | AAACTACTTC CTGAAAACAA CGTTCTGTCC | 350 |
| Hum-TP53 | 351 | CCCTTGCCGT | CCCAAGCAAT | GGATGATTTG | ATGCTGTCCC | CGGACGATAT TGAACAATGG TTCACTGAAG | 420 |
| Hum-TP53 | 421 | ACCCAGGTCC | AGATGAAGCT | CCCAGAATGC | CAGAGGCTGC | TCCCCGCGTG GCCCCTGCAC CAGCAGCTCC | 490 |
| Hum-TP53 | 491 | TACACCGGCG | GCCCCTGCAC | CAGCCCCCTC | CTGGCCCCTG | TCATCTTCTG TCCCTTCCCA GAAAACCTAC | 560 |
| Hum-TP53 | 561 | CAGGGCAGCT | ACGGTTTCCG | TCTGGGCTTC | TTGCATTCTG | GGACAGCCAA GTCTGTGACT TGCACGTACT | 630 |
| Hum-TP53 | 631 | CCCCTGCCCT | CAACAAGATG | TTTTGCCAAC | TGGCCAAGAC | CTGCCCTGTG CAGCTGTGGG TTGATTCCAC | 700 |
| Hum-TP53 | 701 | ACCCCCGCCC | GGCACCCGCG | TCCGCGCCAT | GGCCATCTAC | AAGCAGTCAC AGCACATGAC GGAGGTTGTG | 770 |
| Hum-TP53 | 771 | AGGCGCTGCC | CCCACCATGA | GCGCTGCTCA | GATAGCGATG | GTCTGGCCCC TCCTCAGCAT CTTATCCGAG | 840 |
| Hum-TP53 | 841 | TGGAAGGAAA | TTTGCGTGTG | GAGTATTTGG | ATGACAGAAA | CACTTTTCGA CATAGTGTGG TGGTGCCCTA | 910 |
| Hum-TP53 | 911 | TGAGCCGCCT | GAGGTTGGCT | CTGACTGTAC | CACCATCCAC | TACAACTACA TGTGTAACAG TTCCTGCATG | 980 |
| Hum-TP53 | 981 | GGCGGCATGA | ACCGGAGGCC | CATCCTCACC | ATCATCACAC | TGGAAGACTC CAGTGGTAAT CTACTGGGAC | 1050 |
| Hum-TP53 | 1051 | GGAACAGCTT | TGAGGTGCGT | GTTTGTGCCT | GTCCTGGGAG | AGACCGGCGC ACAGAGGAAG AGAATCTCCG | 1120 |
| Hum-TP53 | 1121 | CAAGAAAGGG | GAGCCTCACC | ACGAGCTGCC | CCCAGGGAGC | ACTAAGCGAG CACTGCCCAA CAACACCAGC | 1190 |
| Hum-TP53 | 1191 | TCCTCTCCCC | AGCCAAAGAA | GAAACCACTG | GATGGAGAAT | ATTTCACCCT TCAGATCCGT GGGCGTGAGC | 1260 |
| Hum-TP53 | 1261 | GCTTCGAGAT | GTTCCGAGAG | CTGAATGAGG | CCTTGGAACT | CAAGGATGCC CAGGCTGGGA AGGAGCCAGG | 1330 |
| Hum-TP53 | 1331 | GGGGAGCAGG | GCTCACTCCA | GCCACCTGAA | GTCCAAAAAG | GGTCAGTCTA CCTCCCGCCA TAAAAAACTC | 1400 |
| Hum-TP53 | 1401 | ATGTTCAAGA | CAGAAGGGCC | TGACTCAGAC | TGACATTCTC | CACTTCTTGT TCCCCACTGA CAGCCTCCCA | 1470 |
| Hum-TP53 | 1471 | CCCCCATCTC | TCCCTCCCCT | GCCATTTTGG | GTTTTGGGTC | TTTGAACCCT TGCTTGCAAT AGGTGTGCGT | 1540 |
| Hum-TP53 | 1541 | CAGAAGCACC | CAGGACTTCC | ATTTGCTTTG | TCCCGGGGCT | CCACTGAACA AGTTGGCCTG CACTGGTGTT | 1610 |
| Hum-TP53 | 1611 | TTGTTGTGGG | GAGGAGGATG | GGGAGTAGGA | CATACCAGCT | TAGATTTTAA GGTTTTTACT GTGAGGGATG | 1680 |
| Hum-TP53 | 1681 | TTTGGGAGAT | GTAAGAAATG | TTCTTGCAGT | TAAGGGTTAG | TTTACAATCA GCCACATTCT AGGTAGGTAG | 1750 |
| Hum-TP53 | 1751 | GGGCCCACTT | CACCGTACTA | ACCAGGGAAG | CTGTCCCTCA | TGTTGAATTT TCTCTAACTT CAAGGCCCAT | 1820 |
| Hum-TP53 | 1821 | ATCTGTGAAA | TGCTGGCATT | TGCACCTACC | TCACAGAGTG | CATTGTGAGG GTTAATGAAA TAATGTACAT | 1890 |
| Hum-TP53 | 1891 | CTGGCCTTGA | AACCACCTTT | TATTACATGG | GGTCTAAAAC | TTGACCCCCT TGAGGGTGCC TGTTCCCTCT | 1960 |
| Hum-TP53 | 1961 | CCCTCTCCCT | GTTGGCTGGT | GGGTTGGTAG | TTTCTACAGT | TGGGCAGCTG GTTAGGTAGA GGGAGTTGTC | 2030 |

Figure 1 (CONTINUED)

```
Hum-TP53  2031 AAGTCTTGCT GGCCCAGCCA AACCCTGTCT GACAACCTCT TGGTCGACCT TAGTACCTAA AAGGAAATCT 2100

Hum-TP53  2101 CACCCCATCC CACACCCTGG AGGATTTCAT CTCTTGTATA TGATGATCTG GATCCACCAA GACTTGTTTT 2170

Hum-TP53  2171 ATGCTCAGGG TCAATTTCTT TTTTCTTTTT TTTTTTTTTT TTTCTTTTTC TTTGAGACTG GGTCTCGCTT 2240

Hum-TP53  2241 TGTTGCCCAG GCTGGAGTGG AGTGGCGTGA TCTTGGCTTA CTGCAGCCTT TGCCTCCCCG GCTCGAGCAG 2310

Hum-TP53  2311 TCCTGCCTCA GCCTCCGGAG TAGCTGGGAC CACAGGTTCA TGCCACCATG GCCAGCCAAC TTTTGCATGT 2380

Hum-TP53  2381 TTTGTAGAGA TGGGGTCTCA CAGTGTTGCC CAGGCTGGTC TCAAACTCCT GGGCTCAGGC GATCCACCTG 2450

Hum-TP53  2451 TCTCAGCCTC CCAGAGTGCT GGGATTACAA TTGTGAGCCA CCACGTGGAG CTGGAAGGGT CAACATCTTT 2520

Hum-TP53  2521 TACATTCTGC AAGCACATCT GCATTTTCAC CCCACCCTTC CCCTCCTTCT CCCTTTTTAT ATCCCATTTT 2590

Hum-TP53  2591 TATATCGATC TCTTATTTTA CAATAAAACT TTGCTGCCA 2629
```

Note that the start (ATG) and stop (TGA) codons are underlined

Figure 2

```
Protein - Homo sapiens tumor protein p53 (Li-Fraumeni syndrome) (TP53)

Hum_TP53_prot    1   MEEPQSDPSV EPPLSQETFS DLWKLLPENN VLSPLPSQAM DDLMLSPDDI EQWFTEDPGP DEAPRMPEAA Hum_TP53_prot   71   PRVAPAPAAP TPAAPAPAPS WPLSSSVPSQ KTYQGSYGFR LGFLHSGTAK SVTCTYSPAL NKMFCQLAKT Hum_TP53_prot  141   CPVQLWVDST PPPGTRVRAM AIYKQSQHMT EVVRRCPHHE RCSDSDGLAP PQHLIRVEGN LRVEYLDDRN Hum_TP53_prot  211   TFRHSVVVPY EPPEVGSDCT TIHYNYMCNS SCMGGMNRRP ILTIITLEDS SGNLLGRNSF EVRVCACPGR Hum_TP53_prot  281   DRRTEEENLR KKGEPHHELP PGSTKRALPN NTSSSPQPKK KPLDGEYFTL QIRGRERFEM FRELNEALEL Hum_TP53_prot  351   KDAQAGKEPG GSRAHSSHLK SKKGQSTSRH KKLMFKTEGP DSD 393
```
Variations in other human entries in GeneBank(gi- 23491728; gi-35209; gi-13097806):
R72 -> P
R273 -> H
P278 -> A
P309 -> S

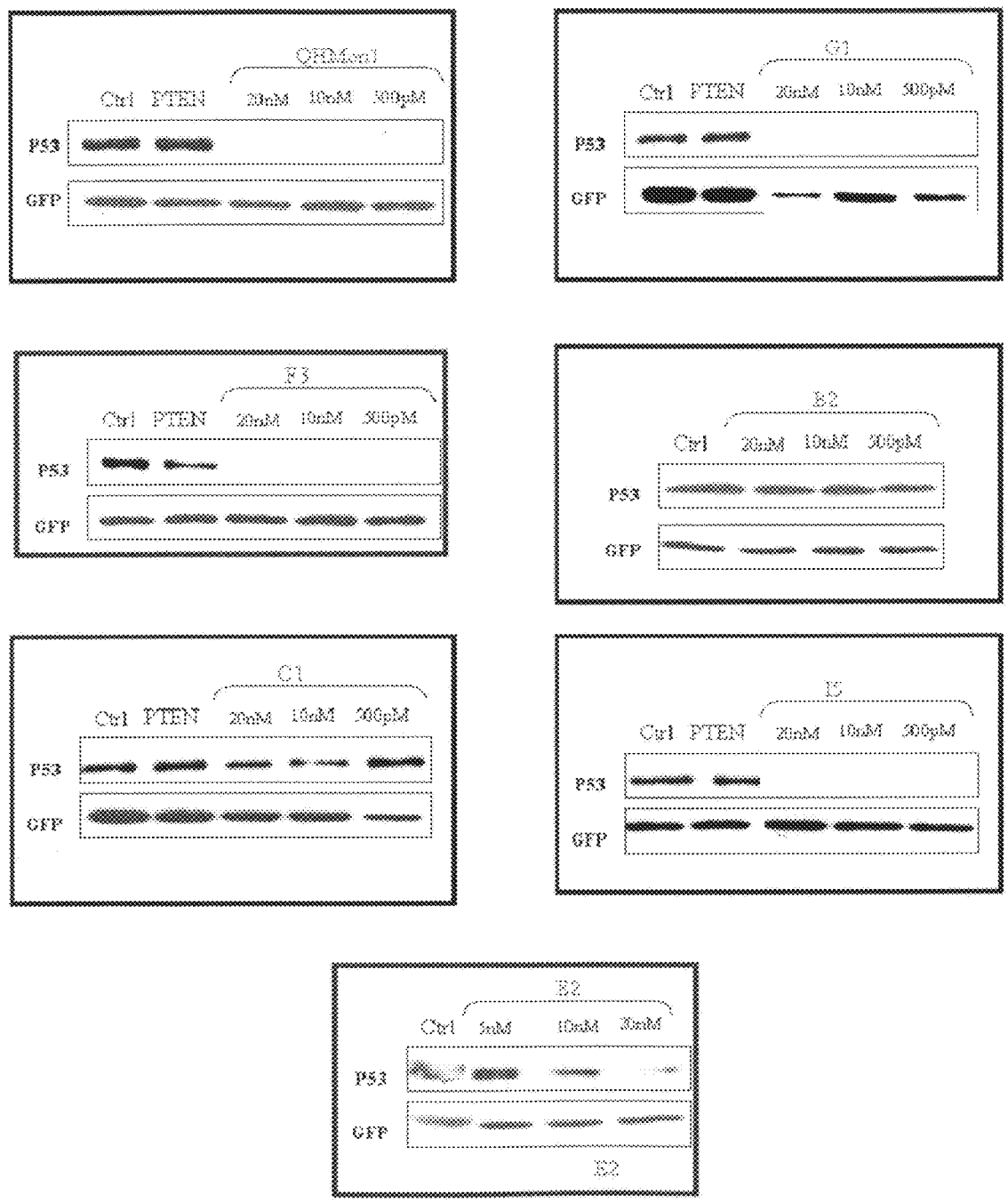

Figure 4
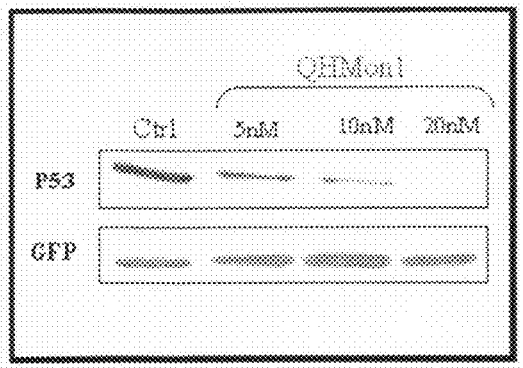
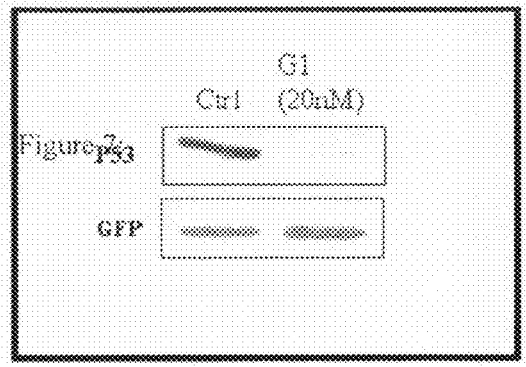
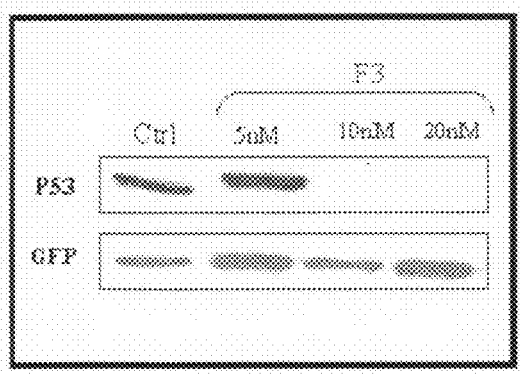
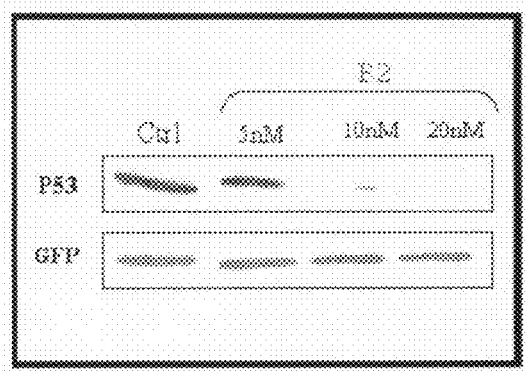
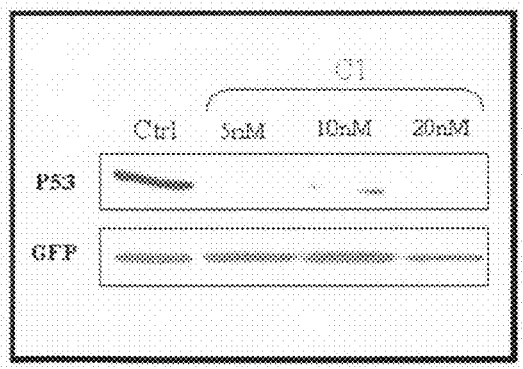
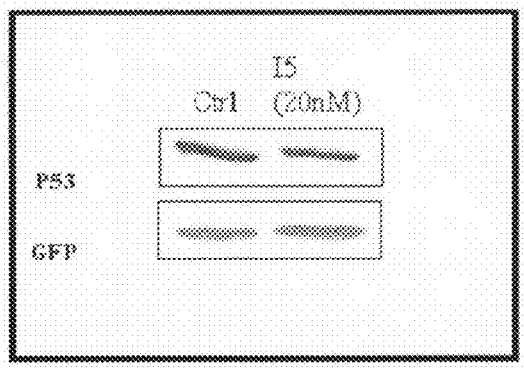
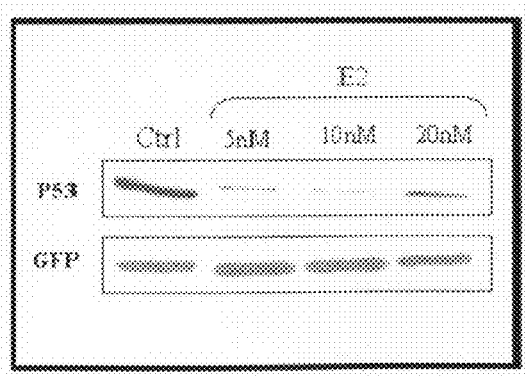

PREVENTION AND TREATMENT OF ACUTE RENAL FAILURE AND OTHER KIDNEY DISEASES BY INHIBITION OF P53 BY SIRNA

This application is a CIP of U.S. application Ser. No. 11/655,610 filed Jan. 18, 2007 and claims the benefit of U.S. Provisional Patent Application No. 60/781,037, filed Mar. 9, 2006 and of U.S. Provisional Patent Application No. 60/854,503, filed Oct. 25, 2006, all of which are hereby incorporated by reference in their entirety.

Throughout this application various patent and scientific publications are cited. The disclosures for these publications in their entireties are hereby incorporated by reference into this application to more fully describe the state of the art to which this invention pertains.

BACKGROUND OF THE INVENTION siRNAs and RNA Interference

RNA interference (RNAi) is a phenomenon involving double-stranded (ds) RNA-dependent gene specific posttranscriptional silencing. Originally, attempts to study this phenomenon and to manipulate mammalian cells experimentally were frustrated by an active, non-specific antiviral defence mechanism which was activated in response to long dsRNA molecules; see Gil et al. 2000, Apoptosis, 5:107-114. Later it was discovered that synthetic duplexes of 21 nucleotide RNAs could mediate gene specific RNAi in mammalian cells, without the stimulation of the generic antiviral defence mechanisms (see Elbashir et al. Nature 2001, 411:494-498 and Caplen et al. Proc Natl Acad Sci 2001, 98:9742-9747). As a result, small interfering RNAs (siRNAs), which are short double-stranded RNAs, have become powerful tools in attempting to understand gene function.

Thus, RNA interference (RNAi) refers to the process of sequence-specific post-transcriptional gene silencing in mammals mediated by small interfering RNAs (siRNAs) (Fire et al, 1998, Nature 391, 806) or microRNAs (miRNAs) (Ambros V. Nature 431:7006, 350-355(2004); and Bartel D P. Cell. 2004 Jan. 23; 116(2): 281-97 *MicroRNAs: genomics, biogenesis, mechanism, and function*). The corresponding process in plants is commonly referred to as specific post-transcriptional gene silencing or RNA silencing and is also referred to as quelling in fungi. An siRNA is a double-stranded RNA molecule which down-regulates or silences (prevents) the expression of a gene/mRNA of its endogenous counterpart. RNA interference is based on the ability of dsRNA species to enter a specific protein complex, where it is then targeted to the complementary cellular RNA and specifically degrades it. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al 2001, Genes Dev., 15, 188). In more detail, longer dsRNAs are digested into short (17-29 hp) dsRNA fragments (also referred to as short inhibitory RNAs—"siRNAs") by type III RNAses (DICER, DROSHA, etc., Bernstein et al., Nature, 2001, v. 409, p. 363-6; Lee et al., Nature, 2003, 425, p. 415-9). The RISC protein complex recognizes these fragments and complementary mRNA. The whole process is culminated by endonuclease cleavage of target mRNA (McManus&Sharp, Nature Rev Genet, 2002, v. 3, p. 737-47; Paddison &Hannon, Curr Opin Mol Ther. 2003 June; 5(3): 217-24). For information on these terms and proposed mechanisms, see Bernstein E., Denli A M. Hannon G J: 2001 *The rest is silence*. RNA. I; 7(11): 1509-21; Nishikura K.: 2001 *A short primer on RNAi: RNA-directed RNA polymerase acts as a key catalyst*. Cell. 116; 107(4): 415-8 and PCT publication WO 01/36646 (Glover et al).

The selection and synthesis of siRNA corresponding to known genes has been widely reported; see for example Chalk A M, Wahlestedt C, Sonnhammer E L. 2004 *Improved and automated prediction of effective siRNA* Biochem. Biophys. Res. Commun. June 18; 319(1): 264-74; Sioud M, Leirdal M., 2004, *Potential design rules and enzymatic synthesis of siRNAs*, Methods Mol Biol.; 252:457-69; Levenkova N, Gu Q, Rux J J. 2004, *Gene specific siRNA selector* Bioinformatics. 112; 20(3): 430-2. and Ui-Tei K, Naito Y, Takahashi F, Haraguchi T, Ohki-Hamazaki H, Juni A, Ueda R, Saigo K., *Guidelines for the selection of highly effective siRNA sequences for mammalian and chick RNA interference* Nucleic Acids Res. 2004 I 9; 32(3):936-48. Se also Liu Y, Braasch D A, Nulf C J, Corey D R. *Efficient and isoform-selective inhibition of cellular gene expression by peptide nucleic acids*, Biochemistry, 2004 I 24; 43(7):1921-7. See also PCT publications WO 2004/015107 (Atugen) and WO 02/44321 (Tuschl et al), and also Chiu Y L, Rana T M. *siRNA function in RNAi: a chemical modification analysis*, RNA 2003 September; 9(9):1034-48 and I Patent Nos. 5898031 and 6107094 (Crooke) for production of modified/more stable siRNAs.

Several groups have described the development of DNA-based vectors capable of generating siRNA within cells. The method generally involves transcription of short hairpin RNAs that are efficiently processed to form siRNAs within cells. Paddison et al. *PNAS* 2002, 99:1443-14'48; Paddison et al. *Genes & Dev* 2002, 16:948-958; Sui et al. *PNAS* 2002, 8:5515-5520; and Brummelkamp et al. *Science* 2002, 296: 550-553. These reports describe methods to generate siRNAs capable of specifically targeting numerous endogenously and exogenously expressed genes.

Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Bitko et al., "Inhibition of respiratory viruses by nasally administered siRNA", Nat. Med. 2005, 11(1):50-55). A review of the use of siRNA in medicine was recently published by Barik S. in J. Mol. Med. (2005) 83: 764-773). Furthermore, a phase I clinical study with short siRNA molecule that targets the VEGFR1 receptor for the treatment of Age-Related Macular Degeneration (AMD) has been conducted in human patients. The siRNA drug administered by an intravitreal inter-ocular injection was found effective and safe in 14 patients tested after a maximum of 157 days of follow up (Boston Globe Jan. 21, 2005).

The p53 Gene and Polypeptide

The human p53 gene is a well-known and highly studied gene. The p53 polypeptide plays a key role in cellular stress response mechanisms by converting a variety of different stimuli, for example DNA damaging conditions, such as gamma-irradiation, deregulation of transcription or replication, and oncogene transformation, into cell growth arrest or apoptosis (Gottlieb et al, 1996, Biochem. Biophys. Acta, 1287, p. 77). The p53 polypeptide is essential for the induction of programmed cell death or "apoptosis" as a response to such stimuli.

Most anti-cancer therapies damage or kill also normal cells that contain native p53, causing severe side effects associated with the damage or death of healthy cells. Since such side effects are to a great extent determined by p53-mediated death of normal cells, the temporary suppression of p53 during the acute phase of anti-cancer therapy has been suggested as a therapeutic strategy to avoid these severe toxic events. This was described in U.S. Pat. No. 6,593,353 and in Komarov P G et al, 1999, *A chemical inhibitor of p53 that protects mice from the side effects of cancer therapy*, Science, 285 (5434):1651, 1653, p53 has been shown to be involved in chemotherapy and radiation-induced alopecia. (Botcharev et al, 2000, *p53 is essential for Chemotherapy-induced Hair Loss*, Cancer Research, 60, 5002-5006).

Chemical-Induced Ototoxicity

The toxic effects of various ototoxic therapeutic drugs on auditory cells and spiral ganglion neurons are often the limiting factor for their therapeutic usefulness. Main ototoxic drugs include the widely used chemotherapeutic agent cisplatin and its analogs, commonly used aminoglycoside antibiotics, e.g. gentamicin, for the treatment of infections caused by gram-negative bacteria, quinine and its analogs, salicylate and its analogs, and loop-diuretics.

For example, antibacterial aminoglycosides such as gentamicins, streptomycins, kanamycins, tobramycins, and the like are known to have serious toxicity, particularly ototoxicity and nephrotoxicity, which reduces the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980)). Clearly, ototoxicity is a dose-limiting side-effect of antibiotic administration. From 4 to 15% of patients receiving 1 gram per day for greater than 1 week develop measurable hearing loss, which slowly becomes worse and can lead to complete permanent deafness if treatment continues.

Ototoxicity is also a serious dose-limiting side-effect for cisplatin, a platinum coordination complex, that has proven effective on a variety of human cancers including testicular, ovarian, bladder, and head and neck cancer. Cisplatin (Platinol®) damages auditory and vestibular systems. Salicylates, such as aspirin, are the most commonly used therapeutic drugs for their anti-inflammatory, analgesic, anti-pyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

Accordingly, there exists a need for means to prevent, reduce or treat the incidence and/or severity of inner ear disorders and hearing impairments involving inner ear tissue, particularly inner ear hair cells. Of particular interest are those conditions arising as an unwanted side-effect of ototoxic therapeutic drugs including cisplatin and its analogs, aminoglycoside antibiotics, salicylate and its analogs, or loop diuretics. In addition, there exits a need for methods which will allow higher and thus more effective dosing with these ototoxicity-inducing pharmaceutical drugs, while concomitantly preventing or reducing ototoxic effects caused by these drugs. What is needed is a method that provides a safe, effective, and prolonged means for prophylactic or curative treatment of hearing impairments related to inner ear tissue damage, loss, or degeneration, particularly ototoxin-induced and particularly involving inner ear hair cells.

Without being bound by theory, it is believed that cisplatin drugs and other drugs that induce ototoxicity (such as aminoglycoside antibiotics) may induce the ototoxic effects via programmed cell death or apoptosis in inner ear tissue, particularly inner ear hair cells (Zhang et al., Neuroscience 120 (2003) 191-205; Wang et al., J. Neuroscience 23((24):8596-8607). In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Acute Renal Failure (ARF).

ARF is a clinical syndrome characterized by rapid deterioration of renal function that occurs within days. Without being bound by theory acute kidney injury may be the result of renal ischemia-reperfusion injury (IRE) that occurs, for example, in patients undergoing major surgery such as major cardiac surgery.

The principal feature of ARF is an abrupt decline in glomerular filtration rate (GFR), resulting in the retention of nitrogenous wastes (urea, creatinine). In the general world population 170-200 cases of severe ARF per million population occur annually. To date, there is no specific treatment for ARF. Several drugs have been found to ameliorate toxic and ischemic experimental ARF, as manifested by lower serum creatinine levels, reduced histological damage and faster recovery of renal function in different animal models. These include anti-oxidants, calcium channel blockers, diuretics, vasoactive substances, growth factors, anti-inflammatory agents and more. However, those drugs that have been studied in clinical trials showed no benefit, and their use in ARF has not been approved.

In the majority of hospitalized patients, ARF is caused by acute tubular necrosis (ATN), which results from ischemic and/or nephrotoxic insults. Renal hypoperfusion is caused by hypovolemic, cardiogenic and septic shock, by administration of vasoconstrictive drugs or renovascular injury. Nephrotoxins include exogenous toxins such as contrast media and aminoglycosides as well as endogenous toxin such as myoglobin. Recent studies, however, indicate that apoptosis in renal tissue is prominent in most human cases of ARF, with the principal site of apoptotic cell death being the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al. Science. 1999, 285(5434): 1733-7); see also (Supavekin et al. Kidney Int. 2003. 63(5): 1714-24).

Hamar et al., administered siRNA targeting Fas, a mediator of apoptosis, to mice by hydrodynamic injection or via renal vein infusion (PNAS 2004. 102(41): 14883-14888).

Currently there are no satisfactory modes of therapy for the prevention and/or treatment of acute renal failure and related kidney diseases and disorders.

SUMMARY OF THE INVENTION

The present invention provides double stranded oligoribonucleotides that inhibit the p53 gene. The invention also provides a pharmaceutical composition comprising one or more such oligoribonucleotides, and a vector capable of expressing the oligoribonucleotide. The present invention also relates to methods and compositions for treating or preventing acute renal failure (ARF) following ischemic-reperfusion event, wherein the composition is administered in a therapeutically effective dose following the initiation of the ischemic-reperfusion event. The present invention also relates to methods and compositions for treating or preventing the incidence or severity of hearing impairment (or balance impairment), particularly hearing impairment associated with cell death of the inner ear hair cells or outer ear hair cells. The methods and compositions involve administering to a mammal in need of such treatment a prophylactically or therapeutically effective amount of one or more compounds which down-regulate expression of the p53 gene, particularly small interfering RNAs (siRNAs), small molecule inhibitors of p53 as described herein or antibodies to p53 polypeptide.

In one embodiment, the siRNA molecules disclosed herein may be used in the treatment of acute renal failure (ARF), which is characterized by rapid deterioration of renal function associated with apoptotic cell death in the renal tissue. In some embodiments kidney injury is ischemic-reperfusion injury resulting from major surgery. In various embodiments major surgery is cardiac surgery. In other embodiments surgery is transplant surgery. In certain preferred embodiments kidney injury is acute injury. In some embodiments kidney injury results from sepsis or chemical-induced nephrotoxicity.

According to one aspect the present invention provides a method of treating a patient suffering from a kidney injury following an ischemic-reperfusion event comprising administering to the patient a composition comprising one or more compounds having the structure:

5' $(N)_x$-Z 3' (antisense strand)
3' Z'-$(N')_y$ 5' (sense strand)

wherein each of N and N' is a ribonucleotide which may be modified or unmodified in its sugar residue;
wherein each of $(N)_x$ and $(N')_y$ is an oligomer in which each consecutive N or N' is joined to the next N or N' by a covalent bond;
wherein each of x and y is an integer between 18 and 40;
wherein each of Z and Z' may be present or absent, but if present is 1-5 consecutive nucleotides covalently attached at the 3' terminus of the strand in which it is present;
wherein the sequence of $(N')_y$ is present within a mRNA whose sequence is set forth in SEQ ID NO:1, and wherein the composition is administered in a therapeutically effective dose following the initiation of the ischemic-reperfusion event so as to thereby treat the patient.

In some embodiments each of $(N)_x$ and $(N')_y$ are selected from an oliogomer set forth in any one of SEQ ID NOS: 3-388.

In another aspect the present invention provides a compound having the structure:

5' $(N)_x$-Z 3' (antisense strand)
3' Z'-$(N')_y$ 5' (sense strand)

wherein each of N and N' is a nucleotide which may be modified or unmodified in its sugar residue;
wherein each of $(N)_x$ and $(N')_y$ is an oligonucleotide in which each consecutive N or N' is joined to the next N or N' by a covalent bond and wherein each of $(N)_x$ and $(N')_y$ are selected from SEQ ID NOS: 317-388;
wherein each of x and y is an integer between 18 and 40;
wherein each of Z and Z' may be present or absent, but if present is 1-5 consecutive nucleotides covalently attached at the 3' terminus of the strand in which it is present.

In some embodiments the covalent bond joining each consecutive N or N' is a phosphodiester bond. In various embodiments all the covalent bonds are phosphodiester bonds.

In some embodiments the sequence of $(N)_x$ and $(N')_y$ are fully complementary.

In some embodiments the compound is blunt ended, for example wherein both Z and Z' are absent. In an alternative embodiment, the compound comprises at least one 3' overhang, wherein at least one of Z or Z' is present. Z and Z' can independently comprise one or more covalently linked modified or non-modified nucleotides, for example inverted dT or dA; dT, LNA, mirror nucleotide and the like. In some embodiments each of Z and Z' are independently selected from dT and dTdT.

In some embodiments N or N' comprises a modification in the sugar residue of one or more ribonucleotides. In other embodiments the compound comprises at least one ribonucleotide modified in the sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification comprises a methoxy moiety. A presently preferred modification is a 2' methoxy of the sugar residue (2'-O-methyl; 2'-O-Me; 2'-O—$CH_3$).

In various embodiments the compound comprises an antisense sequence present in Tables A, B, C1 and C2 (SEQ ID NOS:3-316 and SEQ ID NOS:319-388). In other embodiments the present invention provides a mammalian expression vector comprising an antisense sequence present in Tables A, B, C1 and C2 (SEQ ID NOS:3-316 and SEQ ID NOS:319-388).

In another aspect the present invention provides a pharmaceutical composition comprising a novel compound of the invention; and a pharmacologiclaly acceptable carrier or excipient.

In yet another aspect the present invention provides a method for the treatment of a subject having acute renal failure (ARF) or related disease or disorder comprising the step of administering to the subject an amount of an siRNA which reduces or inhibits expression of p53 polypeptide (SEQ ID NO:2), wherein the composition is administered in a therapeutically effective dose following the initiation of the ischemic-reperfusion event so as to thereby treat the patient.

In another embodiment the present invention provides methods and compositions for treating a patient suffering from hearing impairment, or other oto-pathologies associated with cell death of inner ear hair cells or outer ear hair cells. Such oto-pathologies may be the result of acoustic trauma, mechanical trauma, or ototoxin-induced hearing loss. The methods of the invention comprising administering to the patient one or more compounds which down-regulate expression of the p53 gene, particularly siRNAs that inhibit p53, typically as a pharmaceutical composition, in a therapeutically effective dose so as to thereby treat the patient. Since long-term p53 inactivation may significantly increase the risk of cancer, it is preferred that the inhibition of p53 using the molecules of the present invention be temporary or local.

In one embodiment, the present invention provides for improved compositions and methods for treatments requiring administration of a pharmaceutical drug having an ototoxic, hearing-impairing side-effect, in combination with a therapeutically effective amount of one or more siRNA molecules that inhibit p53, to treat or prevent the ototoxicity induced by the pharmaceutical drug. The compositions of the invention can be administered at a suitable interval(s) either prior to, subsequent to, or substantially concurrently with the administration of the ototoxic, hearing-impairing drug that induces inner ear apoptotic tissue damage.

Accordingly, it is an object of the invention to provide an improved composition containing a therapeutically effective amount of one or more siRNA molecules that inhibit p53 in combination with an ototoxic, hearing-impairing pharmaceutical drug for administration to a mammal. Preferably, the combination drugs are administered separately; the siRNA molecules that inhibit p53 are administered locally while the ototoxic, hearing-impairing pharmaceutical drug is administered systemically. The siRNA molecules may be administered prior to, simultaneously with or subsequent to the ototoxic drug. Such combination compositions can further contain a pharmaceutically acceptable carrier. The pharmaceutical composition will have lower ototoxicity than the ototoxic pharmaceutical alone, and, preferably, will have a higher dosage of the ototoxic pharmaceutical than typically used. Examples of such improved compositions cisplatin or other ototoxic neoplastic agent or an aminoglycoside antibiotic(s) in combination with the therapeutically effective amount of one or more siRNA molecules that inhibit p53.

Still further, the invention relates to the use of the compositions of the invention in cases where diuretics are needed. The present invention provides a solution to the art that has long sought a therapy and a medicament which can treat the ototoxic effects currently associated with certain diuretics, and particular with the more popular and commonly used loop-diuretics, without sacrificing their diuretic effectiveness.

Still further, the invention relates to the use of the compositions of the invention in cases where quinine or quinine-like compounds are needed. The present invention provides a solution to the art that has long sought a therapy and a medicament which can treat the ototoxic effects currently associated with certain quinines without sacrificing their effectiveness.

Still further, the invention relates to a method for treating or preventing the incidence or severity of hearing impairment in a patient comprising administering to the patient a composition comprising an effective amount of naked siRNA molecules. Preferably, the naked siRNA molecules are applied directly to the round window membrane of the cochlea or administered by transtympanic injection. Further, the naked siRNA molecules are preferably directed against at least one pro-apoptotic gene.

BRIEF DESCRIPTION OF THE FIGURES

FIG. 1. This figure represents the nucleotide sequence of the human p53 gene—SEQ ID NO:1.

FIG. 2. This figure represents the amino acid sequence of the human p53 polypeptide—SEQ ID NO:2.

FIG. 3. This figure shows Western Blot results demonstrating the effect of various human p53 siRNAs on p53 expression.

FIG. 4. This figure shows Western Blot results demonstrating the various mouse p53 siRNAs on p53 expression.

DETAILED DESCRIPTION OF THE INVENTION

Figure 5:
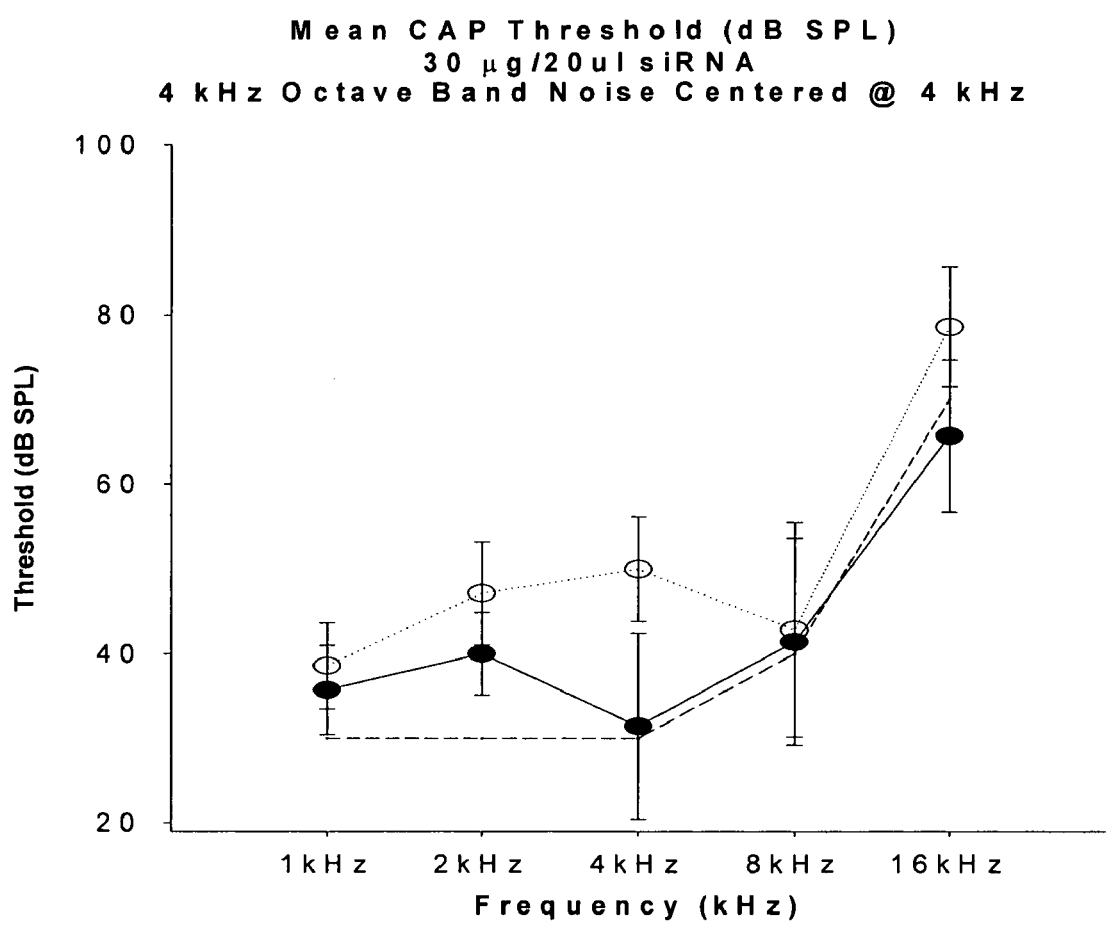
FIG. 5. This figure shows the effect of p53 siRNA treatment on acoustic-induced hair cell death in the cochlea of chinchilla.

The present invention relates generally to compounds which down-regulate expression of the p53 gene, particularly to novel small interfering RNAs (siRNAs), and to the use of these novel siRNAs in the treatment of various diseases and medical conditions in particular various forms of acute renal failure or hearing impairment as described above. Preferred lists of such siRNA are in Tables A, B, C1 and C2.

The inventors of the present invention have found that it is beneficial to induce temporary inhibition of p53 in order to treat any of the above diseases or disorders. Methods, molecules and compositions which inhibit p53 are discussed herein at length, and any of said molecules and/or compositions may be beneficially employed in the treatment of a patient suffering from any of said conditions.

The present invention provides methods and compositions for inhibiting expression of a target p53 gene in vivo. In general, the method includes administering oligoribonucleotides, such as small interfering RNAs siRNAs) that are targeted to a particular p53 gene mRNA and hybridize to, or interact with, the mRNAs under biological conditions (within the cell), or a nucleic acid material that can produce siRNA in a cell, in an amount sufficient to down-regulate expression of a target gene by an RNA interference mechanism. In particular, the subject method can be used to inhibit expression of the p53 gene for treatment of a disease.

In accordance with the present invention, the siRNA molecules or inhibitors of the p53 gene may be used as drugs to treat various pathologies accompanied by an elevated level of p53 polypeptide. Since long-term p53 inactivation can significantly increase the risk of cancer, it is preferred that the inhibition of p53 using the molecules of the present invention be temporary/reversible.

The present invention provides double-stranded oligoribonucleotides (siRNAs), which down-regulate the expression of the p53 gene. An siRNA of the invention is a duplex oligoribonucleotide in which the sense strand is derived from the mRNA sequence of the p53 gene, and the antisense strand is complementary to the sense strand. In general, some deviation from the target mRNA sequence is tolerated without compromising the siRNA activity (see e.g. Czaudcma et al 2003 Nucleic Acids Research 31(11), 2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

There are at least four variant p53 polypeptides (see Bourdon et al. *Genes Dev.* 2005; 19: 2122-2137). The sequence given in FIG. 1 is the nucleotide sequence of gi-8400737. The corresponding polypeptide sequence has 393 amino acids; see FIG. 2. All variants and any other similar minor variants are included in the definition of p53 polypeptide and in the definition of the p53 genes encoding them.

As used herein, the term "p53 gene" is defined as any homolog of the p53 gene having preferably 90% homology, more preferably 95% homology, and even more preferably 98% homology to the amino acid encoding region of SEQ ID NO:1 or nucleic acid sequences which bind to the p53 gene under conditions of highly stringent hybridization, which are well-known in the art (for example, see Ausubel et al., Current Protocols in Molecular Biology, John Wiley and Sons, Baltimore, Md. (1988), updated in 1995 and 1998.

As used herein, the term "p53", or "p53 polypeptide" is defined as any homolog of the p53 polypeptide having preferably 90% homology, more preferably 95% homology, and even more preferably 98% homology to SEQ ID NO:2, as either full-length or a fragment or a domain thereof, as a mutant or the polypeptide encoded by a spliced variant nucleic acid sequence, as a chimera with other polypeptides, provided that any of the above has the same or substantially the same biological function as the p53 polypeptide.

As used herein, an "inhibitor" is a compound which is capable of inhibiting or reducing the expression or activity of a gene or the product of such gene to an extent sufficient to achieve a desired biological or physiological effect. The term "inhibitor" as used herein refers to one or more of an oligonucleotide inhibitor, including siRNA, shRNA, aptamers, antisense molecules, miRNA and ribozymes, as well as antibodies.

As used herein, the term "Oligonucleotide" refers to a sequence having from about 2 to about 50 linked nucleotides or linked modified nucleotides, or a combination of modified and unmodified nucleotide. Oligonucleotide includes the terms oligomer, antisense strand and sense strand.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide.

Generally, the siRNAs used in the present invention comprise a ribonucleic acid comprising a double stranded structure, whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides and whereby said second stretch is at least partially identical to a target nucleic acid, whereby said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides. Further, said first strand and/or said second strand may comprise said plurality of modified nucleotides and may comprises said plurality of groups of modified nucleotides.

The group of modified nucleotides and/or the group of flanking nucleotides may comprise a number of nucleotides whereby the number is selected from the group comprising one nucleotide to 10 nucleotides. In connection with any ranges specified herein it is to be understood that each range discloses any individual integer between the respective figures used to define the range including said two figures defining said range. In the present case the group thus comprises one nucleotide, two nucleotides, three nucleotides, four nucleotides, five nucleotides, six nucleotides, seven nucleotides, eight nucleotides, nine nucleotides and ten nucleotides.

The groups of modified nucleotides and flanking nucleotides may be organized in a pattern on at least one of the strands. In some embodiments the first and second strands comprise a pattern of modified nucleotides. In various embodiments the pattern of modified nucleotides of said first strand is identical relative to the pattern of modified nucleotides of the second strand.

The pattern of modified nucleotides of said first strand may be shifted by one or more nucleotides relative to the pattern of modified nucleotides of the second strand.

In some preferred embodiments the middle ribonucleotide in the first strand (antisense) is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this.

The modifications discussed above may be selected from the group comprising amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 613 925 B1.

The double stranded structure of the siRNA may be blunt ended, on one or both sides. More specifically, the double stranded structure may be blunt ended on the double stranded structure's side which is defined by the 5'-end of the first strand and the 3'-end of the second strand, or the double stranded structure may be blunt ended on the double stranded structure's side which is defined by at the 3'-end of the first strand and the 5'-end of the second strand.

Additionally, at least one of the two strands may have an overhang of at least one nucleotide at the 5'-end; the overhang may consist of at least one deoxyribonucleotide. At least one of the strands may also optionally have an overhang of at least one nucleotide at the 3'-end.

The length of the double-stranded structure of the siRNA is typically from about 17 to 21 and more preferably 18 or 19 bases. Further, the length of said first strand and/or the length of said second strand may independently from each other be selected from the group comprising the ranges of from about 15 to about 23 bases, 17 to 21 bases and 18 or 19 bases. In another embodiment, the length of the double-stranded structure of the siRNA is typically from about 17 to 23 and more preferably 23 bases.

Additionally, the complementarily between said first strand and the target nucleic acid may be perfect, or the duplex formed between the first strand and the target nucleic acid may comprise at least 15 nucleotides wherein there is one mismatch or two mismatches between said first strand and the target nucleic acid forming said double-stranded structure.

For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

In some cases both the first strand and the second strand each comprise at least one group of modified nucleotides and at least one flanking group of nucleotides, whereby each group of modified nucleotides comprises at least one nucleotide and whereby each flanking group of nucleotides comprising at least one nucleotide with each group of modified nucleotides of the first strand being aligned with a flanking group of nucleotides on the second strand, whereby the most terminal 5' nucleotide of the first strand is a nucleotide of the group of modified nucleotides, and the most terminal 3' nucleotide of the second strand is a nucleotide of the flanking group of nucleotides. Each group of modified nucleotides may consist of a single nucleotide and/or each flanking group of nucleotides may consist of a single nucleotide.

Additionally, it is possible that on the first strand the nucleotide forming the flanking group of nucleotides is an unmodified nucleotide which is arranged in a 3' direction relative to the nucleotide forming the group of modified nucleotides, and on the second strand the nucleotide forming the group of modified nucleotides is a modified nucleotide which is arranged in 5' direction relative to the nucleotide forming the flanking group of nucleotides.

Further the first strand of the siRNA may comprise eight to twelve, preferably nine to eleven, groups of modified nucleotides, and the second strand may comprise seven to eleven, preferably eight to ten, groups of modified nucleotides.

The first strand and the second strand may be linked by a loop structure, which may be comprised of a non-nucleic acid polymer such as, inter alia, polyethylene glycol. Alternatively, the loop structure may be comprised of a nucleic acid.

Further, the 5'-terminus of the first strand of the siRNA may be linked to the 3'-terminus of the second strand, or the 3'-end of the first strand may be linked to the 5'-terminus of the second strand, said linkage being via a nucleic acid linker typically having a length between 10-2000 nucleobases.

In one aspect the present invention provides a compound having the structure:
5' $(N)_x$-Z 3' (antisense strand)
3' Z'-$(N')_y$ 5' (sense strand)
wherein each of N and N' is a nucleotide which may be modified or unmodified in its sugar residue;
wherein each of $(N)_x$ and $(N')_y$ is an oligonucleotide in which each consecutive N or N' is joined to the next N or N' by a covalent bond;
wherein each of x and y is an integer between 18 and 40;
wherein each of Z and Z' may be present or absent, but if present is 1-5 nucleotides covalently attached at the 3' terminus of the strand in which it is present; and
wherein the sequence of $(N)_x$ comprises an antisense sequence to mRNA of p53.

In some embodiments the compound comprises a phosphodiester bond. In various embodiments the compound comprises ribonucleotides wherein x=y and wherein x is an integer selected from the group consisting of 19, 20, 21, 22 or 23. In some embodiments x=y=19. In other embodiments x=y=23.

In some embodiments the compound is blunt ended, for example wherein Z and Z' are both absent. In an alternative embodiment, the compound comprises at least one 3' overhang, wherein at least one of Z or Z' is present. Z and Z' can be independently comprise one or more covalently linked modified or non-modified nucleotides, as described infra, for example inverted dT or dA; dT, LNA, mirror nucleotide and the like. In some embodiments each of Z and Z' are independently selected from dT and dTdT.

In some embodiments the compound comprises one or more ribonucleotides unmodified in their sugar residues. In other embodiments the compound comprises at least one ribonucleotide modified in the sugar residue. In some embodiments the compound comprises a modification at the 2' position of the sugar residue. Modifications in the 2' position of the sugar residue include amino, fluoro, methoxy, alkoxy and alkyl moieties. In certain preferred embodiments the modification comprises a ribonucleotide comprising a methoxy moiety at the 2' position (2'-O-methyl; 2'-O-Me; 2'-O—$CH_3$) of the sugar residue.

In some embodiments the compound comprises modified alternating ribonucleotides in one or both of the antisense and the sense strands. In preferred embodiments the compound comprises modified alternating ribonucleotides in the antisense and the sense strands. In some preferred embodiments the middle ribonucleotide of the antisense strand is not modified; e.g. ribonucleotide in position 10 in a 19-mer strand.

In additional embodiments the compound comprises modified ribonucleotides in alternating positions wherein the ribonucleotides at the 5' and 3' termini of the antisense strand are modified in their sugar residues, and the ribonucleotides at the 5' and 3' termini of the sense strand are unmodified in their sugar residues. In some embodiments, neither the antisense nor the sense strands are phosphorylated at the 3' and 5' termini. In other embodiments either or both the antisense and the sense strands are phosphorylated at the 3' termini.

In various embodiments the compound comprises an antisense sequence present in Tables A, B, C1 or C2. In other embodiments the present invention provides a mammalian expression vector comprising an antisense sequence present in Tables A, B, C1 or C2.

In certain embodiments the present invention provides a compound having the structure
5' (N) 3' antisense strand
3' (N') 5' sense strand
wherein each of N and N'=19 and are fully complementary;
wherein alternating ribonucleotides in the antisense and the sense strands are modified to result in a 2'-O-methyl modification in the sugar residue of the ribonucleotides;
wherein the ribonucleotides at the 5' and 3' termini of the antisense strand are modified;
wherein the ribonucleotides at the 5' and 3' termini of the sense strand are unmodified;
wherein the antisense and the sense strands are phosphorylated or non-phosphorylated at the 3' and 5' termini; and
wherein each of N and N' is selected from the group of oligomers set forth in Tables A or B.

In certain embodiments the present invention provides a compound having the structure
5' (N)x 3' antisense strand
3' (N')y 5' sense strand
wherein each of x and y=23 and $(N)_x$ and $(N')_y$ are fully complementary
wherein alternating ribonucleotides in $(N)_x$ and $(N')_y$ are modified to result in a 2'-O-methyl modification in the sugar residue of the ribonucleotides;
wherein each N at the 5' and 3' termini of $(N)_x$ are modified;
wherein each N' at the 5' and 3' termini of $(N')_y$ are unmodified;
wherein each of $(N)_x$ and $(N')_y$ is selected from the group of oligomers set forth in Table C2.

$(N)_x$ and $(N')_y$ may be phosphorylated or non-phosphorylated at the 3' and 5' termini. In certain embodiments of the invention, alternating ribonucleotides are modified in both the antisense and the sense strands of the compound. In particular the exemplified siRNA has been modified such that a 2'-O-methyl (2'-OMe) group was present on the first, third, fifth, seventh, ninth, eleventh, thirteenth, fifteenth, seventeenth, nineteenth, twenty-first and twenty-third nucleotide of the antisense strand $(N)_x$, and whereby the very same modification, i.e. a 2'-OMe group, was present at the second, fourth, sixth, eighth, tenth, twelfth, fourteenth, sixteenth, eighteenth, twentieth and twenty-second nucleotide of the sense strand $(N')_y$. Additionally, it is to be noted that these particular siRNA compounds are also blunt ended.

In certain embodiments of the compounds of the invention having alternating ribonucleotides modified in one or both of the antisense and the sense strands of the compound; for 19-mers and 23-mers the ribonucleotides at the 5' and 3' termini of the antisense strand are modified in their sugar residues, and the ribonucleotides at the 5' and 3' termini of the sense strand are unmodified in their sugar residues. For 21-mers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

In preferred embodiments of the invention, alternating ribonucleotides are modified in both the antisense and the sense strands of the compound. In particular the siRNA used in the Examples has been such modified such that a 2' 0-Me group was present on the first, third, fifth, seventh, ninth, eleventh, thirteenth, fifteenth, seventeenth and nineteenth nucleotide of the antisense strand, whereby the very same modification, i.e. a 2'-O-Me group was present at the second, fourth, sixth, eighth, tenth, twelfth, fourteenth, sixteenth and eighteenth nucleotide of the sense strand. Additionally, it is to be noted that the in case of these particular nucleic acids according to the present invention the first stretch is identical to the first strand and the second stretch is identical to the second strand and these nucleic acids are also blunt ended.

In a particularly preferred embodiment the sequence of the siRNA is that of 15 in Table A (sense strand SEQ ID NO 25; antisense strand SEQ ID NO 48).

According to one preferred embodiment of the invention, the antisense and the sense strands of the siRNA molecule are both phosphorylated only at the 3'-terminus and not at the 5'-terminus. According to another preferred embodiment of the invention, the antisense and the sense strands are both non-phosphorylated both at the 3'-terminus and also at the 5'-terminus. According to yet another preferred embodiment of the invention, the $1^{st}$ nucleotide in the 5' position in the sense strand is specifically modified to abolish any possibility of in vivo 5'-phosphorylation.

In various preferred embodiments compounds of the invention having alternating ribonucleotides modified in both the antisense and the sense strands of the compound, for 19-mer oligomers and 23-mer oligomers the ribonucleotides at the 5' and 3' termini of the antisense strand are modified in their sugar residues, and the ribonucleotides at the 5' and 3' termini of the sense strand are unmodified in their sugar residues. For 21-mer oligomers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

The invention further provides a vector capable of expressing any of the aforementioned oligoribonucleotides in unmodified form in a cell after which appropriate modification may be made.

The invention also provides a composition comprising one or more of the compounds of the invention in a carrier, preferably a pharmaceutically acceptable carrier. This composition may comprise a mixture of two or more different siRNAs.

The invention also provides a composition which comprises the above compound of the invention covalently or non-covalently bound to one or more compounds of the invention in an amount effective to inhibit human p53 and a carrier. This composition may be processed intracellularly by endogenous cellular complexes to produce one or more oligoribonucleotides of the invention.

The invention also provides a composition comprising a carrier and one or more of the compounds of the invention in an amount effective to down-regulate expression in a cell of a human p53, which compound comprises a sequence substantially complementary to the sequence of $(N)_x$.

Additionally the invention provides a method of down-regulating the expression of gene p53 by at least 50% as compared to a control comprising contacting an mRNA transcript of gene p53 with one or more of the compounds of the invention.

Additionally, the invention provides a method of inhibiting the expression of p53 by at least 20%, preferably 30%, even more preferably 40% or even 50% as compared to a control comprising contacting an mRNA transcript of p53 with one or more of the compounds of the invention.

In one embodiment the oligoribonucleotide is down-regulating p53, whereby the down-regulation of p53 is selected from the group comprising down-regulation of gene function, down-regulation of polypeptide and down-regulation of mRNA expression.

In one embodiment the compound is down-regulating a p53 polypeptide, whereby the down-regulation is selected from the group comprising down-regulation of function (which may be examined by an enzymatic assay or a binding assay with a known interactor of the native gene/polypeptide, inter cilia), down-regulation of protein (which may be examined by Western blotting, ELISA or immuno-precipitation, inter alia) and down-regulation of mRNA expression (which may be examined by Northern blotting, quantitative RT-PCR, in-situ hybridisation or microarray hybridisation, inter alia).

More particularly, the invention provides an oligoribonucleotide wherein one strand comprises consecutive nucleotides having, from 5' to 3', the sequence set forth in SEQ ID NOS: 3-25 (Table A, sense strands) or in SEQ ID NOS: 49-119 (Table B, sense strands) or in SEQ ID NOS: 191-253 (Table C1, sense strands), or in SEQ ID NOS: 319-353 (Table C2, sense strands) or a homolog thereof wherein in up to 2 of the nucleotides in each terminal region a base is altered.

The terminal region of the oligonucleotide refers to bases 1-4 and/or 16-19 in the 19-mer sequence, or to bases 1-4 and/or 18-21 in the 21-mer sequence or to bases 1-4 and/or 20-23 in the 23-mer sequence.

Additionally, the invention provides oligoribonucleotides wherein one strand comprises consecutive nucleotides having, from 5' to 3', the sequence set forth SEQ ID NOS: 26-48 (Table A, antisense strands) or SEQ ID NOS: 120-190 (Table B, antisense strands) or SEQ ID NOS: 254-316 (Table C1, antisense strands), or SEQ ID NOS: 354-388 (Table C2, antisense strands) or a homolog thereof wherein in up to 2 of the nucleotides in each terminal region a base is altered.

Preferred list of siRNA (sense and antisense strands) directed to p53 are in Tables A, B, C1 and C2.

The preferred oligonucleotides of the invention are human p53 oligonucleotides serial numbers 3, 5, 20 and 23 in Table D and mouse p53 oligonucleotides serial numbers 1 11, 12, 14, 17 and 18 in Table E. These are identical to serial numbers 3, 5, 20 and 23 (human) and also 11, 12, 14, 17 and 18 (mouse) in Table A. The most preferred oligonucleotides of the invention are human p53 oligonucleotides having the sequence of serial number 23 in Table A.

The presently most preferred compound of the invention is a blunt-ended 19-mer oligonucleotide, i.e. x=y=19 and Z and Z' are both absent. The oligonucleotide molecule is either phosphorylated at 3' termini of both sense and anti-sense strands, or non-phosphorylated at all; or having nucleotide $1^{st}$ nucleotide in the 5' position on the sense strand specifically modified to abolish any possibility of in vivo 5'-phosphorylation. The alternating ribonucleotides are modified at the 2' position in both the antisense and the sense strands, wherein the moiety at the 2' position is methoxy (2'-0-methyl) and wherein the ribonucleotides at the 5' and 3' termini of the antisense strand are modified in their sugar residues, and the ribonucleotides at the 5' and 3' termini of the sense strand are unmodified in their sugar residues. The presently most preferred such compounds are such modified oligonucleotides comprising the sequences having serial number 23 in Table A.

In one aspect of the invention the oligonucleotide comprises a double-stranded structure, whereby such double-stranded structure comprises a first strand and a second strand, whereby
the first strand comprises a first stretch of contiguous nucleotides and the second strand comprises a second stretch of contiguous nucleotides, whereby
the first stretch is either complementary or identical to a nucleic acid sequence coding for p53 and whereby the second stretch is either identical or complementary to a nucleic acid sequence coding for p53.

In an embodiment the first stretch and for the second stretch comprises from about 14 to 40 nucleotides, preferably about 18 to 30 nucleotides, more preferably from about 19 to 27 nucleotides and most preferably from about 19 to 23 nucleotides, in particular from about 19 to 21 or from about 19 to 23 nucleotides. In such an embodiment the oligonucleotide may be 17-40 nucleotides in length.

Additionally, further nucleic acids according to the present invention comprise at least 14 contiguous nucleotides of any one of the polynucleotides in Tables A, B, C1 or C2 and more preferably 14 contiguous nucleotide base pairs at any end of the double-stranded structure comprised of the first stretch and second stretch as described above.

In an embodiment the first stretch comprises a sequence of at least 14 contiguous nucleotides of an oligonucleotide, whereby such oligonucleotide is selected from the group comprising SEQ. ID. NOS 3-388, preferably from the group comprising the oligoribonucleotides of having the sequence of any of the serial numbers 3, 5, 20 or 23 (human) or having the sequence of any of the serial numbers 11, 12, 14, 17 and 18 (mouse) in Table A, more preferably selected from the group having the sequence of any of the serial numbers 3, 5, 20 or 23 in Table A.

Additionally, further nucleic acids according to the present invention comprise at least 14 contiguous nucleotides of any one of the SEQ. ID. NO. 3 to 388, and more preferably 14 contiguous nucleotide base pairs at any end of the double-stranded structure comprised of the first stretch and second stretch as described above. It will be understood by one skilled in the art that given the potential length of the nucleic acid according to the present invention and particularly of the individual stretches forming such nucleic acid according to the present invention, some shifts relative to the coding sequence of p53 to each side is possible, whereby such shifts can be up to 1, 2, 3, 4, 5 and 6 nucleotides in both directions, and whereby the thus generated double-stranded nucleic acid molecules shall also be within the present invention.

In another aspect, the present invention relates to a method for the treatment of a subject in need of treatment for a disease or disorder associated with the abnormal expression of p53, comprising administering to the subject an amount of an inhibitor which reduces or inhibits expression of p53.

The methods of the invention comprise administering to the patient one or more inhibitory compounds which downregulate expression of p53; and in particular siRNA in a therapeutically effective dose so as to thereby treat the patient.

In various embodiments the inhibitor is selected from the group consisting of an siRNA, shRNA, an aptamer, an antisense molecule, miRNA, a ribozyme, and an antibody. In preferred embodiments the inhibitor is siRNA.

Delivery: The siRNA molecules of the present invention may be delivered to the target tissue (such as the cochlea) by direct application of the naked molecules admixed with a carrier or a diluent within the cochlea.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA". However, the siRNA molecules of the invention can also be delivered in liposome formulations and lipofectin formulations and the like and can be prepared by methods well known to those skilled in the art. Such methods are described, for example, in U.S. Pat. Nos. 5,593,972, 5,589, 466, and 5,580,859, which are herein incorporated by reference.

Delivery systems aimed specifically at the enhanced and improved delivery of siRNA into mammalian cells have been developed, see, for example, Shen et al (FEBS letters 539: 111-114 (2003)). Xia et al., Nature Biotechnology 20: 1006-1010 (2002), Reich et al., Molecular Vision 9: 210-216 (2003), Sorensen et al. (J. Mol. Biol. 327: 761-766 (2003), Lewis et al., Nature Genetics 32: 107-108 (2002) and Simeoni et al., Nucleic Acids Research 31, 11: 2717-2724 (2003). siRNA has recently been successfully used for inhibition in primates; for further details see Tolentino et al., Retina 24(1) February 2004 I 132-138. Respiratory formulations for siRNA are described in U.S. patent application No. 2004/0063654 of Davis et al. Cholesterol-conjugated siRNAs (and other steroid and lipid conjugated siRNAs) can been used for delivery see Soutschek et al Nature 432: 173-177(2004) *Therapeutic silencing of an endogenous gene by systemic administration of modified siRNAs*; and Lorenz et al. Bioorg. Med. Chemistry. Lett. 14:4975-4977 (2004) *Steroid and lipid conjugates of siRNAs to enhance cellular uptake and gene silencing in liver cells.*

The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In addition, under certain circumstances the compositions for use in the novel treatments of the present invention may be formed as aerosols, for intranasal and like administration. The patient being treated is a warm-blooded animal and, in particular, mammals including man. The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations are particularly preferred.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer. In a particular embodiment, the administration comprises intravenous administration of the siRNA compound. Preferred doses are in the range of 0.1-25 mg/kg body weight, more preferably, in the range of 0, 5-10 mg/kg body weight.

In another particular embodiment the administration comprises topical or local administration "Treatment" refers to both therapeutic treatment and prophylactic or preventative measures, wherein the object is to prevent or slow down (lessen) pro-apoptotic-related disorder as listed above. Those in need of treatment include those already experiencing the disease or condition, those prone to having the disease or condition, and those in which the disease or condition is to be prevented. The compounds of the invention may be administered before, during or subsequent to the onset of the disease or condition.

In another aspect of the invention a pharmaceutical composition is provided which comprises any of the above oligoribonucleotides (SEQ ID NOS: 3-388) or vectors and a pharmaceutically acceptable carrier. Another aspect of the invention is the use of a therapeutically effective amount of any of the above oligoribonucleotides (SEQ ID NOS: 3-388) or vectors for the preparation of a medicament for treating a patient suffering from a disorder which is accompanied by an elevated level of p53.

The present invention relates to the use of compounds which down-regulate the expression of the p53 gene, particularly to small interfering RNAs (siRNAs), in the treatment of hearing impairment or acute renal failure. Methods, molecules and compositions which inhibit p53 are discussed herein at length, and any of said molecules and/or compositions may be beneficially employed in the treatment of a patient suffering from any of said conditions. Preferred lists of siRNA directed to p53 are in Tables A, B, C1 and C2. Other siRNA sequences directed to RTP801 to be used in the present invention may be found in co-pending PCT publication number WO06/023544A2 (PCT/US2005/029236) or U.S. application Ser. No. 11/207,119, which are incorporated by reference in their entirety.

"Treatment" refers to both therapeutic treatment and prophylactic or preventative measures, wherein the object is to prevent or slow down (lessen) an apoptotic-related disorder such as hearing disorder or impairment (or balance impairment), preferably ototoxin-induced or traumatic inner ear hair cells apoptotic damage. Those in need of treatment include those already experiencing a hearing impairment, those prone to having the impairment, and those in which the impairment is to be prevented. Without being bound by theory, the hearing impairment may be due to apoptotic inner ear hair cell damage or loss, wherein the damage or loss is caused by infection, mechanical injury, loud sound, aging, or, in particular, chemical-induced ototoxicity. Ototoxins include therapeutic drugs including antineoplastic agents, salicylates, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxin" in the context of the present invention is meant a substance that through its chemical action injures, impairs or inhibits the activity of the sound receptors component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, neoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and over-doses of vitamins or therapeutic drugs, e.g., antibiotics such as penicillin or chloramphenicol, and megadoses of vitamins A, D, or B6, salicylates, quinines and loop diuretics. By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

Hearing impairment relevant to the invention may be due to end-organ lesions involving inner ear hair cells, e.g., acoustic trauma, viral endolymphatic labyrinthitis, Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenoviruses. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome.

The hearing loss can be noise-induced, generally due to a noise greater than 85 decibels (db) that damages the inner ear. In a particular aspect of the invention, the hearing loss is caused by an ototoxic drug that effects the auditory portion of the inner ear, particularly inner ear hair cells. Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

In one embodiment, the present invention constitutes a method for treating a mammal having or prone to a hearing (or balance) impairment or treating a mammal prophylactically in conditions where inhibition of expression of p53 is beneficial. The method of the present invention would prevent or reduce the occurrence or severity of a hearing (or balance) impairment that would result from inner ear cell injury, loss, or degeneration, in particular caused by an ototoxic agent. The method of the invention includes administering a therapeutically effective amount of one or more compounds which down-regulate expression of the p53 gene, particularly the novel siRNAs of the present invention, small molecule inhibitors of p53 as described herein or antibodies to p53 polypeptide.

It is the object of the present invention to provide a method and compositions for treating a mammal, to prevent, reduce, or treat a hearing impairment, disorder or imbalance, preferably an ototoxin-induced hearing condition, by administering to a mammal in need of such treatment a composition of the invention. One embodiment of the invention is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

The methods and compositions of the present invention are also effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2.

The methods and compositions of the present invention are also effective when the ototoxic compound is a neoplastic agent such as vincristine, vinblastine, cisplatin and cisplatin-like compounds and taxol and taxol-like compounds.

The methods and compositions of the present invention are also effective in the treatment of accoustic trauma or mechanical trauma, preferably accoustic or mechanical trauma that leads to inner ear hair cell loss or outer ear hair cell loss. Accoustic trauma to be treated in the present invention may be caused by a single exposure to an extremely loud sound of above 120-140 decibels, or following long-term exposure to everyday loud sounds above 85 decibels. The compositions of the present invention are also effective as a preventive treatment in patients expecting an acoustic trauma. Mechanical inner ear trauma to be treated in the present invention is for example the inner ear trauma following an operation for insertion of an electronic device in the inner ear. The compositions of the present invention prevent or minimize the damage to inner ear hair cells associated with this operation.

In some embodiments the composition of the invention is co-administered with an ototoxin. For example, an improved method is provided for treatment of infection of a mammal by administration of an aminoglycoside antibiotic, the improvement comprising administering a therapeutically effective amount of one or more compounds (particularly novel siRNAs) which down-regulate expression of the p53 gene, to the patient in need of such treatment to reduce or prevent ototoxin-induced hearing impairment associated with the antibiotic. The compounds which down-regulate expression of the p53 gene, particularly novel siRNAs are preferably administered locally within the inner ear.

In yet another embodiment an improved method for treatment of cancer in a mammal by administration of a chemotherapeutic compound is provided, wherein the improvement comprises administering a therapeutically effective amount of a composition of the invention to the patient in need of such treatment to reduce or prevent ototoxin-induced hearing impairment associated with the chemotherapeutic drug. The compounds which reduce or prevent the ototoxin-induced hearing impairment, eg the novel siRNAs inter alia are preferable administered directly to the cochlea as naked siRNA in a vehicle such as PBS or other physiological solutions, but may alternatively be administered with a delivery vehicle as described above.

In another embodiment the methods of treatment are applied to treatment of hearing impairment resulting from the administration of a chemotherapeutic agent in order to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include carboplatin (Paraplatin®), tetraplatin, oxaliplatin, aroplatin and transplatin inter alia.

In another embodiment the methods of the invention are applied to hearing impairments resulting from the administration of quinine and its synthetic substitutes, typically used in the treatment of malaria, to treat its ototoxic side-effect.

In another embodiment the methods of the invention are applied to hearing impairments resulting from administration of a diuretic to treat its ototoxic side-effect. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics also used in nonedematous states for example hypertension, hypercalcemia, idiopathic hypercalciuria, and nephrogenic diabetes insipidus.

In another preferred embodiment, the compositions of the present invention are used for the treatment of acute renal failure. In yet another preferred embodiment, the compositions of the present invention are used in conditions in which a p53 gene is activated as a consequence of a variety of stresses associated with injuries such as a burn, hyperthermia, hypoxia associated with a blocked blood supply such as in myocardial infraction, stroke, and ischemia. Temporary p53 inhibition using the siRNA molecules of the present invention can be therapeutically effective in reducing or eliminating p53-dependent neuronal death in the central nervous system, i.e., brain and spinal cord injury, in preserving of tissue and an organ prior to transplanting, preparation of a host for a hone marrow transplant, reducing or eliminating neuronal damage during a seizure and in suppressing tissue aging.

The invention also provides a use of a therapeutically effective dose of one or more compounds of the invention for the preparation of a composition for the treatment of a disease accompanied by an elevated level of p53, such as in a patient suffering from acute kidney injury such as acute renal failure. Preferably, the composition is for the treatment of renal ischemia-reperfusion injury, most preferably renal ischemia-reperfusion injury in patients undergoing major surgery such as major cardiac surgery which may result in acute renal failure.

In a particular embodiment in which the siRNA compounds are delivered to the target cells in the kidney, the siRNA compounds are preferably administered by intravenous injection. The inventors have unexpectedly discovered that a single injection of p53 siRNA compounds between 2 to 24, preferably 2-8 hours following the kidney ischemic-reperfusion event in animals is especially effective in reducing the damage in the kidney. In the most preferred embodiment, the p53 siRNA compounds are injected 4 hours following the kidney ischemic-reperfusion event or following the removal of the cardiopulmonary bypass machine. It is also envisaged that two or more injections may be administered in this time period and injections may be given 1, 2, 3, 4, 5, 6, 7, 8, 12 or 24 hours following the kidney ischemic-reperfusion event or following the removal of the cardiopulmonary bypass machine It is noted that the delivery of the siRNA compounds according to the present invention to the target cells in the kidney proximal tubules is particularity effective in the treatment of acute renal failure. Without being bound by theory, this may be due to the fact that siRNA molecules are excreted from the body via the cells of the kidney proximal tubules. Thus, naked siRNA molecules are naturally concentrated in the cells that are targeted for the therapy in acute renal failure.

The compounds of the invention are preferably used for treating acute renal failure, in particular acute renal failure due to ischemia in post surgical patients, and acute renal failure due to chemotherapy treatment such as cisplatin administration or sepsis-associated acute renal failure. A preferred use of the compounds of the invention is for the prevention of acute renal failure in high-risk patients undergoing major cardiac surgery or vascular surgery. The patients at high-risk of developing acute renal failure can be identified using various scoring methods such as the Cleveland Clinic algorithm or that developed by US Academic Hospitals (QMMI) and by Veterans' Administration (CICSS).

Other preferred uses of the compounds of the invention are for the prevention of ischemic acute renal failure in kidney transplant patients or for the prevention of toxic acute renal failure in patients receiving chemotherapy or other chemicals causing nephrotoxicity. Such nephrotoxins are for example: cardiovascular drugs such as diuretics, β-blockers, vasodilator agents. ACE inhibitors, ciclosporin. Aminoglycoside antibiotics (e.g. gentamicin), amphotericin B, cisplatin, radio-contrast media, immunoglobulins, mannitol, NSAIDs (e.g. aspirin, ibuprofen, diclofenac), ciclosporin, lithium salts, cyclophosphamide, amphotericin B, sulphonamides, methotrexate, aciclovir, polyethylene glycol, β-lactam antibiotics, vancomycin, rifampicin, sulphonamides, ciprofloxacin, ranitidine, cimetidine, furosemide, thiazides, phenyloin, Penicillamine, amphotericin B, fluoride, demeclocycline, foscarnet, Heavy metals.

Other uses are for wound healing, acute liver failure, drug-induced deafness (perhaps topically), ex vivo expansion of hematopoietic stem cells, preservation of donor organs/tissues before transplantation by soaking in siRNA solution (perhaps by electroporation) and subsequent improvement of graft tissue survival following transplantation. Other indications may be stroke, Parkinson's disease, Alzheimer's disease, doxorubicin-induced cardiotoxicity, myocardial infarction/heart failure and improvement of graft tissue survival following transplantation (by systemic administration). Without being bound by theory all these disorders are accompanied by an elevated level of p53 polypeptide.

The present invention also provides for a process of preparing a pharmaceutical composition, which comprises:
  obtaining one or more double stranded compound of the invention; and
  admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Modifications or analogs of nucleotides can be introduced to improve the therapeutic properties of the nucleotides. Improved properties include increased nuclease resistance and/or increased ability to permeate cell membranes.

Accordingly, the present invention also includes all analogs of, or modifications to, a oligonucleotide of the invention that does not substantially affect the function of the polynucleotide or oligonucleotide. In a preferred embodiment such modification is related to the base moiety of the nucleotide, to the sugar moiety of the nucleotide and/or to the phosphate moiety of the nucleotide.

In embodiments of the invention, the nucleotides can be selected from naturally occurring or synthetically modified bases. Naturally occurring bases include adenine, guanine, cytosine, thymine and uracil. Modified bases of the oligonucleotides include inosine, xanthine, hypoxanthine, 2-aminoadenine, 6-methyl-, 2-propyl- and other alkyl-adenines, 5-halo uracil, 5-halo cytosine, 6-aza cytosine and 6-aza thymine, pseudo uracil, 4-thiuracil, 8-halo adenine, 8-aminoadenine, 8-thiol adenine, 8-thiolalkyl adenine, 8-hydroxyl adenine and other 8-substituted adenines, 8-halo guanine, 8-amino guanine, 8-thiol guanine, 8-thioalkyl guanine, 8-hydroxyl guanine and other substituted guanines, other aza and deaza adenines, other aza and deaza guanines, 5-trifluoromethyl uracil and 5-trifluoro cytosine.

In addition, analogs of polynucleotides can be prepared wherein the structure of one or more nucleotide is fundamentally altered and better suited as therapeutic or experimental reagents.

An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholine nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of siRNA compounds comprising LNA nucleotides are disclosed in Elmen et al., (NAR 2005. 33(1): 439-447).

The compounds of the present invention can be synthesized using one or more inverted nucleotides, for example inverted thymidine or inverted adenine (for example see Takei, et al., 2002. JBC 277(26):23800-06.

Certain structures include an siRNA compound having one or a plurality of internucleotide linkages (bridges).

A "mirror" nucleotide is a nucleotide with reversed chirality to the naturally occurring or commonly employed nucleotide, i.e., a mirror image (L-nucleotide) of the naturally occurring (ID-nucleotide). The nucleotide can be a ribonucleotide or a deoxyribonucleotide and my further comprise at least one sugar, base and or backbone modification. U.S. Pat. No. 6,602,858 discloses nucleic acid catalysts comprising at least one L-nucleotide substitution.

In one embodiment the modification is a modification of the phosphate moiety, whereby the modified phosphate moiety is selected from the group comprising phosphothioate.

The compounds of the present invention can be synthesized by any of the methods that are well-known in the art for synthesis of ribonucleic (or deoxyribonucleic) oligonucleotides. Such synthesis is, among others, described in Beaucage S. L. and Iyer R. P., Tetrahedron 1992; 48: 2223-2311, Beaucage S. L. and Iyer R. P., Tetrahedron 1993; 49: 6123-6194 and Caruthers M. H. et. al., Methods Enzymol. 1987; 154: 287-313; the synthesis of thioates is, among others, described in Eckstein F., Annu. Rev. Biochem. 1985; 54: 367-402, the synthesis of RNA molecules is described in Sproat B., in Humana Press 2005 edited by Herdewijn P.; Kap. 2: 17-31 and respective downstream processes are, among others, described in Pingoud A. et. al., in IRL Press 1989 edited by Oliver R. W. A.; Kap. 7: 183-208 and Sproat B., in Humana Press 2005 edited by Herdewijn P.; Kap. 2: 17-31 (supra).

Other synthetic procedures are known in the art e.g. the procedures as described in Usman et al., 1987, *J. Am. Chem. Soc.*, 109, 7845; Scaringe et al., 1990, *Nucleic Acids Res.*, 18, 5433; Wincott et al., 1995, *Nucleic Acids Res.* 23, 2677-2684; and Wincott et al., 1997, *Methods Mol. Bio.*, 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992, *Science* 256, 9923; Draper et al., International PCT publication No. WO93/23569; Shabarova et al., 1991, *Nucleic Acids Research* 19, 4247; Belton et al., 1997, *Nucleosides & Nucleotides*, 16, 951; Bellon et al., 1997, *Bioconjugate Chem.* 8, 204), or by hybridization following synthesis and/or deprotection.

It is noted that a commercially available machine (available, inter cilia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via a tandem synthesis methodology, as described in US patent application publication No. US2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two siRNA sequences are selected from Tables A, B, C1 and C2, preferably from Table A, ID Nos: 3, 5, 20 and 23 (human sequences) and 11, 12, 14, 17 and 18 (mouse sequences).

In another embodiment, the siRNA molecules are comprised of a double-stranded nucleic acid structure, wherein the first siRNA sequence is selected from Tables A, B, C1 or C2, preferably from Table A, ID Nos: 3, 5, 20 and 23 (human p53 sequences) or 11, 12, 14, 17 and 18 (mouse p53 sequences) and the second siRNA molecule targets a pro-apoptotic gene, thereby providing beneficial activity. The tandem double-stranded structure which comprises two or more siRNA sequences is processed intracellularly to form two or more different siRNAs. Such second siRNA molecule is preferably an siRNA molecule that targets a pro-apoptotic gene.

The siRNA molecules are covalently or non-covalently bound or joined by a linker to form a tandem siRNA molecule. Such tandem siRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem molecule comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention.

siRNA molecules that target p53 may be the main active component in a pharmaceutical composition, or may be one active component of a pharmaceutical composition containing two or inure siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of p53 and said additional gene(s) will likely have an additive or synergistic effect for treatment of the diseases disclosed herein.

In a specific example, the pharmaceutical composition for treatment of the diseases disclosed herein may be comprised of the following compound combinations: 1) p53 siRNA and Fas siRNA: 2) p53 siRNA and Bax siRNA; 3) p53 siRNA and Noxa siRNA: 4) p53 siRNA and Puma siRNA; 5) p53 siRNA and RTP801 siRNA: 6) p53 siRNA and PIDD siRNA: 7) p53 siRNA, Fas siRNA and any of RTP801 siRNA, Bax siRNA, Noxa siRNA or Puma siRNA or PIDD siRNA to form trimers or polymers (i.e., tandem molecules which encode three siRNAs). Other preferred options of pro-apoptotic genes are siRNA combinations of any of p53, TNFα, caspase 2, caspase 3, caspase 9. E2F1, and PARP-1. A preferred combination according to the present invention is p53 siRNA and RTP801 siRNA. (see PCT patent application PCT/US2005/029236).

As disclosed herein, aptamers may also be used in the present invention alone or in combination with the novel siRNAs disclosed herein for targeting p53 of the invention and for the treatment of any one of the conditions disclosed herein. For example, an aptamer can be used with any one of the siRNAs disclosed herein in combination therapy for the treatment of any one of the conditions disclosed herein. The novel pharmaceutical composition employed for such a combination therapy, which is also part of the present invention, may comprise an siRNA of the present invention covalently or non-covalently attached to an aptamer. Aptamers are RNA or DNA single-strand or double-strand oligonucleic acids which bind to a target protein and do not generally exhibit non-specific effects. Aptamers can be modified for stability or other desired qualities in accordance with any nucleic acid modifications disclosed herein and/or known to one of skill in the art. Modifications to aptamers can be introduced anywhere in the molecule, such as the 5' or 3' termini, or at any internally defined modification site. For example, RNA aptamers can be stabilized with 2'-Fluoro or 2'-amino modified pyrimidines. Aptamers can also be linked to reporter molecules or linker chemistries and can be attached to beads or other solid support if necessary (e.g., 5' or 3' amino, thiol ester or biotin groups). Thioaptamers are aptamers which contain sulfur modifications at specific internucleoside phosphoryl sites, and may possess enhanced stability, nuclease resistance, target affinity and/or selectivity. Examples of thioaptamers include phosphoromonothioate (S-ODN) and phosphorodithioate (S2-ODN) oligodeoxy thioaptamers. For further information on aptamers and thioaptamers see U.S. Pat. Nos. 5,218,088 and 6,423,493.

Additionally, the siRNA disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with a p53 siRNA molecule. In another example, an aptamer which can act like a ligand/antibody may be combined (covalently or non-covalently) with a p53 siRNA molecule.

The term "Covalent bonding" as used herein refers to chemical bonding that is characterized by the sharing of pairs of electrons between atoms.

The term "Noncovalent bonding" as used herein refers to a variety of interactions that are not covalent in nature between molecules or parts of molecules that provide force to hold the molecules or parts of molecules together, usually in a specific orientation or conformation. These noncovalent interactions include: ionic bonds, hydrophobic interactions, hydrogen bonds, Van der Waals forces and Dipole-dipole bonds.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

In one specific embodiment of this invention, topical, intracochlear, transtympanic and transdermal formulations are particularly preferred. They can be administered by subcutaneous injection. Additionally, they can be administered by implants, in liquid drops to the ear canal, delivered to the scala tympani chamber the inner ear by transtympa injection, or provided as a diffusible member of a cochlear hearing implant.

A preferred administration mode is directly to the affected portion of the ear or vestibule, topically as by implant for example, and, preferably to the affected hair cells or their supporting cells, so as to direct the active molecules to the source and minimize its side effects. A preferred administration mode is a topical delivery of the p53 inhibitor(s) onto the round window membrane of the cochlea. Such a method of administration of other compounds is disclosed for example in Tanaka et al. (Hear Res. 2003 March; 177(1-2):21-31).

As noted, the compositions can be injected through chronically implanted cannulas or chronically infused with the help of osmotic minipumps. Subcutaneous pumps are available that deliver active compounds through a small tubing to the appropriate area. Highly sophisticated pumps can be refilled through the skin and their delivery rate can be set without surgical intervention. Examples of suitable administration protocols and delivery systems involving a subcutaneous pump device or continuous infusion through a totally implanted drug delivery system are described for example by Harbaugh, *J. Neural Transm. Suppl.*, 24: 271-277 (1987) and DeYebenes et al., *Mov. Disord.*, 2: 143-158 (1987), the disclosures of which are incorporated herein by reference.

Delivery of therapeutic agents to the inner ear of a subject can be done by contact with the inner ear or through the external auditory canal and middle ear, as by injection or via catheters, or as exemplified in U.S. Pat. No. 5,476,446, which provides a multi-functional apparatus specifically designed for use in treating and/or diagnosing the inner ear of a human subject. The apparatus is capable of delivering therapeutic agents into the inner ear or to middle-inner ear interface tissues. In addition, other systems may be used to deliver the molecules of the present invention including but not limited to an osmotic pump which is described in Kingma, G. G., et al., "Chronic drug infusion into the scala tympani of the guinea pig cochlea", *Journal of Neuroscience Methods*, 45:127-134 (1992). An exemplary, commercially-available osmotic pump may be obtained from the Alza Corp. of Palo Alto, Calif. (USA).

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of an p53 gene. In particular, it is envisaged that this oligonucleotide comprises sense and antisense siRNA sequences as depicted in any one of Tables A, B, C1 and C2.

As used herein, the term "polypeptide" refers to, in addition to a polypeptide, an oligopeptide, peptide and a full protein.

As used herein, the term "inhibition" of p53 means inhibition of the gene expression (transcription or translation) or polypeptide activity.

Although the inhibitor may be an siRNA molecule, other inhibitors contemplated to be used in the methods of the invention to inhibit p53 and to treat the diseases and conditions described herein are inter alia, antisense oligonucleotides, antisense DNA or RNA molecules, proteins, polypeptides and peptides including peptido-mimetics and dominant negatives, and also expression vectors expressing all the above. Additional inhibitors may be small chemical molecules, which generally have a molecular weight of less than 2000 daltons, more preferably less than 1000 daltons, even more preferably less than 500 daltons. These inhibitors may act as follows: small molecules may affect expression and/or activity; antibodies may affect activity; all kinds of antisense may affect the pro-apoptotic gene expression; and dominant negative polypeptides and peptidomimetics may affect activity; expression vectors may be used inter cilia for delivery of antisense or dominant-negative polypeptides or antibodies.

Antisense Molecules

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its therapeutic potential (Aboul-Fadl T. Curr Med. Chem. 2005, 12(19):2193-214; Crooke S T, Curr Mol Med. 2004, 4(5): 465-87; Crooke S T, Ann Rev Med. 2004, 55:61-95; Vacek M et al., Cell Mol Life Sci, 2003, 60(5):825-33; Cho-Chung Y S, Arch Pharm Res. 2003, 26(3):183-91. There are further reviews on the chemical (Crooke et al., Hematol Pathol. 1995, 9(2):59-72), cellular (Wagner, Nature. 1994, 372(6504):333-5) and therapeutic (Scanlon, et al, FASEB J. 1995, 9(13): 1288-96) aspects of AS technology. Antisense intervention in the expression of specific genes can be achieved by the use of modified AS oligonucleotide sequences (for recent reports see Lefebvre-d'Hellencourt et al, 1995; Agrawal, 1996: Lev-Lehman et al, 1997).

AS oligonucleotide sequences may be short sequences of DNA, typically 15-30 mer but may be as small as 7-mer (Wagner et al, Nat. Biotech. 1996, 14(7):840-4), designed to complement a target mRNA of interest and form art RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, Semin Oncol. 1996, 23(1):78-87). In that case, RNase H will cleave the RNA component of the duplex and can potentially release the AS to further hybridize with additional molecules of the target RNA. An additional mode of action results from the interaction of AS with genomic DNA to form a triple helix, which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996, Biochem. Biophys. Res. Comm. 229:305-309). For example, the computer program OLIGO (Primer Analysis Software, Version 3.4), can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection is known in the art. Further, the oligonucleotides are also selected as needed so that analog substitution does not substantially affect function.

Phosphorothioate antisense oligonucleotides do not normally show significant toxicity at concentrations that are effective and exhibit sufficient pharmacodynamic half-lives in animals (Agrawal, et al., PNAS USA. 1997, 94(6):2620-5) and are nuclease resistant. Antisense oligonucleotide inhibition of basic fibroblast growth factor (bFGF), having mitogenic and angiogenic properties, suppressed 80% of growth in glioma cells (Morrison, J Biol Chem. 1991 266(2):728-34) in a saturable and specific manner. Being hydrophobic, antisense oligonucleotides interact well with phospholipid membranes (Akhter et al., NAR. 1991, 19:5551-5559). Following their interaction with the cellular plasma membrane, they are actively (or passively) transported into living cells (Loke et al., PNAS 1989, 86(10):3474-8), in a saturable mechanism predicted to involve specific receptors (Yakubov et al., PNAS, 1989 86(17):6454-58).

Ribozymes

A "ribozyme" is an RNA molecule that possesses RNA catalytic ability (see Cech for review) and cleaves a specific site in a target RNA. In accordance with the present invention, ribozymes which cleave mRNA may be utilized as inhibitors. This may be necessary in cases where antisense therapy is limited by stoichiometric considerations (Sarver et al., 1990, *Gene Regulation and Aids, pp.* 305-325). Ribozymes can then be used that will target the a gene associated with a bone marrow disease. The number of RNA molecules that are cleaved by a ribozyme is greater than the number predicted by stochiochemistry. (Hampel and Tritz, Biochem. 1989, 28(12):4929-33; Uhlenbeck, Nature. 1987 328(6131):596-600).

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

Screening of Inactivation Compounds for p53:

Some of the compounds and compositions of the present invention may be used in a screening assay for identifying and isolating compounds that modulate the activity of a p53 gene, in particular compounds that modulate a disorder accompanied by an elevated level of p53 polypeptide. The compounds to be screened comprise inter alia substances such as small chemical molecules and antisense oligonucleotides.

The inhibitory activity of the compounds of the present invention on p53 or binding of the compounds or the present invention to p53 gene may be used to determine the interaction of an additional compound with the p53 polypeptide, e.g., if the additional compound competes with the oligonucleotides of the present invention for inhibition of a p53 gene, or if the additional compound rescues said inhibition. The inhibition or activation can be tested by various means, such as, inter alia, assaying for the product of the activity of the p53 polypeptide or displacement of binding compound from the p53 polypeptide in radioactive or fluorescent competition assays.

The present invention is illustrated in detail below with reference to the Examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry can be used for detection of cells containing specific DNA and mRNA sequences (Testoni et al., 1996. Blood 87:3822.) Methods of performing RT-PCR are also well known in the art.

Example 1

Generation of Sequences for Active siRNA Compounds

Using proprietary algorithms and the known sequence of gene p53 (SEQ ID NO:1), the sequences of many potential siRNAs were generated. Table A shows 23 siRNAs which have so far been selected, chemically synthesized and tested for activity (see Example 2). All these siRNAs are 19-mers.

TABLE A

| Number | Index | Sense strand | Antisense strand | Species | NM_000546 (human) | NM_011640 (mouse) | NM_030989 (rat) |
|---|---|---|---|---|---|---|---|
| 1 | Mo3 | GUACAUGUGUAAUAGCUCC | GGAGCUAUUACACAUGUAC | mouse | 3 mis | 1232-1250 | 2 mis |
| 2 | Hu2' | GACUCCAGUGGUAAUCUAC | GUAGAUUACCACUGGAGUC | human* | 1026-1044 | 3 mis | 2 mis |
| 3 | QHMon1 | CAGACCUAUGGAAACUACU | AGUAGUUUCCAUAGGUCUG | hum, mon | 310-328 | 3 mis | 4 mis |
| 4 | QHMon2 | CUACCUCCCGCCAUAAAAA | UUUUUAUGGCGGGAGGUAG | hum, mon | 1378-1396 | 1 mis | 1 mis |
| 5 | QH1 | CCCAAGCAAUGGAUGAUUU | AAAUCAUCCAUUGCUUGGG | human | 361-379 | No | No |
| 6 | QH2 | CCCGGACGAUAUUGAACAA | UUGUUCAAUAUCGUCCGGG | human | 389-407 | No | No |
| 7 | QM1 | GAGUCACAGUCGGAUAUCA | UGAUAUCCGACUGUGACUC | mouse | No | 552-570 | 2 mis |
| 8 | QM2 | GGAUGUUGAGGAGUUUUUU | AAAAAACUCCUCAACAUCC | mouse | No | 680-698 | 4 mis |
| 9 | QM3 | CAUCUUUUGUCCCUUCUCA | UGAGAAGGGACAAAAGAUG | mouse | 2 mis | 808-826 | 2 mis |
| 10 | QM6 | GGAAUAGGUUGAUAGUUGU | ACAACUAUCAACCUAUUCC | mouse | No | 1870-1888 | No |
| 11 | QM4 | GGACAGCCAAGUCUGUUAU | AUAACAGACUUGCCUGUCC | mouse, rat | 2 mis | 877-895 | 527-545 |
| 12 | QM5 | GAAGAAAAUUUCCGCAAAA | UUUUGCGGAAAUUUUCUUC | mouse, rat | 3 mis | 1383-1401 | 1033-1051 |
| 13 | A17 | CUGGGACAGCCAAGUCUGU | ACAGACUUGGCUGUCCCAG | hum, mus | 598-616 | 874-892 | 2-mis |
| 14 | E2 | UCAUCACACUGGAAGACUC | GAGUCUUCCAGUGUGAUGA | hum, mus, rat | 1012-1030 | 1288-1306 | 938-956 |
| 15 | E6 | CACACUGGAAGACUCCAGU | ACUGGAGUCUUCCAGUGUG | hum, mus, rat | 1016-1034 | 1292-1310 | 942-960 |
| 16 | B1 | GCGCCAUGGCCAUCUACAA | UUGUAGAUGGCCAUGGCGC | hum mon, mus | 724-742 | 1000-1018 | 652-668(17) |
| 17 | B2 | CGCCAUGGCCAUCUACAAG | CUUGUAGAUGGCCAUGGCG | hum, mon, mus | 725-743 | 1001-1019 | 652-669(18) |

TABLE A-continued

| Number | Index | Sense strand | Antisense strand | Species | NM_000546 (human) | NM_011640 (mouse) | NM_030989 (rat) |
|---|---|---|---|---|---|---|---|
| 18 | C1 | AGUCACAGCACAUGACGGA | UCCGUCAUGUGCUGUGACU | hum, mon, mus | 745-763 | 1021-1039 | 2 mis |
| 19 | F2 | UCCGAGUGGAAGGAAAUUU | AAAUUUCCUUCCACUCGGA | hum, mon, dog | 835-853 | 1 mis | 3 mis |
| 20 | F3 | CCGAGUGGAAGGAAAUUUG | CAAAUUUCCUUCCACUCGG | hum, mon, dog | 836-854 | 1 mis | 3 mis |
| 21 | G1 | GACAGAAACACUUUUCGAC | GUCGAAAAGUGUUUCUGUC | mon, dog | 873-891 | No | No |
| 22 | H2 | GUGUGGUGGUGCCCUAUGA | UCAUAGGGCACCACCACAC | hum, mon, dog | 895-913 | 3 mis | 3 mis |
| 23 | I5 | GAGAAUAUUUCACCCUUCA | UGAAGGGUGAAAUAUUCUC | hum, mon, dog | 1225-1243 | 2 mis | 1 mis |

Note that in the above Table A, the sense strands of siRNAs 1-23 have SEQ ID NOS: 3-25 respectively, and the antisense strands of siRNAs 1-23 have SEQ ID NOS: 26-48 respectively. siRNA compound No 1 (sense strand SEQ ID NO: 3 and antisense strand SEQ ID NO: 26) is known from the literature (Dirac and Bernards, *Reversal of senescence in mouse fibroblasts through lentiviral suppression of p53*, J. Biol. Chem. (2003) 278:11731) and siRNA No 2 (sense strand SEQ ID NO: 4 and antisense strand SEQ ID NO: 27) is also known from the literature (Brummelkamp et al, *Science* 2002, 296:550-553). However, the use of these compounds in the methods of treatment disclosed herein is previously undisclosed and thus novel.

Table B below shows 71 additional 19-mer siRNAs which have been generated by the proprietary algorithms.

TABLE B

| No. | Source | Sense | AntiSense | gi13097806 gbBC003596.1 (*Homo sapiens*) | gi2689466 gbU48957.1 U48957 (*Macaca fascicularis*) | gi53575emb X01237.1MMP53R (Mouse mRNA) | gi4996229 dbjAB020761.1 (*Canis familiaris*) |
|---|---|---|---|---|---|---|---|
| 1 | Human | GUACCACCAUCCACUACAA | UUGUAGUGGAUGGUGGUAC | [806-824] | | [835-852] | |
| 2 | Human | GGAAACUACUUCCUGAAAA | UUUUCAGGAAGUAGUUUCC | [188-206] | | [234-247] | |
| 3 | Human | AGACUCCAGUGGUAAUCUA | UAGAUUACCACUGGAGUCU | [894-912] | | [922-933] | |
| 4 | Human | CCAUCCACUACAACUACAU | AUGUAGUUGUAGUGGAUGG | [812-830] | | [840-858] | |
| 5 | Human | CCACCAUCCACUACAACUA | UAGUUGUAGUGGAUGGUGG | [809-827] | | [837-852] | |
| 6 | Human | AAACACUUUUCGACAUAGU | ACUAUGUCGAAAAGUGUUU | [747-765] | | — | |
| 7 | Human | CAUGAGCGCUGCUCAGAUA | UAUCUGAGCAGCGCUCAUG | [655-673] | | [683-696] | |
| 8 | Human | CCAUGGCCAUCUACAAGCA | UGCUUGUAGAUGGCCAUGG | [596-614] | | [624-640] | |
| 9 | Human | CCAAGUCUGUGACUUGCAC | GUGCAAGUCACAGACUUGG | [476-494] | | — | |
| 10 | Human | AAACUUUGCUGCCAAAAAA | UUUUUUGGCAGCAAAGUUU | [2476-2494] | | — | |
| 11 | Human | CCCUCCUUCUCCCUUUUUA | UAAAAGGGAGAAGGAGGG | [2421-2439] | | — | |
| 12 | Human | GCAAGCACAUCUGCAUUUU | AAAAUGCAGAUGUGCUUGC | [2389-2407] | | — | |
| 13 | Human | GGGUCAACAUCUUUUACAU | AUGUAAAAGAUGUUGACCC | [2367-2385] | | — | |
| 14 | Human | GAAGGGUCAACAUCUUUUA | UAAAAGAUGUUGACCCUUC | [2364-2382] | | — | |
| 15 | Human | CUGGAAGGGUCAACAUCUU | AAGAUGUUGACCCUUCCAG | [2361-2379] | | — | |
| 16 | Human | CCAGAGUGCUGGGAUUACA | UGUAAUCCCAGCACUCUGG | [2321-2339] | | — | |
| 17 | Human | GAUGGGGUCUCACAGUGUU | AACACUGUGAGACCCCAUC | [2249-2267] | | — | |
| 18 | Human | GCCAACUUUGCAUGUUUU | AAAACAUGCAAAGUUGGC | [2225-2243] | | — | |
| 19 | Human | CCAUGGCCAGCCAACUUUU | AAAAGUUGGCUGGCCAUGG | [2216-2234] | | — | |

| No. | Source | Sense | AntiSense | gi13097806 gbBC003596.1 (*Homo sapiens*) | gi2689466 gbU48957.1 U48957 (*Macaca fascicularis*) | gi53575emb X01237.1MMP53R (Mouse mRNA) | gi4996229dbjAB020761.1 (*Canis familiaris*) |
|---|---|---|---|---|---|---|---|
| 20 | Human | AGACCCAGGUCCAGAUGAA | UUCAUCUGGACCUGGGUCU | [288-306] | | — | |
| 21 | Human, mouse | CCAUCAUCACACUGGAAGA | UCUUCCAGUGUGAUGAUGG | [878-896] | | [906-924] | |
| 22 | Human, mouse | CAUCACACUGGAAGACUCC | GGAGUCUUCCAGUGUGAUG | [882-900] | | [910-928] | |
| 23 | Human, mouse | CAUCAUCACACUGGAAGAC | GUCUUCCAGUGUGAUGAUG | [879-897] | | [907-925] | |
| 24 | Human, mouse | ACCAUCAUCACACUGGAAG | CUUCCAGUGUGAUGAUGGU | [877-895] | | [905-923] | |
| 25 | Human, mouse | AUCAUCACACUGGAAGACU | AGUCUUCCAGUGUGAUGAU | [880-898] | | [908-926] | |
| 26 | Human, mouse | CACUGGAAGACUCCAGUGG | CCACUGGAGUCUUCCAGUG | [887-905] | | [915-933] | |
| 27 | Human, cynomoglus, mouse | ACACUGGAAGACUCCAGUG | CACUGGAGUCUUCCAGUGU | [886-904] | [766-784] | [914-932] | |
| 28 | Human, cynomoglus, mouse | UCACACUGGAAGACUCCAG | CUGGAGUCUUCCAGUGUGA | [884-902] | [764-782] | [912-930] | |
| 29 | Human, cynomoglus, mouse | AUCACACUGGAAGACUCCA | UGGAGUCUUCCAGUGUGAU | [883-901] | [763-781] | [911-929] | |
| 30 | Human, cynomoglus, mouse | CACAGCACAUGACGGAGGU | ACCUCCGUCAUGUGCUGUG | [617-635] | [497-515] | [645-663] | |
| 31 | Human, cynomoglus, mouse | CACUGGAAGACUCCAGUGG | CCACUGGAGUCUUCCAGUG | [887-905] | [767-785] | [915-933] | |
| 32 | Human, cynomoglus, mouse | UCACAGCACAUGACGGAGG | CCUCCGUCAUGUGCUGUGA | [616-634] | [496-514] | [644-662] | |
| 33 | Human, cynomoglus, mouse | GUCACAGCACAUGACGGAG | CUCCGUCAUGUGCUGUGAC | [615-633] | [495-513] | [643-661] | |
| 34 | Human, cynomoglus, dog | CCAUCCACUACAACUACAU | AUGUAGUUGUAGUGGAUGG | [812-830] | [692-710] | [702-720] | |
| 35 | Human, cynomoglus, dog | CCACCAUCCACUACAACUA | UAGUUGUAGUGGAUGGUGG | [809-827] | [689-707] | | [699-717] |
| 36 | Human, cynomoglus, dog | GAAUAUUUCACCCUUCAGA | UCUGAAGGGUGAAAUAUUC | [1096-1114] | [976-994] | | [986-1004] |
| 37 | Human, cynomoglus, dog | CGAGUGGAAGGAAAUUUGC | GCAAAUUUCCUUCCACUCG | [706-724] | [586-604] | | [596-614] |
| 38 | Human, cynomoglus, dog | GAGAAUAUUUCACCCUUCA | UGAAGGGUGAAAUAUUCUC | [1094-1112] | [974-992] | | [984-1002] |
| 39 | Human, cynomoglus, dog | CUACAUGUGUAACAGUUCC | GGAACUGUUACACAUGUAG | [825-843] | [705-723] | | [715-733] |

TABLE B-continued

| No. | Source | Sense | AntiSense | gi13097806 gbBC003596.1 (Homo sapiens) | gi2689466 gbU48957.1 U48957 (Macaca fascicularis) | gi53575emb X01237. 1MMP53R (Mouse mRNA) | gi4996229 dbjAB020761.1 (Canis familiaris) |
|---|---|---|---|---|---|---|---|
| 40 | Human, cynomoglus, dog | AACUACAUGUGUAACAGUU | AACUGUUACACAUGUAGUU | [823-841] | [703-721] | | [713-731] |
| 41 | Human, cynomoglus, dog | CAACUACAUGUGUAACAGU | ACUGUUACACAUGUAGUUG | [822-840] | [702-720] | | [712-730] |
| 42 | Human, cynomoglus, dog | CACUACAACUACAUGUGUA | UACACAUGUAGUUGUAGUG | [817-835] | [697-715] | | [707-725] |
| 43 | Human, cynomoglus, dog | CCACUACAACUACAUGUGU | ACACAUGUAGUUGUAGUGG | [816-834] | [696-714] | | [706-724] |
| 44 | Human, cynomoglus, dog | GACAGAAACACUUUUCGAC | GUCGAAAAGUGUUUCUGUC | [742-760] | [622-640] | | [632-650] |
| 45 | Human, cynomoglus, dog | GGAGAAUAUUUCACCCUUC | GAAGGGUGAAAUAUUCUCC | [1093-1111] | [973-991] | | [983-1001] |
| 46 | Human, cynomoglus, dog | GUGUAACAGUUCCUGCAUG | CAUGCAGGAACUGUUACAC | [831-849] | [711-729] | | [721-739] |
| 47 | Human, cynomoglus, dog | ACAACUACAUGUGUAACAG | CUGUUACACAUGUAGUUGU | [821-839] | [701-719] | | ]711-729] |
| 48 | Human, cynomoglus, dog | ACUACAACUACAUGUGUAA | UUACACAUGUAGUUGUAGU | [818-836] | [698-716] | | [708-726] |
| 49 | Human, cynomoglus, dog | ACCAUCCACUACAACUACA | UGUAGUUGUAGUGGAUGGU | [811-829] | [691-709] | | [701-719] |
| 50 | Human, cynomoglus, dog | ACCACCAUCCACUACAACU | AGUUGUAGUGGAUGGUGGU | [808-826] | [688-706] | | [698-716] |
| 51 | Human, cynomoglus, dog | UACCACCAUCCACUACAAC | GUUGUAGUGGAUGGUGGUA | [807-825] | [687-705] | | [697-715] |
| 52 | Human, cynomoglus, dog | ACAGAAACACUUUUCGACA | UGUCGAAAAGUGUUUCUGU | [743-761] | [623-641] | | [633-651] |
| 53 | Human, cynomoglus, dog | GAGUGGAAGGAAAUUUGCG | CGCAAAUUUCCUUCCACUC | [707-725] | [587-605] | | [597-615] |
| 54 | Human, cynomoglus, dog | AUAUUUCACCCUUCAGAUC | GAUCUGAAGGGUGAAAUAU | [1098-1116] | [978-996] | | [988-1006] |
| 55 | Human, cynomoglus, dog | AAUAUUUCACCCUUCAGAU | AUCUGAAGGGUGAAAUAUU | [1097-1115] | [977-995] | | [987-1005] |
| 56 | Human, cynomoglus, dog | AGAAUAUUUCACCCUUCAG | CUGAAGGGUGAAAUAUUCU | [1095-1113] | [975-993] | | [985-1003] |
| 57 | Human, cynomoglus, dog | UGGAGAAUAUUUCACCCUU | AAGGGUGAAAUAUUCUCCA | [1092-1110] | [972-990] | | [982-1000] |

TABLE B-continued

| No. | Source | Sense | AntiSense | gi13097806 gbBC003596.1 (Homo sapiens) | gi2689466 gbU48957.1 U48957 (Macaca fascicularis) | gi53575emb X01237. 1MMP53R (Mouse mRNA) | gi4996229 dbjAB020761.1 (Canis familiaris) |
|---|---|---|---|---|---|---|---|
| 58 | Human, cynomoglus, dog | ACAUGUGUAACAGUUCCUG | CAGGAACUGUUACACAUGU | [827-845] | [707-725] | | [717-735] |
| 59 | Human, cynomoglus, dog | UACAACUACAUGUGUAACA | UGUUACACAUGUAGUUGUA | [820-838] | [700-718] | | [710-728] |
| 60 | Human, cynomoglus, dog | CUACAACUACAUGUGUAAC | GUUACACAUGUAGUUGUAG | [819-837] | [699-717] | | [709-727] |
| 61 | Human, cynomoglus, dog | UCCACUACAACUACAUGUG | CACAUGUAGUUGUAGUGGA | [815-833] | [695-713] | | [705-723] |
| 62 | Human, cynomoglus, dog | AUCCACUACAACUACAUGU | ACAUGUAGUUGUAGUGGAU | [814-832] | [694-712] | | [704-722] |
| 63 | Human, cynomoglus, dog | CAUCCACUACAACUACAUG | CAUGUAGUUGUAGUGGAUG | [813-831] | [693-711] | | [703-721] |
| 64 | Human, cynomoglus, dog | CACCAUCCACUACAACUAC | GUAGUUGUAGUGGAUGGUG | [810-828] | [690-708] | | [700-718] |
| 65 | Human, cynomoglus, dog | UGUGUAACAGUUCCUGCAU | AUGCAGGAACUGUUACACA | [830-848] | [710-728] | | [720-738] |
| 66 | Human, cynomoglus, dog | CAUGUGUAACAGUUCCUGC | GCAGGAACUGUUACACAUG | [828-846] | [708-726] | | [718-736] |
| 67 | Human, cynomoglus, dog | UACAUGUGUAACAGUUCCU | AGGAACUGUUACACAUGUA | [826-844] | [706-724] | | [716-734] |
| 68 | Human, cynomoglus, dog | ACUACAUGUGUAACAGUUC | GAACUGUUACACAUGUAGU | [824-842] | [704-722] | | [714-732] |
| 69 | Human, cynomoglus, dog | AUCCGAGUGGAAGGAAAUU | AAUUUCCUUCCACUCGGAU | [703-721] | [583-601] | | [593-611] |
| 70 | Human, cynomoglus, dog | UCACUCCAGCCACCUGAAG | CUUCAGGUGGCUGGAGUGA | [1212-1230] | [1092-1110] | | [1102-1120] |
| 71 | Human, cynomoglus, dog | CUCACUCCAGCCACCUGAA | UUCAGGUGGCUGGAGUGAG | [1211-1229] | [1091-1109] | | [1101-1119] |

Note that in the above Table B, the sense strands of siRNAs 1-71 have SEQ ID NOS: 49-119 respectively, and the antisense strands of siRNAs 1-71 have SEQ ID NOS: 120-190 respectively.

Table C1 below shows 63 additional 21-mer siRNAs which have been generated by the proprietary algorithms.

Table C2 below shows 35 additional 23-mer siRNAs which have been generated by the proprietary algorithms.

TABLE C

| No. | Source | Sense SiRNA | AntiSense SiRNA | gi13097806 gbBC003596.1 (Homo sapiens) | gi2689466 gbU48957.1 U48957 (Macaca fascicularis) | gi53575emb X01237.1M MP53R (Mouse mRNA) | gi4996229 dbj AB020761.1 (Canis familiaris) |
|---|---|---|---|---|---|---|---|
| 1 | Human | GGAAGAGAAUCUCCGCAAGAA | UUCUUGCGGAGAUUCUCUUCC | [975-995] | — | — | — |
| 2 | Human | GUACCACCAUCCACUACAACU | AGUUGUAGUGGAUGGUGGUAC | [806-826] | [686-706] | [835-852] | [697-716] |
| 3 | Human | GGACGAUAUUGAACAAUGGUU | AACCAUUGUUCAAUAUCGUCC | [261-281] | — | — | — |
| 4 | Human | CCAGCCACCUGAAGUCCAAAA | UUUUGGACUUCAGGUGGCUGG | [1217-1237] | [1097-1115] | — | [1107-1120] |
| 5 | Human | GAGAAUAUUUCACCCUUCAGA | UCUGAAGGUGAAAUAUUCUC | [1094-1114] | [974-994] | [1122-1137] | [984-1004] |
| 6 | Human | AGAAACCACUGGAUGGAGAAU | AUUCUCCAUCCAGUGGUUUCU | [1079-1099] | [959-979] | — | — |
| 7 | Human | CUACUGGGACGAACAGCUUU | AAAGCUGUUCCGUCCCAGUAG | [910-930] | [790-810] | — | — |
| 8 | Human | AGACUCCAGUGGUAAUCUACU | AGUAGAUUACCACUGGAGUCU | [894-914] | [774-794] | [922-933] | [784-795] |
| 9 | Human | CUGGAAGACUCCAGUGGUAAU | AUUACCACUGGAGUCUUCCAG | [889-909] | [769-789] | [917-933] | [779-795] |
| 10 | Human | GAAACUACUUCCUGAAAACAA | UUGUUUUCAGGAAGUAGUUUC | [189-209] | [69-87] | [235-247] | [122-135] |
| 11 | Human | GGAAACUACUUCCUGAAAACA | UGUUUUCAGGAAGUAGUUUCC | [188-208] | [68-87] | [234-247] | [122-134] |
| 12 | Human | AAACACUUUCGACAUAGUGU | ACACUAUGUCGAAAGUGUUU | [747-767] | [627-647] | — | [637-657] |
| 13 | Human | GGAGUAUUUGGAUGACAGAAA | UUUCUGUCAUCCAAAUACUCC | [729-749] | [609-629] | — | — |
| 14 | Human | UCAGACCUAUGGAAACUACUU | AAGUAGUUUCCAUAGGUCUGA | [178-198] | [58-78] | [231-244] | — |
| 15 | Human | CCAUGGCCAUCUACAAGCAGU | ACUGCUUGUAGAUGCCCAUGG | [596-616] | [476-496] | [624-640] | [485-495] |
| 16 | Human | CCAAGUCUGUGACUUGCACGU | ACGUGCAAGUCACAGACUUGG | [476-496] | [356-376] | — | — |
| 17 | Human | GGACAGCCAAGUCUGUGACUU | AAGUCACAGACUUGGCUGUCC | [470-490] | [352-370] | [498-513] | [357-377] |
| 18 | Human | CCCUCCUUCUCCCUUUUUAUA | UAUAAAAAGGGAGAAGGAGGG | [2421-2441] | — | [1721-1731] | — |
| 19 | Human, cynomoglus, dog | CCAUCCACUACAACUACAUGU | ACAUGUAGUUGUAGUGGAUGG | [812-832] | [692-712] | [840-860] | [702-722] |
| 20 | Human, cynomoglus, dog | CCACCAUCCACUACAACUACA | UGUAGUUGUAGUGGAUGGUGG | [809-829] | [689-709] | [837-857] | [699-719] |
| 21 | Human, cynomoglus, dog | GAGAAUAUUUCACCCUUCAGA | UCUGAAGGGUGAAAUAUUCUC | [1094-1114] | [974-994] | | [984-1004] |
| 22 | Human, cynomoglus, dog | GGAGAAUAUUUCACCCUUCAG | CUGAAGGGUGAAAUAUUCUCC | [1093-1113] | [973-993] | | [983-1003] |
| 23 | Human, cynomoglus, dog | CUACAUGUGUAACAGUUCCUG | CAGGAACUGUUACACAUGUAG | [825-845] | [705-725] | | [715-735] |
| 24 | Human, cynomoglus, dog | ACAACUACAUGUGUAACAGUU | AACUGUUACACAUGUAGUUGU | [821-841] | [701-721] | | [711-731] |
| 25 | Human, cynomoglus, dog | CCACUACAACUACAUGUGUAA | UUACACAUGUAGUUGUAGUGG | [816-836] | [696-716] | | [706-726] |
| 26 | Human, cynomoglus, dog | CACCAUCCACUACAACUACAU | AUGUAGUUGUAGUGGAUGGUG | [810-830] | [690-710] | | [700-720] |

TABLE C-continued

| No. | Source | Sense SIRNA | AntiSense SiRNA | gi13097806 gbBC003596.1 (*Homo sapiens*) | gi2689466 gbU48957.1 U48957 (*Macaca fascicularis*) | gi53575emb X01237.1M MP53R (Mouse mRNA) | gi4996229 dbj AB020761.1 (*Canis familiaris*) |
|---|---|---|---|---|---|---|---|
| 27 | Human, cynomoglus, dog | GAAUAUUUCACCCUUCAGAUC | GAUCUGAAGGGUGAAAUAUUC | [1096-11161] | [976-996] | | [986-1006] |
| 28 | Human, cynomoglus, dog | AGAAUAUUUCACCCUUCAGAU | AUCUGAAGGGUGAAAUAUUCU | [1095-1115] | [975-995] | | [985-1005] |
| 29 | Human, cynomoglus, dog | UACCACCAUCCACUACAACUA | UAGUUGUAGUGGAUGGUGGUA | [807-827] | [687-707] | | [697-717] |
| 30 | Human, cynomoglus, dog | GAUGGAGAAUAUUUCACCCUU | AAGGGUGAAAUAUUCUCCAUC | [1090-1110] | [970-990] | | [980-1000] |
| 31 | Human, cynomoglus, dog | CCGAGUGGAAGGAAAUUUGCG | CGCAAAUUUCCUUCCAGUCGG | [705-725] | [585-605] | | [595-615] |
| 32 | Human, cynomoglus, dog | AACUACAUGUGUAACAGUUCC | GGAACUGUUACACAUGUAGUU | [823-843] | [703-723] | | [713-733] |
| 33 | Human, cynomoglus, dog | CAACUACAUGUGUAACAGUUC | GAACUGUUACACAUGUAGUUG | [822-842] | [702-722] | | [712-732] |
| 34 | Human, cynomoglus, dog | ACUACAACUACAUGUGUAACA | UGUUACACAUGUAGUUGUAGU | [8 18-838] | [698-718] | | [708-728] |
| 35 | Human, cynomoglus, dog | CACUACAACUACAUGUGUAAC | GUUACACAUGUAGUUGUAGUG | [817-8371] | [697-717] | | [707-727] |
| 36 | Human, cynomoglus, dog | UCCACUACAACUACAUGUGUA | UACACAUGUAGUUGUAGUGGA | [815-835] | [695-715] | | [705-725] |
| 37 | Human, cynomoglus, dog | CAUCCACUACAACUACAUGUG | CACAUGUAGUUGUAGUGGAUG | [813-833] | [693-713] | | [703-723] |
| 38 | Human, cynomoglus, dog | ACCAUCCACUACAACUACAUG | CAUGUAGUUGUAGUGGAUGGU | [811-831] | [691-711] | | [701-721] |
| 39 | Human, cynomoglus, dog | UGGAGAAUAUUUCACCCUUCA | UGAAGGGUGAAAUAUUCUCCA | [1092-1112] | [972-992] | | [982-1002] |
| 40 | Human, cynomoglus, dog | AUGUGUAACAGUUCCUGCAUG | CAUGCAGGAACUGUUACACAU | [829-849] | [709-729] | | [719-739] |
| 41 | Human, cynomoglus, dog | CAUGUGUAACAGUUCCUGCAU | AUGCAGGAACUGUUACACAUG | [828-848] | [708-728] | | [718-738] |
| 42 | Human, cynomoglus, dog | UACAACUACAUGUGUAACAGU | ACUGUUACACAUGUAGUUGUA | [820-840] | [700-720] | | [710-730] |
| 43 | Human, cynomoglus, dog | CUACAACUACAUGUGUAACAG | CUGUUACACAUGUAGUUGUAG | [819-839] | [699-719] | | [709-729] |
| 44 | Human, cynomoglus, dog | AUCCACUACAACUACAUGUGU | ACACAUGUAGUUGUAGUGGAU | [814-834] | [694-714] | | [704-724] |

TABLE C-continued

| No. | Source | Sense SiRNA | AntiSense SiRNA | gi13097806 gbBC003596.1 (Homo sapiens) | gi2689466 gbU48957.1 U48957 (Macaca fascicularis) | gi53575emb X01237.1M MP53R (Mouse mRNA) | gi4996229 dbj AB020761.1 (Canis familiaris) |
|---|---|---|---|---|---|---|---|
| 45 | Human, cynomoglus, dog | ACCACCAUCCACUACAACUAC | GUAGUUGUAGUGGAUGGUGGU | [808-828] | [688-708] | | [698-718] |
| 46 | Human, cynomoglus, dog | AAUAUUUCACCCUUCAGAUCC | GGAUCUGAAGGGUGAAAUAUU | [1097-1117] | [977-997] | | [987-1007] |
| 47 | Human, cynomoglus, dog | ACUACAUGUGUAACAGUUCCU | AGGAACUGUUACACAUGUAGU | [824-844] | [704-724] | | [714-734] |
| 48 | Human, cynomoglus, dog | AUGGAGAAUAUUUCACCCUUC | GAAGGGUGAAAUAUUCUCCAU | [1091-1111] | [971-991] | | [981-1001] |
| 49 | Human, cynomoglus, dog | UGUGUAACAGUUCCUGCAUGG | CCAUGCAGGAACUGUUACACA | [830-850] | [710-730] | | [720-740] |
| 50 | Human, cynomoglus, dog | UCCGAGUGGAAGGAAAUUUGC | GCAAAUUUCCUUCCACUCGGA | [704-724] | [584-604] | | [594-614] |
| 51 | Human, cynomoglus, dog | AUCCGAGUGGAAGGAAAUUUG | CAAAUUUCCUUCCACUCGGAU | [703-723] | [583-603] | | [593-613] |
| 52 | Human, cynomoglus, mouse | UCACACUGGAAGACUCCAGUG | CACUGGAGUCUUCCAGUGUGA | [884-904] | [764-784] | [912-932] | |
| 53 | Human, cynomoglus, mouse | AUCACACUGGAAGACUCCAGU | ACUGGAGUCUUCCAGUGUGAU | [883-903] | [763-783] | [911-931] | |
| 54 | Human, cynomoglus, mouse | CACACUGGAAGACUCCAGUGG | CCACUGGAGUCUUCCAGUGUG | [885-905] | [765-785] | [913-933] | |
| 55 | Human, mouse | UCAUCACACUGGAAGACUCCA | UGGAGUCUUCCAGUGUGAUGA | [881-901] | | [909-929] | |
| 56 | Human, mouse | CCAUCAUCACACUGGAAGACU | AGUCUUCCAGUGUGAUGAUGG | [878-898] | | [906-926] | |
| 57 | Human, mouse | CAUCACACUGGAAGACUCCAG | CUGGAGUCUUCCAGUGUGAUG | [882-902] | | [910-930] | |
| 58 | Human, mouse | CAUCAUCACACUGGAAGACUC | GAGUCUUCCAGUGUGAUGAUG | [879-899] | | [907-927] | |
| 59 | Human, mouse | ACCAUCAUCACACUGGAAGAC | GUCUUCCAGUGUGAUGAUGGU | [877-897] | | [905-925] | |
| 60 | Human, mouse | UCACACUGGAAGACUCCAGUG | CACUGGAGUCUUCCAGUGUGA | [8 84-904] | | [912-932] | |
| 61 | Human, mouse | AUCACACUGGAAGACUCCAGU | ACUGGAGUCUUCCAGUGUGAU | [883-903] | | [911-931] | |
| 62 | Human, mouse | AUCAUCACACUGGAAGACUCC | GGAGUCUUCCAGUGUGAUGAU | [880-900] | | [908-928] | |
| 63 | Human, mouse | CACACUGGAAGACUCCAGUGG | CCACUGGAGUCUUCCAGUGUG | [885-905] | | [913-933] | |

TABLE C2

| siRNA name | Sense strand | AS strand | Other Species | Human-120407067; ORF:252-1433 | Human-8400737; ORF:252-1433 |
|---|---|---|---|---|---|
| 1 | GGAGAAUAUUUCACCCUUCACAU | AUCUGAAGGGUGAAAUAUUCUCC | MF, CF | 1224-1246 | 1224-1246 |
| 2 | UGGAGAAUAUUUCACCCUUCAGA | UCUGAAGGGUGAAAUAUUCUCCA | MF, CF | 1223-1245 | 1223-1245 |
| 3 | AUGGAGAAUAUUUCACCCUUCAG | CUGAAGGGUGAAAUAUUCUCCAU | MF, CF | 1222-1244 | 1222-1244 |
| 4 | GAUGGAGAAUAUUUCACCCUUCA | UGAAGGGUGAAAUAUUCUCCAUC | MF, CF | 1221-1243 | 1221-1243 |
| 5 | GAGAAUAUUUCACCCUUCAGAUC | GAUCUGAAGGGUGAAAUAUUCUC | MF, CF | 1225-1247 | 1225-1247 |
| 6 | AGUGUGGUGGUGCCCUAUGAGCC | GGCUCAUAGGGCACCACCACACU | MF | 894-916 | 894-916 |
| 7 | UAGUGUGGUGGUGCCCUAUGAGC | GCUCAUAGGGCACCACCACACUA | MF | 893-915 | 893-915 |
| 8 | AUAGUGUGGUGGUGCCCUAUGAG | CUCAUAGGGCACCACCACACUAU | MF | 892-914 | 892-914 |
| 9 | CAUAGUGUGGUGGUGCCCUAUGA | UCAUAGGGCACCACCACACUAUG | MF | 891-913 | 891-913 |
| 10 | GUGUGGUGGUGCCCUAUGAGCCG | CGGCUCAUAGGGCACCACCACAC | MF | 895-917 | 895-917 |
| 11 | UGACAGAAACACUUUUCGACAUA | UAUGUCGAAAAGUGUUUCUGUCA | MF, CF, Sus scrofa | 872-894 | 872-894 |
| 12 | AUGACAGAAACACUUUUCGACAU | AUGUCGAAAAGUGUUUCUGUCAU | MF, CF, Sus scrofa | 871-893 | 871-893 |
| 13 | GAUGACAGAAACACUUUUCGACA | UGUCGAAAAGUGUUUCUGUCAUC | MF, CF, Sus scrofa | 870-892 | 870-892 |
| 14 | GGAUGACAGAAACACUUUUCGAC | GUCGAAAAGUGUUUCUGUCAUCC | MF, CF, Sus scrofa | 869-891 | 869-891 |
| 15 | GACAGAAACACUUUUCGACAUAG | CUAUGUCGAAAAGUGUUUCUGUC | MF, CF, Sus scrofa | 873-895 | 873-895 |
| 16 | UCCGAGUGGAAGGAAAUUUGCGU | ACGCAAAUUUCCUUCCACUCGGA | MF, CF | 835-857 | 835-857 |
| 17 | AUCCGAGUGGAAGGAAAUUUGCG | CGCAAAUUUCCUUCCACUCGGAU | MF, CF | 834-856 | 834-856 |
| 18 | UAUCCGAGUGGAAGGAAAUUUGC | GCAAAUUUCCUUCCACUCGGAUA | MF, CF | 833-855 | 833-855 |
| 19 | UUAUCCGAGUGGAAGGAAAUUUG | CAAAUUUCCUUCCACUCGGAUAA | MF, CF | 832-854 | 832-854 |
| 20 | CCGAGUGGAAGGAAAUUUGCGUG | CACGCAAAUUUCCUUCCACUCGG | MF, CF | 836-858 | 836-858 |
| 21 | AUCAUCACACUGGAAGACUCCAG | CUGGAGUCUUCCAGUGUGAUGAU | Mus musculus, O. cuniculus | 1011-1033 | 1011-1033 |
| 22 | CAUCAUCACACUGGAAGACUCCA | UGGAGUCUUCCAGUGUGAUGAUG | Mus musculus, O. cuniculus | 1010-1032 | 1010-1032 |
| 23 | CCAUCAUCACACUGGAAGACUCC | GGAGUCUUCCAGUGUGAUGAUGG | Mus musculus, O. cuniculus | 1009-1032 | 1009-1032 |
| 24 | ACCAUCAUCACACUGGAAGACUC | GAGUCUUCCAGUGUGAUGAUGGU | Mus musculus, O. cuniculus | 1008-1031 | 1008-1031 |
| 25 | UCAUCACACUGGAAGACUCCAGU | ACUGGAGUCUUCCAGUGUGAUGA | Mus musculus, O. cuniculus | 1012-1034 | 1012-1034 |
| 26 | UCCCAAGCAAUGGAUGAUUUGAU | AUCAAAUCAUCCAUUGCUUGGGA | | 360-382 | 360-382 |
| 27 | GUCCCAAGCAAUGGAUGAUUUGA | UCAAAUCAUCCAUUGCUUGGGAC | | 359-381 | 359-381 |
| 28 | CGUCCCAAGCAAUGGAUGAUUUG | CAAAUCAUCCAUUGCUUGGGACG | | 358-380 | 358-380 |
| 29 | CCGUCCCAAGCAAUGGAUGAUUU | AAAUCAUCCAUUGCUUGGGACGG | | 357-379 | 357-379 |
| 30 | CCCAAGCAAUGGAUGAUUUGAUG | CAUCAAAUCAUCCAUUGCUUGGG | | 361-383 | 361-383 |
| 31 | UCAGACCUAUGGAAACUACUUCC | GGAAGUAGUUUCCAUAGGUCUGA | MF | 309-331 | 309-331 |
| 32 | UUCAGACCUAUGGAAACUACUUC | GAAGUAGUUUCCAUAGGUCUGAA | MF | 308-330 | 30 8-330 |
| 33 | UUUCAGACCUAUGGAAACUACUU | AAGUAGUUUCCAUAGGUCUGAAA | MF | 307-329 | 307-329 |

TABLE C2-continued

| siRNA name | Sense strand | AS strand | Other Species | Human-120407067; ORF:252-1433 | Human-8400737; ORF:252-1433 |
|---|---|---|---|---|---|
| 34 | UUUUCAGACCUAUGGAAACUACU | AGUAGUUUCCAUAGGUCUGAAAA | MF | 306-328 | 306-328 |
| 35 | CAGACCUAUGGAAACUACUUCCU | AGGAACUAGUUUCCAUAGGUCUG | MF | 310-332 | 310-332 |

*Macaca fascicularis* = MF
*Canis familiaris* = CF

Note that in the above Table C the sense strands of siRNAs 1-63 have SEQ ID NOS: 191-253 respectively, and the antisense strands of siRNAs 1-63 have SEQ ID NOS: 254-316 respectively.

Note that in the above Table C2, the sense strands of siRNAs 1-35 have SEQ ID NOS: 319-353 respectively, and the antisense strands of siRNAs 1-35 have SEQ ID NOS: 354-388 respectively.

Example 2

Testing the siRNA Compounds for Anti-p53 Activity

Protocols
I. Preparation of the siRNAs (Double-Stranded Oligonucleotides)

Lyophilized oligonucleotides were dissolved in RNAse free distilled water to produce a final concentration of 100 uM. The diluted oligonucleotides were kept at room temperature for 15 min and immediately frozen in liquid nitrogen.

The oligonucleotides were stored at −80° C. and diluted before use with PBS.

II. Transfection of siRNA in Human Cells with Lipofectamine2000 Reagent:

$2 \times 10^5$ p53-wt HCT116 or SW480 cells were seeded per well in 6 wells plate. 24 h subsequently, cells were transfected with p53 oligonucleotides using lipofectamine2000 reagent (obtained from Invitrogen).

The following procedure was performed:
1. Before transfection, the cell medium was replaced by 1500 ul fresh medium without antibiotics.
2. In a sterile, plastic tube, Lipofectamine2000 reagent (the amount is calculated according to 5 ul per well) was added to 250 ul serum-free medium, and incubated for 5 min at room temperature.
3. In another tube the human anti-p53 oligonucleotides (varying amounts to fit the desired final concentration per well) were added to 250 ul serum-free medium.
4. Lipofectamine2000 complex was combined with the p53 oligonucleotide solution and incubated for 20 min at room temperature.
5. The resulting mixture was added dropwise to the cells, and the cells were incubated at 37° C.
6. SW480 cells: 48 hr after transfection the cells were harvested and proteins were extracted using RIPA buffer.
7. HCT116 cells:
   40 h after transfection, 5 Fu (Sigma) was added to cells to produce a final concentration of 25 ug/ml. 48 h after cells transfection (8 h after 5 Fu treatment), the cells were harvested and proteins were extracted using RIPA buffer.
8. p53 expression was determined by Western Blot analysis using monoclonal antibody (Do-1 clone, Santa Cruz). For normalization, blots were examined for Tubulin expression.

III Co-Transfection of Mouse p53 Gene and Mouse p53 Oligonucleotides into PC3 Cells Using Lipofectamine2000 Reagent:

$2 \times 10^5$ p53-null PC3 cells were seeded per well in 6 wells plate. 24 h subsequently, cells were Co-transfected with mouse p53 gene and GFP gene and mouse p53 oligonucleotides using lipofectamine2000 reagent (Invitrogen). The following procedure was performed:
1. Before transfection cell medium was replaced by 1500 ul fresh medium without antibiotics.
2. In sterile, plastic tube, Lipofectamine2000 reagent (5 ul per well) was added to 250 ul serum-free medium, and incubated for 5 min at room temperature.
3. In another tube 4 ug DNA (p53 gene:GFP gene, 10:1) and human p53 oligonucleotides were added to 250 ul serum free medium.
4. Lipofectamine2000 complex was combined with p53 oligonucleotides solution and incubated for 20 min at room temperature.
5. The mixture solution was added dropwise to the cells, and cells were incubated at 37° C.
6. 48 h alter transfection, cells were harvested and proteins were extracted using RIPA buffer.
7. p53 expression was determined by Western Blot analysis using monoclonal antibody (Clone240, Chemicon). For normalization, blots were examined for GFP expression.

Results:
A. Human p53 Oligonucleotides:

TABLE D

| | | | | Results of Test | |
|---|---|---|---|---|---|
| Number | oligo | species | source | SW480 | HCT116 |
| 2 | Hu2' | human | literature | (−) | (+) |
| 3 | QHMon1 | human, monkey | Proprietary | (++) | (+++) |
| 4 | QHMon2 | human, monkey | Proprietary | (−) | Not tested |
| 5 | QH1 | human | Proprietary | (+++) | (+++) |
| 6 | QH2 | human | Proprietary | (−) | Not tested |
| 13 | A17 | human, mouse | Proprietary | (−) | Not tested |
| 14 | E2 | human, mouse, rat | Proprietary | (+) | Not tested |

TABLE D-continued

| Number | oligo | species | source | Results of Test SW480 | HCT116 |
|---|---|---|---|---|---|
| 15 | E6 | human, mouse, rat | Proprietary | (−) | Not tested |
| 16 | B1 | human, mouse, rat | Proprietary | (−) | Not tested |
| 17 | B2 | human, mouse, rat | Proprietary | (−) | Not tested |
| 18 | C1 | human, monkey, mouse | Proprietary | (−) | Not tested |
| 19 | F2 | human, monkey, dog | Proprietary | (−) | Not tested |
| 20 | F3 | human, monkey, dog | Proprietary | (+++) | (+++) |
| 21 | G1 | human, monkey, dog | Proprietary | (+++) | Not tested |
| 22 | H2 | human, monkey, dog | Proprietary | (+) | Not tested |
| 23 | I5 | human, monkey, dog | Proprietary | (+++) | Not tested |

Note:
The numbers in Table D correspond to the numbers used in Table A, where the sense strands of siRNAs 1-23 have SEQ ID NOS: 3-25 respectively, and the antisense strands of siRNAs 1-23 have SEQ ID NOS: 26-48 respectively.
As shown in Table D, four human oligonucleotides were tested in two systems SW480 and HCT116, according to Protocols II above. Representative results (Western Blot) on which the Results of Test was based are shown in FIG. 3.

TABLE E

B. Mouse p53 oligonucleotides:

| | oligo | species | source | Results of Test PC3 null cells/exogenous mouse p53 |
|---|---|---|---|---|
| 1 | Mo3 | mouse | literature | (+++) |
| 7 | QM1 | mouse | Proprietary | (−) |
| 8 | QM2 | mouse | Proprietary | (−) |
| 9 | QM3 | mouse | Proprietary | (−) |
| 10 | QM6 | mouse | Proprietary | (−) |
| 11 | QM4 | mouse, rat | Proprietary | (+++) |
| 12 | QM5 | mouse, rat | Proprietary | (+++) |
| 13 | A17 | human, mouse | Proprietary | (−) |
| 14 | E2 | human, mouse, rat | Proprietary | (++) |
| 15 | E6 | human, mouse, rat | Proprietary | (−) |
| 16 | B1 | human, monkey, mouse | Proprietary | (−) |
| 17 | B2 | human, monkey, mouse | Proprietary | (++) |
| 18 | C1 | human, monkey, mouse | Proprietary | (++) |
| 19 | G1 | human, monkey, dog | Proprietary | (++) |
| 20 | F3 | human, monkey, dog | Proprietary | (+++) |
| 21 | I5 | human, monkey, dog | Proprietary | (−) |
| 22 | QHMon1 | human, monkey | Proprietary | (++) |

Note:
The numbers in Table E (as for Table D) correspond to the numbers used in Table A, where the sense strands of siRNAs 1-23 have SEQ ID NOS: 3-25 respectively, and the antisense strands of siRNAs 1-23 have SEQ ID NOS: 26-48 respectively. Representatives of the Western Blot results on which the Results of Test was based are shown in FIG. 4.

Example 3

Distribution of Cy3-PTEN siRNA in the Cochlea Following Local Application to the Round Window of the Ear A solution of 1 µg/100 µl of Cy3-PTEN siRNA (total of 0.3-0.4 µg) PBS was applied to the round window of chinchillas. The Cy3-labelled cells within the treated cochlea were analyzed 24-48 hours post siRNA round window application after sacrifice of the chinchillas. The pattern of labeling within the cochlea was similar following 24 h and 48 h and includes labeling in the basal turn of cochlea, in the middle turn of cochlea and in the apical turn of cochlea. Application of Cy3-PTEN siRNA onto scala tympani revealed labelling mainly in the basal turn of the cochlea and the middle turn of the cochlea. The Cy3 signal was persistance to up to 15 days after the application of the Cy3-PTEN siRNA. These results indicate for the first time that local application of siRNA molecules within the round window leads to significant penetration of the siRNA molecules to the basal, middle and apical turns of the cochlea.

Example 4

The Effect of p53 siRNA Treatment on Carboplatin-Induced Hair Cell Death in the Cochlea of Chinchilla Eight Chinchillas were pre-treated by direct administration of p53 siRNA in saline (QM5 molecule in Table A, 1, 10 and 30 µg) to the left ear of each animal. Saline was given to the right ear of each animal as placebo. Two days following the administration of the p53 siRNA, the animals were treated with carboplatin (75 mg/kg ip). After sacrifice of the chinchillas (two weeks post carboplatin treatment) the % of dead cells of inner hair cells (IHC) and outer hair cells (OHC) was calculated in the left ear (siRNA treated) and in the right ear (saline treated). Since the effect of the siRNA was similar across dose, the data was pooled from the 3 doses. As demonstrated in Table F-1 below, carboplatin preferentially damages the inner hair cells in the chinchilla at the 75 mg/kg dose while the outer hair cells remain intact. Furthermore, the p53 siRNA significantly reduces carboplatin-induced inner hair cells loss in the cochlea (53.5% of inner hair cell loss in the p53 siRNA treated cochlea versus 71.9% of inner hair cell loss in the PBS treated cochlea).

TABLE F-1

QM5 siRNA Significantly Reduces Carboplatin-Induced IHC Loss in Chinchilla

| | SIRNA TREATED | | | CONTROL EAR | |
|---|---|---|---|---|---|
| Chinchilla # | IHC | OHC | Chin | IHC | OHC |
| 8136L | 64.7 | 0.6 | 8136R | 68.8 | 1.1 |
| 8140L | 48.2 | 0.8 | 8140R | 87.6 | 1.8 |
| 8143L | 53.3 | 1.5 | 8143R | 64.8 | 2.4 |
| 8149L | 38.3 | 1.9 | 8149r | 68.5 | 3 |
| 8153L | 59.7 | 3.1 | 8153R | 58.2 | 2.1 |
| 8197L | 50.1 | 1.2 | 8197R | 61.2 | 1.5 |
| 8200L | 45.4 | 1.7 | 8200R | 82.5 | 1.5 |
| 8202L | 68.5 | 3.0 | 8202R | 83.5 | 2.6 |
| Mean Treated | 53.5 | 1.7 | Mean Control | 71.9 | 2.0 |

Example 5

The Effect of p53 siRNA Treatment on Acoustic-Induced Hair Cell Death in the Cochlea of Chinchilla The activity of p53 siRNA (QM5) in an acoustic trauma model was studied in chinchilla. A group of 7 animals underwent the acoustic trauma. The animals were exposed to an octave band of noise centered at 4 kHz for 2.5 h at 105 dB. The left ear of the noise-exposed chinchillas was pre-treated (48 h before the acoustic trauma) with 30 μg of siRNA in ~10 μL of saline; the right ear was pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear was assessed 2.5 weeks after the acoustic trauma. Specifically, the mean threshold of the compound action potential recorded from the round window was determined 2.5 weeks after the acoustic trauma in order to determine if the thresholds in the siRNA-treated ear were lower (better) than the untreated (saline) ear. In addition, the amount of inner and outer hair cell loss was determined in the siRNA-treated and the control ear. FIG. 5 shows the mean threshold results recorded from the round window of siRNA-treated (filled circle) and saline-treated (open circle) chinchillas 2.5 weeks after the acoustic trauma. As demonstrated in FIG. 5, the mean thresholds were lower in the siRNA-treated ears versus the untreated ears. The difference at 4 kHz was statistically significant (p<0.033). These results indicate that p53 siRNA administered to the round window of the cochlea is capable of reducing the ID damage caused by acoustic trauma.

Table F-2 below shows the loss of outer hair cells (OHC) and inner hair cells (IHC) for each animal in the Basal Half of the cochlea (50-100% from the apex). The mean OHC loss in the siRNA-treated ears was significantly less than in the control ears (13.9% OHC loss in the siRNA-treated ear versus 19.6% OHC loss in the control ear, as determined by paired t-test). In general, there was less IHC loss that OHC loss in both siRNA-treated and control ears. The mean IHC loss was 4.5% in control ears and 1.3% in the siRNA-treated ears. This difference was not significant statistically. These results indicate that p53 siRNA administered to the round window of the cochlea is capable of reducing OHC loss in the Basal Half of the cochlea caused by acoustic trauma.

TABLE F-2

QM5 siRNA Significantly Reduces Acoustic-Induced OHC Loss in the basal half of cochlea in Chinchilla

| Chin# | SiRNA-treated (left ear) | | Control (right ear) | |
|---|---|---|---|---|
| | IHC | OHC | IHC | OHC |
| 8146 | 0.0% | 0.1% | 6.9% | 9.7% |
| 8196 | 0.7% | 3.4% | 2.5% | 13.4% |
| 8220 | 6.7% | 79.7% | 19.8% | 92.4% |
| 8222 | 0.0% | 2.4% | 0.1% | 5.0% |
| 8237 | 1.4% | 2.3% | 1.8% | 7.5% |
| 8238 | 0.1% | 3.6% | 0.0% | 1.7% |
| 8246 | 0.3% | 6.0% | 0.6% | 7.4% |
| Mean | 1.3% | 13.9% | 4.5% | 19.6% |
| SD | 2.4% | 29.1% | 7.1% | 32.3% |

Example 6

The Effect of p53 or 801 siRNA Treatment on Cisplatin-Induced Hair Cell Death in the Cochlea of Rats Male Wistar Rats were tested for basal auditory brainstem response (ABR) thresholds for signals of clicks, 8, 16 and 32 kHz prior to cisplatin treatment. Following the basal auditory brainstem response testing, cisplatin was administered as an intraperitoneal infusion of 13 mg/kg over 30 minutes. Treated ears received either 15 ug/4 microliters of p53 siRNA (QM5 molecule in Table A) in PBS or 801 siRNA in PBS (applied directly to the round window membrane). The 801 siRNA is designated REDD14 and has the following nucleotide sequence in the sense strand: 5'-GUGCCAACCUGAUG-CAGCU-3' (SEQ ID NO: 317) and in the antisense stran: 5'-AGCUGCAUCAGGUUGGCAC-3' (SEQ ID NO: 318). Control ears were treated with either non-related GFP siRNA or PBS. The siRNA molecules were administered between 3-5 days prior to cisplatin administration in order to permit protective effect on the cochlea.

The auditory brainstem response (ABR) testing was repeated 3 days after cisplatin administration. The auditory brainstem response thresholds were compared between pre-treatment and posttreatment and the shift in thresholds is indicated in Table G. Higher shift in thresholds following cisplatin treatment is indicative for more severe hair cells loss in the cochlea. After the repeat of auditory brainstem response testing, animals were sacrificed and cochleae were removed and processed for scanning electron microscopy (SEM) to quantify outer hair cell (OHC) loss in the hook region (high frequency region). The % outer hair cell loss was calculated by dividing the number of missing or severely damaged cells by the total number of outer hair cells in the field of the photograph.

Table G demonstrates the results obtained from four animals that underwent the cisplatin-induced damage and were analysed for outer hair cell loss in the Hook region. As revealed from the results, animals that received the siRNA directed against p53 or 801 exhibited lower outer hair cell loss and smaller shifts in the threshold for signals of 32 kHz. Both parameters indicate that siRNA directed against the p53 or 801 genes (mRNA) is protective against cisplatin-induced damage in the cochlea.

TABLE G

Hair cell loss versus threshold shift in cisplatin-treated cochlea of rats

| Treatment | Outer hair cell (OHC) loss | Auditory brainstem response (Threshold shift at 32 KHz) |
|---|---|---|
| QC/L P53 siRNA (QM5) | 50% | 10 dB |
| QC/R PBS | 100% | 30 dB |
| QF/L P53 siRNA (QM5) | 20% | 10 dB |
| QF/R GFP | 56% | 27.5 dB |
| QJ/R 801 siRNA (REDD14) | 20% | 17.5 dB |
| QJ/L GFP | 100% | 27.5 dB |
| QN/L 801 siRNA (REDD14) | 0% | 10 dB |
| QN/R PBS | 100% | 17.5 dB |

Example 7

Model Systems of Acute Renal Failure (ARF)

Testing the active siRNA for treating ARF may be done for example by using sepsis-induced ARF or ischemia-reperfusion-induced ARF 1. Sepsis Induced ARF Two predictive animal models of sepsis-induced ARF are described by Miyaji T, Flu X, Yuen P S, Muramatsu Y, Iyer S. Hewitt S M, Star R A, 2003, *Ethyl pyruvate decreases sepsis-induced acute renal failure and multiple organ damage in aged mice*, Kidney Int. November; 64(5):1620-31. These two models are lipopolysaccharide administration and cecal ligation puncture in mice, preferably in aged mice.

2. Ischemia reperfusion-induced ARF

This predictive animal model is described by Kelly K J, Plotkin Z, Vulgamott S L, Dagher P C, 2003 January, *P53 mediates the apoptotic response to GTP depletion after renal ischemia-reperfusion: protective role of a p53 inhibitor*, J Am Soc Nephrol.; 14(1):128-38.

Ischemia-reperfusion injury was induced in rats following 45 minutes bilateral kidney arterial clamp and subsequent release of the clamp to allow 24 hours of reperfusion. An amount of 250 μg of p53 siRNA (QM5 sequence, Table A) was injected into the jugular vein 2 hrs prior to and 30 minutes following the clamp. Additional amount of 250 μg of siRNA were given via the tail vein at 4 and 8 hrs after the clamp. siRNA against GFP served as a negative control. The siRNA used in the experiments described herein had a phosphate group at the 3' terminus of both the sense and antisense strand. The 3'-non-phosphorylated siRNA has been found to have similar biologically activity in an animal model as the corresponding 3'-phosphorylated siRNA. ARF progression was monitored by measurement of serum creatinine levels before and 24 hrs post surgery. At the end of the experiment, the rats were perfused via an indwelling femoral line with warm PBS followed by 4% paraformaldehyde. The left kidneys were removed and stored in 4% paraformaldehyde for subsequent histological analysis. Acute renal failure is frequently defined as an acute increase of the serum creatinine level from baseline. An increase of at least 0.5 mg per dL or 44.2 μmol per L of serum creatinine is considered as an indication for acute renal failure. Serum creatinine was measured at time zero before the surgery and at 24 hours post ARF surgery.

To study the distribution of p53 siRNA in the rat kidney, Cy3-labeled 19-mer blunt-ended siRNA molecules (2 mg/kg) having alternating O-methyl modification in the sugar residues were administered iv for 3-5 min, after which in vivo imaging was conducted using two-photon confocal microscopy (not shown). The confocal microscopy analysis revealed that the majority of siRNA in the kidneys is concentrated in the endosomal compartment of proximal tubular cells. Both endosomal and cytoplasmic siRNA fluorescence were relatively stable during the first 2 hrs post delivery and disappeared at 24 hrs.

Figure 6:
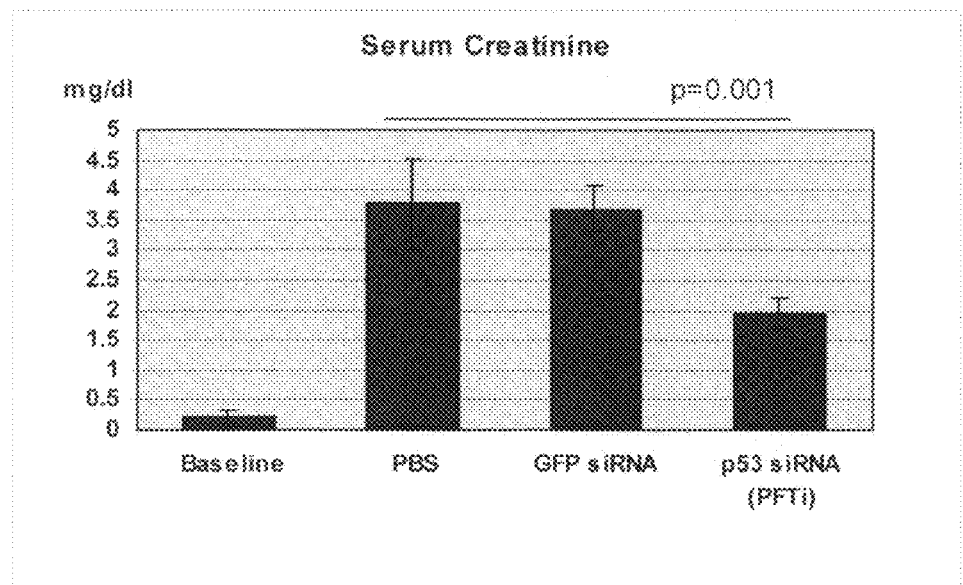
FIG. 6. This figure shows the level of serum creatinine as art indication for acute renal failure in animals that underwent bilateral kidney arterial clamp and were treated with p53 siRNA compound or a control, as indicated.

As evident from FIG. 6, there was a ten-fold increase in the level of rum creatinine following the 45-min of kidney bilateral arterial clamp treatment (PBS treatment). Four injections of p53 siRNA (QM5 sequence, Table A) (2 hrs prior to the clamp and 30 min, 4 h and 8 h after the clamp) significantly reduced the creatinine level in serum by 50% (P<0.001). These results demonstrated that p53 siRNA protected renal tissue from the effects of ischemia-reperfusion injury and thus reduce the severity of ARF.

Figure 7:
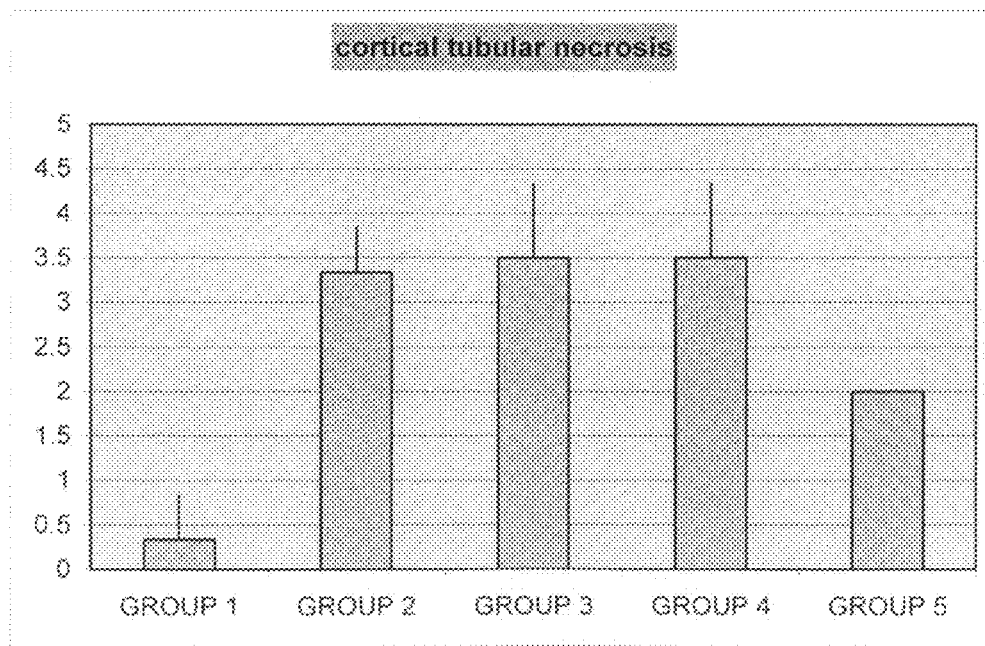
FIG. 7. This figure shows the extent of tubular necrosis in renal tissue in animals that underwent bilateral kidney arterial clamp and were treated with the p53 siRNA compound.
Figure 8:
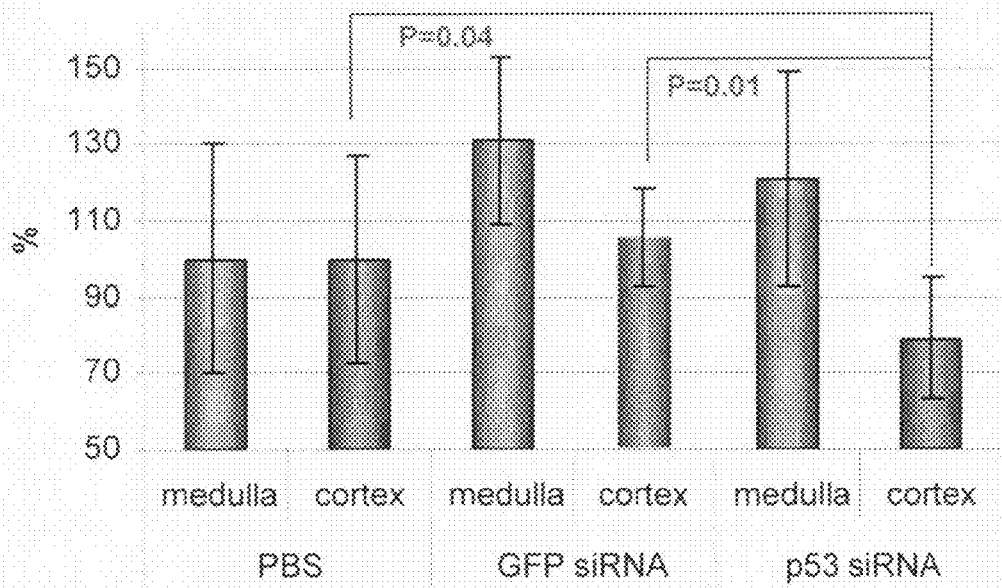
FIG. 8. This figure demonstrates that p53 siRNA treatment down-regulated the expression of the pro-apoptotic gene Puma in the cortical compartment of the kidney in animal subjected to ischemia-reperfusion kidney injury.

The effect of p53 siRNA treatment on renal ischemia-reperfusion injury was further determined by analysing the extent of tubular necrosis in the renal tissue. Tubular necrosis may be scored as: no damage (damage scoring 0), unicellular, patchy isolated necrosis (damage scoring 1), tubular necrosis in less than 25% of the tissue (damage scoring 2), tubular necrosis in between 25 and 50% of the tissue (damage scoring 3) and tubular necrosis in more than 50% of the tissue (damage scoring 4). FIG. 7 demonstrates the tubular kidney damage expressed as damage scoring (Y-axis) in animals that did not undergo ischemia-reperfusion injury (group) or in ischemia-reperfusion injury animals following treatment with either PBS (group 2), two injections of p53 siRNA (group 3), three injections of p53 siRNA (group 4) or four injections of p53 siRNA (group 5). As revealed by FIG. 7, four injections of p53 siRNA led to significant decrease in the tubular kidney damage as compared to the PBS control group. FIG. 8 demonstrates that four injections of p53 siRNA treatment down-regulated the expression of the pro-apoptotic gene Puma in the cortical compartment of the kidney in animal subjected to ischemia-reperfusion injury. This indicates that p53 siRNA treatment is inhibited the apoptotic processes in the kidney following ischemia-reperfusion injury.

In an additional set of experiments, the effect of a single siRNA injection at various time-points pre- and post-clamp was examined. 12 mg/kg of p53 siRNA (QM5 sequence, Table A) were injected into the jugular vein either 2 hrs prior to the clamp, 30 minutes prior the clamp, 4 hrs post clamp, 8 hrs post clamp, 12 hrs post clamp or 16 hrs post clamp. The effect of the single injection was calculated as the increase in serum creatinine level in animals underwent the kidney bilateral arterial clamp with the p53 siRNA treatment compared to animals underwent the kidney bilateral arterial clamp only. As revealed from Table H below, a single injection of p53 siRNA (12 mg/kg) was most effective in reducing serum creatinine when administered 4 hours post-clamp. However, significant effect was observed also when the p53 siRNA was administered 2 h or 0.5 h pre-clamp or 8 h post-clamp. Injection of 6 mg/kg of p53 siRNA 4 hrs post clamp was less effective than the 12 mg/kg dose, indicating a dose-dependent response of the p53 siRNA.

TABLE H

The effect of single siRNA injection at various time-points pre- and post- clamp

| Dosage of siRNA single injection | Timing of siRNA administration | Creatinin levels in mg/dl |
|---|---|---|
| Clamp only | | 3.8 mg/dl |
| 12 mg/kg | 2 h pre-clamp | 2.3 mg/dl |
| 12 mg/kg | 0.5 h pre-clamp | 2.8 mg/dl |
| 12 mg/kg | 4 h post-clamp | 1.3 mg/dl |
| 12 mg/kg | 8 h post-clamp | 2.5 mg/dl |
| 12 mg/kg | 12 h post-clamp | 3.3 mg/dl |
| 12 mg/kg | 16 h post-clamp | 3.4 mg/dl |
| 6 mg/kg | 4 h post-clamp | 2.2 mg/dl |

The trafficking and degradation characteristics of siRNA molecules in proximal tubular cells of the kidney was also analyzed. Systemically infused Cy-3 labeled siRNA was quickly filtered, bound to the apical brush border of proximal tubule cells, and internalized into lysosomes 60 minutes post infusion. An increase in the fluorescence of the lysosomal pool occurs up to 2 hours post infusion followed by a drop off at the next observed timepoint of 4 hours. The cytosolic component remains constant throughout the initial time-points up to 2 hours, suggesting a degradation process occurs once this pool enters the cytosol.

What is claimed is:

1. A method of treating a patient at risk for acute renal failure following a renal ischemic-reperfusion event which comprises administering to the patient a composition comprising a double-stranded RNA compound having the structure:

5' ugaagggugaaauauucuc 3' (antisense strand) (SEQ ID NO: 48)

3' acuucccacuuuauaagag 5' (sense strand) (SEQ ID NO: 25)

wherein each of a, c, u, and g is an unmodified or a 2'-O-Methyl sugar modified ribonucleotide and each consecutive ribonucleotide is joined to the next ribonucleotide by a covalent bond;

wherein alternating ribonucleotides in both the antisense strand and the sense strand are 2'-O-Methyl sugar modified ribonucleotides and a 2'-O-Methyl sugar modified ribonucleotide is present at the 5' terminus and at the 3' terminus of the antisense strand and an unmodified ribonucleotide is present at the 5' terminus and at the 3' terminus of the sense strand;

wherein the compound is from 19 to 23 ribonucleotides in length; and wherein the composition is administered in a therapeutically effective dose between 2 hours before and 8 hours following initiation of the renal ischemic-reperfusion event so as to down-regulate expression of a p53 gene and thereby treat the patient.

2. The method of claim 1, wherein the patient is a cardiac surgery patient.

3. The method of claim 1, wherein the composition is administered between 2-8 hours following the initiation of the renal ischemic-reperfusion event.

4. The method of claim 2, wherein the renal ischemic-reperfusion event is as a result of removal of a cardiopulmonary bypass machine.

5. The method of claim 1, wherein the compound is 19 ribonucleotides in length.

* * * * *

SEQUENCE LISTING

<160> NUMBER OF SEQ ID NOS: 388

<210> SEQ ID NO 1
<211> LENGTH: 2629
<212> TYPE: DNA
<213> ORGANISM: Homo sapiens

<400> SEQUENCE: 1

```
acttgtcatg gcgactgtcc agctttgtgc caggagcctc gcaggggttg atgggattgg      60
ggttttcccc tcccatgtgc tcaagactgg cgctaaaagt tttgagcttc tcaaaagtct     120
agagccaccg tccagggagc aggtagctgc tgggctccgg ggacactttg cgttcgggct     180
gggagcgtgc tttccacgac ggtgacacgc ttccctggat tggcagccag actgccttcc     240
gggtcactgc catggaggag ccgcagtcag atcctagcgt cgagcccect ctgagtcagg     300
aaacattttc agacctatgg aaactacttc ctgaaaacaa cgttctgtcc cccttgccgt     360
cccaagcaat ggatgatttg atgctgtccc cggacgatat tgaacaatgg ttcactgaag     420
acccaggtcc agatgaagct cccagaatgc cagaggctgc tccccgcgtg gcccctgcac     480
cagcagctcc tacaccggcg gcccctgcac cagccccctc ctggcccctg tcatcttctg     540
tcccttccca gaaaacctac cagggcagct acggtttccg tctgggcttc ttgcattctg     600
ggacagccaa gtctgtgact tgcacgtact cccctgccct caacaagatg ttttgccaac     660
tggccaagac ctgccctgtg cagctgtggg ttgattccac acccccgccc ggcacccgcg     720
tccgcgccat ggccatctac aagcagtcac agcacatgac ggaggttgtg aggcgctgcc     780
cccaccatga gcgctgctca gatagcgatg gtctggcccc tcctcagcat cttatccgag     840
tggaaggaaa tttgcgtgtg gagtatttgg atgacagaaa cacttttcga catagtgtgg     900
tggtgcccta tgagccgcct gaggttggct ctgactgtac caccatccac tacaactaca     960
tgtgtaacag ttcctgcatg ggcggcatga accggaggcc catcctcacc atcatcacac    1020
tggaagactc cagtggtaat ctactgggac ggaacagctt tgaggtgcgt gtttgtgcct    1080
gtcctgggag agaccggcgc acagaggaag agaatctccg caagaaaggg gagcctcacc    1140
acgagctgcc cccagggagc actaagcgag cactgcccaa caacaccagc tcctctcccc    1200
agccaaagaa gaaaccactg gatggagaat atttcaccct tcagatccgt gggcgtgagc    1260
gcttcgagat gttccgagag ctgaatgagg ccttggaact caaggatgcc caggctggga    1320
aggagccagg ggggagcagg gctcactcca gccacctgaa gtccaaaaag ggtcagtcta    1380
cctcccgcca taaaaaactc atgttcaaga cagaagggcc tgactcagac tgacattctc    1440
cacttcttgt tccccactga cagcctccca ccccatctc tccctcccct gccattttgg    1500
gttttgggtc tttgaacccc tgcttgcaat aggtgtgcgt cagaagcacc caggacttcc    1560
atttgctttg tccgggggct ccactgaaca gttggcctg cactggtgtt ttgttgtggg    1620
gaggaggatg gggagtagga cataccagct tagattttaa ggtttttact gtgagggatg    1680
tttgggagat gtaagaaatg ttcttgcagt taagggttag tttacaatca gccacattct    1740
aggtaggtag gggcccactt caccgtacta accaggaag ctgtccctca tgttgaattt    1800
tctctaactt caaggcccat atctgtgaaa tgctggcatt tgcacctacc tcacagagtg    1860
cattgtgagg gttaatgaaa taatgtacat ctggccttga aaccacctttt attacatgg    1920
ggtctaaaaac ttgacccct tgagggtgcc tgttccctct ccctctccct gttggctggt    1980
gggttggtag tttctacagt tgggcagctg gttaggtaga gggagttgtc aagtcttgct    2040
```

-continued

```
ggcccagcca aaccctgtct gacaacctct tggtcgacct tagtacctaa aaggaaatct    2100 cacccccatcc cacaccctgg aggatttcat ctcttgtata tgatgatctg gatccaccaa    2160
gacttgtttt atgctcaggg tcaatttctt ttttcttttt ttttttttttt tttcttttc     2220 tttgagactg ggtctcgctt tgttgcccag gctggagtgg agtggcgtga tcttggctta    2280
ctgcagcctt tgcctccccg gctcgagcag tcctgcctca gcctccggag tagctgggac    2340
cacaggttca tgccaccatg gccagccaac ttttgcatgt tttgtagaga tggggtctca    2400
cagtgttgcc caggctggtc tcaaactcct gggctcaggc gatccacctg tctcagcctc    2460
ccagagtgct gggattacaa ttgtgagcca ccacgtggag ctggaagggt caacatcttt    2520
tacattctgc aagcacatct gcattttcac cccacccttc ccctccttct cccttttttat   2580 atcccatttt tatatcgatc tcttatttta caataaaact ttgctgcca                 2629
```

<210> SEQ ID NO 2
<211> LENGTH: 393
<212> TYPE: PRT
<213> ORGANISM: Homo sapiens

<400> SEQUENCE: 2

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270
```

```
Arg Val Cys Ala Cys Pro Gly Arg Asp Arg Arg Thr Glu Glu Glu Asn
    275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
                355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390

<210> SEQ ID NO 3
<211> LENGTH: 19
<212> TYPE: RNA
<213> ORGANISM: Mus musculus

<400> SEQUENCE: 3
guacaugugu aauagcucc                                                      19

<210> SEQ ID NO 4
<211> LENGTH: 19
<212> TYPE: RNA
<213> ORGANISM: Homo sapiens

<400> SEQUENCE: 4
gacuccagug guaaucuac                                                      19

<210> SEQ ID NO 5
<211> LENGTH: 19
<212> TYPE: RNA
<213> ORGANISM: Homo sapiens

<400> SEQUENCE: 5
cagaccuaug gaaacuacu                                                      19

<210> SEQ ID NO 6
<211> LENGTH: 19
<212> TYPE: RNA
<213> ORGANISM: Homo sapiens

<400> SEQUENCE: 6
cuaccucccg ccauaaaaa                                                      19

<210> SEQ ID NO 7
<211> LENGTH: 19
<212> TYPE: RNA
<213> ORGANISM: Homo sapiens

<400> SEQUENCE: 7
cccaagcaau ggaugauuu                                                      19

<210> SEQ ID NO 8
<211> LENGTH: 19
<212> TYPE: RNA
<213> ORGANISM: Homo sapiens
```

```
<400> SEQUENCE: 8
cccggacgau auugaacaa                                               19

<210> SEQ ID NO 9
<211> LENGTH: 19
<212> TYPE: RNA
<213> ORGANISM: Mus musculus

<400> SEQUENCE: 9
gagucacagu cggauauca                                               19

<210> SEQ ID NO 10
<211> LENGTH: 19
<212> TYPE: RNA
<213> ORGANISM: Mus musculus

<400> SEQUENCE: 10
ggauguugag gaguuuuuu                                               19

<210> SEQ ID NO 11
<211> LENGTH: 19
<212> TYPE: RNA
<213> ORGANISM: Mus musculus

<400> SEQUENCE: 11
caucuuuugu cccuucuca                                               19

<210> SEQ ID NO 12
<211> LENGTH: 19
<212> TYPE: RNA
<213> ORGANISM: Mus musculus

<400> SEQUENCE: 12
ggaauagguu gauaguugu                                               19

<210> SEQ ID NO 13
<211> LENGTH: 19
<212> TYPE: RNA
<213> ORGANISM: Mus musculus

<400> SEQUENCE: 13
ggacagccaa gucuguuau                                               19

<210> SEQ ID NO 14
<211> LENGTH: 19
<212> TYPE: RNA
<213> ORGANISM: Mus musculus

<400> SEQUENCE: 14
gaagaaaauu uccgcaaaa                                               19

<210> SEQ ID NO 15
<211> LENGTH: 19
<212> TYPE: RNA
<213> ORGANISM: Homo sapiens

<400> SEQUENCE: 15
cugggacagc caagucugu                                               19

<210> SEQ ID NO 16
<211> LENGTH: 19
<212> TYPE: RNA
<213> ORGANISM: Homo sapiens
```

```
<400> SEQUENCE: 16
ucaucacacu ggaagacuc                                                  19

<210> SEQ ID NO 17
<211> LENGTH: 19
<212> TYPE: RNA
<213> ORGANISM: Homo sapiens

<400> SEQUENCE: 17
cacacuggaa gacuccagu                                                  19

<210> SEQ ID NO 18
<211> LENGTH: 19
<212> TYPE: RNA
<213> ORGANISM: Homo sapiens

<400> SEQUENCE: 18
gcgccauggc caucuacaa                                                  19

<210> SEQ ID NO 19
<211> LENGTH: 19
<212> TYPE: RNA
<213> ORGANISM: Homo sapiens

<400> SEQUENCE: 19
cgccauggcc aucuacaag                                                  19

<210> SEQ ID NO 20
<211> LENGTH: 19
<212> TYPE: RNA
<213> ORGANISM: Homo sapiens

<400> SEQUENCE: 20
agucacagca caugacgga                                                  19

<210> SEQ ID NO 21
<211> LENGTH: 19
<212> TYPE: RNA
<213> ORGANISM: Homo sapiens

<400> SEQUENCE: 21
uccgagugga aggaaauuu                                                  19

<210> SEQ ID NO 22
<211> LENGTH: 19
<212> TYPE: RNA
<213> ORGANISM: Homo sapiens

<400> SEQUENCE: 22
ccgaguggaa ggaaauuug                                                  19

<210> SEQ ID NO 23
<211> LENGTH: 19
<212> TYPE: RNA
<213> ORGANISM: Homo sapiens

<400> SEQUENCE: 23
gacagaaaca cuuuucgac                                                  19

<210> SEQ ID NO 24
<211> LENGTH: 19
<212> TYPE: RNA
<213> ORGANISM: Homo sapiens
```

-continued

```
<400> SEQUENCE: 24 guguggu ggu gcccuauga                                              19

<210> SEQ ID NO 25
<211> LENGTH: 19
<212> TYPE: RNA
<213> ORGANISM: Homo sapiens

<400> SEQUENCE: 25
gagaauauuu cacccuuca                                               19

<210> SEQ ID NO 26
<211> LENGTH: 19
<212> TYPE: RNA
<213> ORGANISM: Mus musculus

<400> SEQUENCE: 26
ggagcuauua cacauguac                                               19

<210> SEQ ID NO 27
<211> LENGTH: 19
<212> TYPE: RNA
<213> ORGANISM: Homo sapiens

<400> SEQUENCE: 27
guagauuacc acuggaguc                                               19

<210> SEQ ID NO 28
<211> LENGTH: 19
<212> TYPE: RNA
<213> ORGANISM: Homo sapiens

<400> SEQUENCE: 28
aguaguuucc auaggucug                                               19

<210> SEQ ID NO 29
<211> LENGTH: 19
<212> TYPE: RNA
<213> ORGANISM: Homo sapiens

<400> SEQUENCE: 29
uuuuuauggc gggagguag                                               19

<210> SEQ ID NO 30
<211> LENGTH: 19
<212> TYPE: RNA
<213> ORGANISM: Homo sapiens

<400> SEQUENCE: 30
aaaucaucca uugcuuggg                                               19

<210> SEQ ID NO 31
<211> LENGTH: 19
<212> TYPE: RNA
<213> ORGANISM: Homo sapiens

<400> SEQUENCE: 31
uuguucaaua ucguccggg                                               19

<210> SEQ ID NO 32
<211> LENGTH: 19
<212> TYPE: RNA
<213> ORGANISM: Mus musculus
```

```
<400> SEQUENCE: 32
ugauauccga cugugacuc                                             19

<210> SEQ ID NO 33
<211> LENGTH: 19
<212> TYPE: RNA
<213> ORGANISM: Mus musculus

<400> SEQUENCE: 33
aaaaaacucc ucaacaucc                                             19

<210> SEQ ID NO 34
<211> LENGTH: 19
<212> TYPE: RNA
<213> ORGANISM: Mus musculus

<400> SEQUENCE: 34
ugagaaggga caaaagaug                                             19

<210> SEQ ID NO 35
<211> LENGTH: 19
<212> TYPE: RNA
<213> ORGANISM: Mus musculus

<400> SEQUENCE: 35
acaacuauca accuauucc                                             19

<210> SEQ ID NO 36
<211> LENGTH: 19
<212> TYPE: RNA
<213> ORGANISM: Mus musculus

<400> SEQUENCE: 36
auaacagacu uggcugucc                                             19

<210> SEQ ID NO 37
<211> LENGTH: 19
<212> TYPE: RNA
<213> ORGANISM: Mus musculus

<400> SEQUENCE: 37
uuuugcggaa auuuucuuc                                             19

<210> SEQ ID NO 38
<211> LENGTH: 19
<212> TYPE: RNA
<213> ORGANISM: Homo sapiens

<400> SEQUENCE: 38
acagacuugg cgucccag                                              19

<210> SEQ ID NO 39
<211> LENGTH: 19
<212> TYPE: RNA
<213> ORGANISM: Homo sapiens

<400> SEQUENCE: 39
gagucuucca gugugauga                                             19

<210> SEQ ID NO 40
<211> LENGTH: 19
<212> TYPE: RNA
<213> ORGANISM: Homo sapiens
```

```
<400> SEQUENCE: 40
acuggagucu uccagugug                                                 19

<210> SEQ ID NO 41
<211> LENGTH: 19
<212> TYPE: RNA
<213> ORGANISM: Homo sapiens

<400> SEQUENCE: 41
uuguagaugg ccauggcgc                                                 19

<210> SEQ ID NO 42
<211> LENGTH: 19
<212> TYPE: RNA
<213> ORGANISM: Homo sapiens

<400> SEQUENCE: 42
cuuguagaug gccauggcg                                                 19

<210> SEQ ID NO 43
<211> LENGTH: 19
<212> TYPE: RNA
<213> ORGANISM: Homo sapiens

<400> SEQUENCE: 43
uccgucaugu gcugugacu                                                 19

<210> SEQ ID NO 44
<211> LENGTH: 19
<212> TYPE: RNA
<213> ORGANISM: Homo sapiens

<400> SEQUENCE: 44
aaauuuccuu ccacucgga                                                 19

<210> SEQ ID NO 45
<211> LENGTH: 19
<212> TYPE: RNA
<213> ORGANISM: Homo sapiens

<400> SEQUENCE: 45
caaauuuccu uccacucgg                                                 19

<210> SEQ ID NO 46
<211> LENGTH: 19
<212> TYPE: RNA
<213> ORGANISM: Homo sapiens

<400> SEQUENCE: 46
gucgaaaagu guuucuguc                                                 19

<210> SEQ ID NO 47
<211> LENGTH: 19
<212> TYPE: RNA
<213> ORGANISM: Homo sapiens

<400> SEQUENCE: 47
ucauagggca ccaccacac                                                 19

<210> SEQ ID NO 48
<211> LENGTH: 19
<212> TYPE: RNA
<213> ORGANISM: Homo sapiens
```

```
<400> SEQUENCE: 48
ugaaggguga aauauucuc                                              19

<210> SEQ ID NO 49
<211> LENGTH: 19
<212> TYPE: RNA
<213> ORGANISM: Homo sapiens

<400> SEQUENCE: 49
guaccaccau ccacuacaa                                              19

<210> SEQ ID NO 50
<211> LENGTH: 19
<212> TYPE: RNA
<213> ORGANISM: Homo sapiens

<400> SEQUENCE: 50
ggaaacuacu uccugaaaa                                              19

<210> SEQ ID NO 51
<211> LENGTH: 19
<212> TYPE: RNA
<213> ORGANISM: Homo sapiens

<400> SEQUENCE: 51
agacuccagu gguaaucua                                              19

<210> SEQ ID NO 52
<211> LENGTH: 19
<212> TYPE: RNA
<213> ORGANISM: Homo sapiens

<400> SEQUENCE: 52
ccauccacua caacuacau                                              19

<210> SEQ ID NO 53
<211> LENGTH: 19
<212> TYPE: RNA
<213> ORGANISM: Homo sapiens

<400> SEQUENCE: 53
ccaccaucca cuacaacua                                              19

<210> SEQ ID NO 54
<211> LENGTH: 19
<212> TYPE: RNA
<213> ORGANISM: Homo sapiens

<400> SEQUENCE: 54
aaacacuuuu cgacauagu                                              19

<210> SEQ ID NO 55
<211> LENGTH: 19
<212> TYPE: RNA
<213> ORGANISM: Homo sapiens

<400> SEQUENCE: 55
caugagcgcu gcucagaua                                              19

<210> SEQ ID NO 56
<211> LENGTH: 19
<212> TYPE: RNA
<213> ORGANISM: Homo sapiens
```

-continued

```
<400> SEQUENCE: 56
ccauggccau cuacaagca                                          19

<210> SEQ ID NO 57
<211> LENGTH: 19
<212> TYPE: RNA
<213> ORGANISM: Homo sapiens

<400> SEQUENCE: 57
ccaagucugu gacuugcac                                          19

<210> SEQ ID NO 58
<211> LENGTH: 19
<212> TYPE: RNA
<213> ORGANISM: Homo sapiens

<400> SEQUENCE: 58
aaacuuugcu gccaaaaaa                                          19

<210> SEQ ID NO 59
<211> LENGTH: 19
<212> TYPE: RNA
<213> ORGANISM: Homo sapiens

<400> SEQUENCE: 59
cccuccuucu cccuuuuua                                          19

<210> SEQ ID NO 60
<211> LENGTH: 19
<212> TYPE: RNA
<213> ORGANISM: Homo sapiens

<400> SEQUENCE: 60
gcaagcacau cugcauuuu                                          19

<210> SEQ ID NO 61
<211> LENGTH: 19
<212> TYPE: RNA
<213> ORGANISM: Homo sapiens

<400> SEQUENCE: 61
gggucaacau cuuuuacau                                          19

<210> SEQ ID NO 62
<211> LENGTH: 19
<212> TYPE: RNA
<213> ORGANISM: Homo sapiens

<400> SEQUENCE: 62 gaaggucaa caucuuuua                                           19

<210> SEQ ID NO 63
<211> LENGTH: 19
<212> TYPE: RNA
<213> ORGANISM: Homo sapiens

<400> SEQUENCE: 63
cuggaagggu caacaucuu                                          19

<210> SEQ ID NO 64
<211> LENGTH: 19
<212> TYPE: RNA
<213> ORGANISM: Homo sapiens
```

```
<400> SEQUENCE: 64
ccagagugcu gggauuaca                                            19

<210> SEQ ID NO 65
<211> LENGTH: 19
<212> TYPE: RNA
<213> ORGANISM: Homo sapiens

<400> SEQUENCE: 65
gauggggucu cacaguguu                                            19

<210> SEQ ID NO 66
<211> LENGTH: 19
<212> TYPE: RNA
<213> ORGANISM: Homo sapiens

<400> SEQUENCE: 66
gccaacuuuu gcauguuuu                                            19

<210> SEQ ID NO 67
<211> LENGTH: 19
<212> TYPE: RNA
<213> ORGANISM: Homo sapiens

<400> SEQUENCE: 67
ccauggccag ccaacuuuu                                            19

<210> SEQ ID NO 68
<211> LENGTH: 19
<212> TYPE: RNA
<213> ORGANISM: Homo sapiens

<400> SEQUENCE: 68
agacccaggu ccagaugaa                                            19

<210> SEQ ID NO 69
<211> LENGTH: 19
<212> TYPE: RNA
<213> ORGANISM: Homo sapiens

<400> SEQUENCE: 69
ccaucaucac acuggaaga                                            19

<210> SEQ ID NO 70
<211> LENGTH: 19
<212> TYPE: RNA
<213> ORGANISM: Homo sapiens

<400> SEQUENCE: 70
caucacacug gaagacucc                                            19

<210> SEQ ID NO 71
<211> LENGTH: 19
<212> TYPE: RNA
<213> ORGANISM: Homo sapiens

<400> SEQUENCE: 71
caucaucaca cuggaagac                                            19

<210> SEQ ID NO 72
<211> LENGTH: 19
<212> TYPE: RNA
<213> ORGANISM: Homo sapiens
```

```
<400> SEQUENCE: 72
accaucauca cacuggaag                                          19

<210> SEQ ID NO 73
<211> LENGTH: 19
<212> TYPE: RNA
<213> ORGANISM: Homo sapiens

<400> SEQUENCE: 73
aucaucacac uggaagacu                                          19

<210> SEQ ID NO 74
<211> LENGTH: 19
<212> TYPE: RNA
<213> ORGANISM: Homo sapiens

<400> SEQUENCE: 74
cacuggaaga cuccagugg                                          19

<210> SEQ ID NO 75
<211> LENGTH: 19
<212> TYPE: RNA
<213> ORGANISM: Homo sapiens

<400> SEQUENCE: 75
acacuggaag acuccagug                                          19

<210> SEQ ID NO 76
<211> LENGTH: 19
<212> TYPE: RNA
<213> ORGANISM: Homo sapiens

<400> SEQUENCE: 76
ucacacugga agacuccag                                          19

<210> SEQ ID NO 77
<211> LENGTH: 19
<212> TYPE: RNA
<213> ORGANISM: Homo sapiens

<400> SEQUENCE: 77
aucacacugg aagacucca                                          19

<210> SEQ ID NO 78
<211> LENGTH: 19
<212> TYPE: RNA
<213> ORGANISM: Homo sapiens

<400> SEQUENCE: 78
cacagcacau gacggaggu                                          19

<210> SEQ ID NO 79
<211> LENGTH: 19
<212> TYPE: RNA
<213> ORGANISM: Homo sapiens

<400> SEQUENCE: 79
cacuggaaga cuccagugg                                          19

<210> SEQ ID NO 80
<211> LENGTH: 19
<212> TYPE: RNA
<213> ORGANISM: Homo sapiens
```

```
<400> SEQUENCE: 80
ucacagcaca ugacggagg                                                19

<210> SEQ ID NO 81
<211> LENGTH: 19
<212> TYPE: RNA
<213> ORGANISM: Homo sapiens

<400> SEQUENCE: 81
gucacagcac augacggag                                                19

<210> SEQ ID NO 82
<211> LENGTH: 19
<212> TYPE: RNA
<213> ORGANISM: Homo sapiens

<400> SEQUENCE: 82
ccauccacua caacuacau                                                19

<210> SEQ ID NO 83
<211> LENGTH: 19
<212> TYPE: RNA
<213> ORGANISM: Homo sapiens

<400> SEQUENCE: 83
ccaccaucca cuacaacua                                                19

<210> SEQ ID NO 84
<211> LENGTH: 19
<212> TYPE: RNA
<213> ORGANISM: Homo sapiens

<400> SEQUENCE: 84
gaauauuuca cccuucaga                                                19

<210> SEQ ID NO 85
<211> LENGTH: 19
<212> TYPE: RNA
<213> ORGANISM: Homo sapiens

<400> SEQUENCE: 85
cgaguggaag gaaauuugc                                                19

<210> SEQ ID NO 86
<211> LENGTH: 19
<212> TYPE: RNA
<213> ORGANISM: Homo sapiens

<400> SEQUENCE: 86
gagaauauuu cacccuuca                                                19

<210> SEQ ID NO 87
<211> LENGTH: 19
<212> TYPE: RNA
<213> ORGANISM: Homo sapiens

<400> SEQUENCE: 87
cuacaugugu aacaguucc                                                19

<210> SEQ ID NO 88
<211> LENGTH: 19
<212> TYPE: RNA
<213> ORGANISM: Homo sapiens
```

-continued

```
<400> SEQUENCE: 88
aacuacaugu guaacaguu                                              19

<210> SEQ ID NO 89
<211> LENGTH: 19
<212> TYPE: RNA
<213> ORGANISM: Homo sapiens

<400> SEQUENCE: 89
caacuacaug uguaacagu                                              19

<210> SEQ ID NO 90
<211> LENGTH: 19
<212> TYPE: RNA
<213> ORGANISM: Homo sapiens

<400> SEQUENCE: 90
cacuacaacu acaugugua                                              19

<210> SEQ ID NO 91
<211> LENGTH: 19
<212> TYPE: RNA
<213> ORGANISM: Homo sapiens

<400> SEQUENCE: 91
ccacuacaac uacaugugu                                              19

<210> SEQ ID NO 92
<211> LENGTH: 19
<212> TYPE: RNA
<213> ORGANISM: Homo sapiens

<400> SEQUENCE: 92
gacagaaaca cuuuucgac                                              19

<210> SEQ ID NO 93
<211> LENGTH: 19
<212> TYPE: RNA
<213> ORGANISM: Homo sapiens

<400> SEQUENCE: 93
ggagaauauu ucacccuuc                                              19

<210> SEQ ID NO 94
<211> LENGTH: 19
<212> TYPE: RNA
<213> ORGANISM: Homo sapiens

<400> SEQUENCE: 94
guguaacagu uccugcaug                                              19

<210> SEQ ID NO 95
<211> LENGTH: 19
<212> TYPE: RNA
<213> ORGANISM: Homo sapiens

<400> SEQUENCE: 95
acaacuacau guguaacag                                              19

<210> SEQ ID NO 96
<211> LENGTH: 19
<212> TYPE: RNA
<213> ORGANISM: Homo sapiens
```

```
<400> SEQUENCE: 96
acuacaacua cauguguaa                                              19

<210> SEQ ID NO 97
<211> LENGTH: 19
<212> TYPE: RNA
<213> ORGANISM: Homo sapiens

<400> SEQUENCE: 97
accauccacu acaacuaca                                              19

<210> SEQ ID NO 98
<211> LENGTH: 19
<212> TYPE: RNA
<213> ORGANISM: Homo sapiens

<400> SEQUENCE: 98
accaccaucc acuacaacu                                              19

<210> SEQ ID NO 99
<211> LENGTH: 19
<212> TYPE: RNA
<213> ORGANISM: Homo sapiens

<400> SEQUENCE: 99
uaccaccauc cacuacaac                                              19

<210> SEQ ID NO 100
<211> LENGTH: 19
<212> TYPE: RNA
<213> ORGANISM: Homo sapiens

<400> SEQUENCE: 100
acagaaacac uuuucgaca                                              19

<210> SEQ ID NO 101
<211> LENGTH: 19
<212> TYPE: RNA
<213> ORGANISM: Homo sapiens

<400> SEQUENCE: 101
gaguggaagg aaauuugcg                                              19

<210> SEQ ID NO 102
<211> LENGTH: 19
<212> TYPE: RNA
<213> ORGANISM: Homo sapiens

<400> SEQUENCE: 102
auauuucacc cuucagauc                                              19

<210> SEQ ID NO 103
<211> LENGTH: 19
<212> TYPE: RNA
<213> ORGANISM: Homo sapiens

<400> SEQUENCE: 103
aauauuucac ccuucagau                                              19

<210> SEQ ID NO 104
<211> LENGTH: 19
<212> TYPE: RNA
<213> ORGANISM: Homo sapiens
```

```
<400> SEQUENCE: 104
agaauauuuc acccuucag                                              19

<210> SEQ ID NO 105
<211> LENGTH: 19
<212> TYPE: RNA
<213> ORGANISM: Homo sapiens

<400> SEQUENCE: 105
uggagaauau uucacccuu                                              19

<210> SEQ ID NO 106
<211> LENGTH: 19
<212> TYPE: RNA
<213> ORGANISM: Homo sapiens

<400> SEQUENCE: 106
acauguguaa caguccug                                               19

<210> SEQ ID NO 107
<211> LENGTH: 19
<212> TYPE: RNA
<213> ORGANISM: Homo sapiens

<400> SEQUENCE: 107
uacaacuaca uguguaaca                                              19

<210> SEQ ID NO 108
<211> LENGTH: 19
<212> TYPE: RNA
<213> ORGANISM: Homo sapiens

<400> SEQUENCE: 108
cuacaacuac auguguaac                                              19

<210> SEQ ID NO 109
<211> LENGTH: 19
<212> TYPE: RNA
<213> ORGANISM: Homo sapiens

<400> SEQUENCE: 109
uccacuacaa cuacaugug                                              19

<210> SEQ ID NO 110
<211> LENGTH: 19
<212> TYPE: RNA
<213> ORGANISM: Homo sapiens

<400> SEQUENCE: 110
auccacuaca acuacaugu                                              19

<210> SEQ ID NO 111
<211> LENGTH: 19
<212> TYPE: RNA
<213> ORGANISM: Homo sapiens

<400> SEQUENCE: 111
cauccacuac aacuacaug                                              19

<210> SEQ ID NO 112
<211> LENGTH: 19
<212> TYPE: RNA
<213> ORGANISM: Homo sapiens
```

```
<400> SEQUENCE: 112
caccauccac uacaacuac                                              19

<210> SEQ ID NO 113
<211> LENGTH: 19
<212> TYPE: RNA
<213> ORGANISM: Homo sapiens

<400> SEQUENCE: 113
uguguaacag uuccugcau                                              19

<210> SEQ ID NO 114
<211> LENGTH: 19
<212> TYPE: RNA
<213> ORGANISM: Homo sapiens

<400> SEQUENCE: 114
cauguguaac aguccugc                                               19

<210> SEQ ID NO 115
<211> LENGTH: 19
<212> TYPE: RNA
<213> ORGANISM: Homo sapiens

<400> SEQUENCE: 115
uacaugugua acaguuccu                                              19

<210> SEQ ID NO 116
<211> LENGTH: 19
<212> TYPE: RNA
<213> ORGANISM: Homo sapiens

<400> SEQUENCE: 116
acuacaugug uaacaguuc                                              19

<210> SEQ ID NO 117
<211> LENGTH: 19
<212> TYPE: RNA
<213> ORGANISM: Homo sapiens

<400> SEQUENCE: 117
auccgagugg aaggaaauu                                              19

<210> SEQ ID NO 118
<211> LENGTH: 19
<212> TYPE: RNA
<213> ORGANISM: Homo sapiens

<400> SEQUENCE: 118
ucacuccagc caccugaag                                              19

<210> SEQ ID NO 119
<211> LENGTH: 19
<212> TYPE: RNA
<213> ORGANISM: Homo sapiens

<400> SEQUENCE: 119
cucacuccag ccaccugaa                                              19

<210> SEQ ID NO 120
<211> LENGTH: 19
<212> TYPE: RNA
<213> ORGANISM: Homo sapiens
```

```
<400> SEQUENCE: 120
uuguagugga uggugguac                                               19

<210> SEQ ID NO 121
<211> LENGTH: 19
<212> TYPE: RNA
<213> ORGANISM: Homo sapiens

<400> SEQUENCE: 121
uuuucaggaa guaguuccc                                               19

<210> SEQ ID NO 122
<211> LENGTH: 19
<212> TYPE: RNA
<213> ORGANISM: Homo sapiens

<400> SEQUENCE: 122
uagauuacca cuggagucu                                               19

<210> SEQ ID NO 123
<211> LENGTH: 19
<212> TYPE: RNA
<213> ORGANISM: Homo sapiens

<400> SEQUENCE: 123
auguaguugu aguggaugg                                               19

<210> SEQ ID NO 124
<211> LENGTH: 19
<212> TYPE: RNA
<213> ORGANISM: Homo sapiens

<400> SEQUENCE: 124
uaguuguagu ggauggugg                                               19

<210> SEQ ID NO 125
<211> LENGTH: 19
<212> TYPE: RNA
<213> ORGANISM: Homo sapiens

<400> SEQUENCE: 125
acuaugucga aaaguguuu                                               19

<210> SEQ ID NO 126
<211> LENGTH: 19
<212> TYPE: RNA
<213> ORGANISM: Homo sapiens

<400> SEQUENCE: 126
uaucugagca gcgcucaug                                               19

<210> SEQ ID NO 127
<211> LENGTH: 19
<212> TYPE: RNA
<213> ORGANISM: Homo sapiens

<400> SEQUENCE: 127
ugcuuguaga uggccaugg                                               19

<210> SEQ ID NO 128
<211> LENGTH: 19
<212> TYPE: RNA
<213> ORGANISM: Homo sapiens
```

```
<400> SEQUENCE: 128
gugcaaguca cagacuugg                                                19

<210> SEQ ID NO 129
<211> LENGTH: 19
<212> TYPE: RNA
<213> ORGANISM: Homo sapiens

<400> SEQUENCE: 129
uuuuuuggca gcaaaguuu                                                19

<210> SEQ ID NO 130
<211> LENGTH: 19
<212> TYPE: RNA
<213> ORGANISM: Homo sapiens

<400> SEQUENCE: 130
uaaaaaggga gaaggaggg                                                19

<210> SEQ ID NO 131
<211> LENGTH: 19
<212> TYPE: RNA
<213> ORGANISM: Homo sapiens

<400> SEQUENCE: 131
aaaaugcaga ugugcuugc                                                19

<210> SEQ ID NO 132
<211> LENGTH: 19
<212> TYPE: RNA
<213> ORGANISM: Homo sapiens

<400> SEQUENCE: 132
auguaaaaga uguugaccc                                                19

<210> SEQ ID NO 133
<211> LENGTH: 19
<212> TYPE: RNA
<213> ORGANISM: Homo sapiens

<400> SEQUENCE: 133
uaaaagaugu ugacccuuc                                                19

<210> SEQ ID NO 134
<211> LENGTH: 19
<212> TYPE: RNA
<213> ORGANISM: Homo sapiens

<400> SEQUENCE: 134
aagauguuga cccuuccag                                                19

<210> SEQ ID NO 135
<211> LENGTH: 19
<212> TYPE: RNA
<213> ORGANISM: Homo sapiens

<400> SEQUENCE: 135
uguaauccca gcacucugg                                                19

<210> SEQ ID NO 136
<211> LENGTH: 19
<212> TYPE: RNA
<213> ORGANISM: Homo sapiens
```

```
<400> SEQUENCE: 136
aacacuguga gaccccauc                                                    19

<210> SEQ ID NO 137
<211> LENGTH: 19
<212> TYPE: RNA
<213> ORGANISM: Homo sapiens

<400> SEQUENCE: 137
aaaacaugca aaaguuggc                                                    19

<210> SEQ ID NO 138
<211> LENGTH: 19
<212> TYPE: RNA
<213> ORGANISM: Homo sapiens

<400> SEQUENCE: 138
aaaaguuggc uggccaugg                                                    19

<210> SEQ ID NO 139
<211> LENGTH: 19
<212> TYPE: RNA
<213> ORGANISM: Homo sapiens

<400> SEQUENCE: 139
uucaucugga ccugggucu                                                    19

<210> SEQ ID NO 140
<211> LENGTH: 19
<212> TYPE: RNA
<213> ORGANISM: Homo sapiens

<400> SEQUENCE: 140
ucuuccagug ugaugaugg                                                    19

<210> SEQ ID NO 141
<211> LENGTH: 19
<212> TYPE: RNA
<213> ORGANISM: Homo sapiens

<400> SEQUENCE: 141
ggagucuucc agugugaug                                                    19

<210> SEQ ID NO 142
<211> LENGTH: 19
<212> TYPE: RNA
<213> ORGANISM: Homo sapiens

<400> SEQUENCE: 142
gucuuccagu gugaugaug                                                    19

<210> SEQ ID NO 143
<211> LENGTH: 19
<212> TYPE: RNA
<213> ORGANISM: Homo sapiens

<400> SEQUENCE: 143
cuuccagugu gaugauggu                                                    19

<210> SEQ ID NO 144
<211> LENGTH: 19
<212> TYPE: RNA
<213> ORGANISM: Homo sapiens
```

```
<400> SEQUENCE: 144
agucuuccag ugugaugau                                          19

<210> SEQ ID NO 145
<211> LENGTH: 19
<212> TYPE: RNA
<213> ORGANISM: Homo sapiens

<400> SEQUENCE: 145
ccacuggagu cuuccagug                                          19

<210> SEQ ID NO 146
<211> LENGTH: 19
<212> TYPE: RNA
<213> ORGANISM: Homo sapiens

<400> SEQUENCE: 146
cacuggaguc uuccagugu                                          19

<210> SEQ ID NO 147
<211> LENGTH: 19
<212> TYPE: RNA
<213> ORGANISM: Homo sapiens

<400> SEQUENCE: 147
cuggagucuu ccaguguga                                          19

<210> SEQ ID NO 148
<211> LENGTH: 19
<212> TYPE: RNA
<213> ORGANISM: Homo sapiens

<400> SEQUENCE: 148
uggagucuuc cagugugau                                          19

<210> SEQ ID NO 149
<211> LENGTH: 19
<212> TYPE: RNA
<213> ORGANISM: Homo sapiens

<400> SEQUENCE: 149
accuccguca ugugcugug                                          19

<210> SEQ ID NO 150
<211> LENGTH: 19
<212> TYPE: RNA
<213> ORGANISM: Homo sapiens

<400> SEQUENCE: 150
ccacuggagu cuuccagug                                          19

<210> SEQ ID NO 151
<211> LENGTH: 19
<212> TYPE: RNA
<213> ORGANISM: Homo sapiens

<400> SEQUENCE: 151
ccuccgucau gugcuguga                                          19

<210> SEQ ID NO 152
<211> LENGTH: 19
<212> TYPE: RNA
<213> ORGANISM: Homo sapiens
```

```
<400> SEQUENCE: 152
cuccgucaug ugcugugac                                           19

<210> SEQ ID NO 153
<211> LENGTH: 19
<212> TYPE: RNA
<213> ORGANISM: Homo sapiens

<400> SEQUENCE: 153
auguaguugu aguggaugg                                           19

<210> SEQ ID NO 154
<211> LENGTH: 19
<212> TYPE: RNA
<213> ORGANISM: Homo sapiens

<400> SEQUENCE: 154
uaguuguagu ggauggugg                                           19

<210> SEQ ID NO 155
<211> LENGTH: 19
<212> TYPE: RNA
<213> ORGANISM: Homo sapiens

<400> SEQUENCE: 155
ucugaagggu gaaauauuc                                           19

<210> SEQ ID NO 156
<211> LENGTH: 19
<212> TYPE: RNA
<213> ORGANISM: Homo sapiens

<400> SEQUENCE: 156
gcaaauuucc uuccacucg                                           19

<210> SEQ ID NO 157
<211> LENGTH: 19
<212> TYPE: RNA
<213> ORGANISM: Homo sapiens

<400> SEQUENCE: 157
ugaaggguga aauauucuc                                           19

<210> SEQ ID NO 158
<211> LENGTH: 19
<212> TYPE: RNA
<213> ORGANISM: Homo sapiens

<400> SEQUENCE: 158
ggaacuguua cacauguag                                           19

<210> SEQ ID NO 159
<211> LENGTH: 19
<212> TYPE: RNA
<213> ORGANISM: Homo sapiens

<400> SEQUENCE: 159
aacuguuaca cauguaguu                                           19

<210> SEQ ID NO 160
<211> LENGTH: 19
<212> TYPE: RNA
<213> ORGANISM: Homo sapiens
```

```
<400> SEQUENCE: 160
acuguuacac auguaguug                                        19

<210> SEQ ID NO 161
<211> LENGTH: 19
<212> TYPE: RNA
<213> ORGANISM: Homo sapiens

<400> SEQUENCE: 161
uacacaugua guuguagug                                        19

<210> SEQ ID NO 162
<211> LENGTH: 19
<212> TYPE: RNA
<213> ORGANISM: Homo sapiens

<400> SEQUENCE: 162
acacauguag uuguagugg                                        19

<210> SEQ ID NO 163
<211> LENGTH: 19
<212> TYPE: RNA
<213> ORGANISM: Homo sapiens

<400> SEQUENCE: 163
gucgaaaagu guuucuguc                                        19

<210> SEQ ID NO 164
<211> LENGTH: 19
<212> TYPE: RNA
<213> ORGANISM: Homo sapiens

<400> SEQUENCE: 164
gaagggugaa auauucucc                                        19

<210> SEQ ID NO 165
<211> LENGTH: 19
<212> TYPE: RNA
<213> ORGANISM: Homo sapiens

<400> SEQUENCE: 165
caugcaggaa cuguuacac                                        19

<210> SEQ ID NO 166
<211> LENGTH: 19
<212> TYPE: RNA
<213> ORGANISM: Homo sapiens

<400> SEQUENCE: 166
cuguuacaca uguaguugu                                        19

<210> SEQ ID NO 167
<211> LENGTH: 19
<212> TYPE: RNA
<213> ORGANISM: Homo sapiens

<400> SEQUENCE: 167
uuacacaugu aguuguagu                                        19

<210> SEQ ID NO 168
<211> LENGTH: 19
<212> TYPE: RNA
<213> ORGANISM: Homo sapiens
```

```
<400> SEQUENCE: 168
uguaguugua guggauggu                                             19

<210> SEQ ID NO 169
<211> LENGTH: 19
<212> TYPE: RNA
<213> ORGANISM: Homo sapiens

<400> SEQUENCE: 169
aguuguagug gaugguggu                                             19

<210> SEQ ID NO 170
<211> LENGTH: 19
<212> TYPE: RNA
<213> ORGANISM: Homo sapiens

<400> SEQUENCE: 170
guuguagugg augguggua                                             19

<210> SEQ ID NO 171
<211> LENGTH: 19
<212> TYPE: RNA
<213> ORGANISM: Homo sapiens

<400> SEQUENCE: 171
ugucgaaaag uguuucugu                                             19

<210> SEQ ID NO 172
<211> LENGTH: 19
<212> TYPE: RNA
<213> ORGANISM: Homo sapiens

<400> SEQUENCE: 172
cgcaaauuuc cuuccacuc                                             19

<210> SEQ ID NO 173
<211> LENGTH: 19
<212> TYPE: RNA
<213> ORGANISM: Homo sapiens

<400> SEQUENCE: 173
gaucugaagg gugaaauau                                             19

<210> SEQ ID NO 174
<211> LENGTH: 19
<212> TYPE: RNA
<213> ORGANISM: Homo sapiens

<400> SEQUENCE: 174
aucugaaggg ugaaauauu                                             19

<210> SEQ ID NO 175
<211> LENGTH: 19
<212> TYPE: RNA
<213> ORGANISM: Homo sapiens

<400> SEQUENCE: 175
cugaagggug aaauauucu                                             19

<210> SEQ ID NO 176
<211> LENGTH: 19
<212> TYPE: RNA
<213> ORGANISM: Homo sapiens
```

```
<400> SEQUENCE: 176
aagggugaaa uauucucca                                              19

<210> SEQ ID NO 177
<211> LENGTH: 19
<212> TYPE: RNA
<213> ORGANISM: Homo sapiens

<400> SEQUENCE: 177
caggaacugu uacacaugu                                              19

<210> SEQ ID NO 178
<211> LENGTH: 19
<212> TYPE: RNA
<213> ORGANISM: Homo sapiens

<400> SEQUENCE: 178
uguuacacau guaguugua                                              19

<210> SEQ ID NO 179
<211> LENGTH: 19
<212> TYPE: RNA
<213> ORGANISM: Homo sapiens

<400> SEQUENCE: 179
guuacacaug uaguuguag                                              19

<210> SEQ ID NO 180
<211> LENGTH: 19
<212> TYPE: RNA
<213> ORGANISM: Homo sapiens

<400> SEQUENCE: 180
cacauguagu uguagugga                                              19

<210> SEQ ID NO 181
<211> LENGTH: 19
<212> TYPE: RNA
<213> ORGANISM: Homo sapiens

<400> SEQUENCE: 181
acauguaguu guaguggau                                              19

<210> SEQ ID NO 182
<211> LENGTH: 19
<212> TYPE: RNA
<213> ORGANISM: Homo sapiens

<400> SEQUENCE: 182
cauguaguug uaguggaug                                              19

<210> SEQ ID NO 183
<211> LENGTH: 19
<212> TYPE: RNA
<213> ORGANISM: Homo sapiens

<400> SEQUENCE: 183
guaguuguag uggauggug                                              19

<210> SEQ ID NO 184
<211> LENGTH: 19
<212> TYPE: RNA
<213> ORGANISM: Homo sapiens
```

```
<400> SEQUENCE: 184
augcaggaac uguuacaca                                              19

<210> SEQ ID NO 185
<211> LENGTH: 19
<212> TYPE: RNA
<213> ORGANISM: Homo sapiens

<400> SEQUENCE: 185
gcaggaacug uuacacaug                                              19

<210> SEQ ID NO 186
<211> LENGTH: 19
<212> TYPE: RNA
<213> ORGANISM: Homo sapiens

<400> SEQUENCE: 186
aggaacuguu acacaugua                                              19

<210> SEQ ID NO 187
<211> LENGTH: 19
<212> TYPE: RNA
<213> ORGANISM: Homo sapiens

<400> SEQUENCE: 187
gaacuguuac acauguagu                                              19

<210> SEQ ID NO 188
<211> LENGTH: 19
<212> TYPE: RNA
<213> ORGANISM: Homo sapiens

<400> SEQUENCE: 188 aauuccuuc cacucggau                                               19

<210> SEQ ID NO 189
<211> LENGTH: 19
<212> TYPE: RNA
<213> ORGANISM: Homo sapiens

<400> SEQUENCE: 189
cuucaggugg cuggaguga                                              19

<210> SEQ ID NO 190
<211> LENGTH: 19
<212> TYPE: RNA
<213> ORGANISM: Homo sapiens

<400> SEQUENCE: 190
uucagguggc uggagugag                                              19

<210> SEQ ID NO 191
<211> LENGTH: 21
<212> TYPE: RNA
<213> ORGANISM: Homo sapiens

<400> SEQUENCE: 191
ggaagagaau cuccgcaaga a                                           21

<210> SEQ ID NO 192
<211> LENGTH: 21
<212> TYPE: RNA
<213> ORGANISM: Homo sapiens
```

-continued

```
<400> SEQUENCE: 192
guaccaccau ccacuacaac u                                              21

<210> SEQ ID NO 193
<211> LENGTH: 21
<212> TYPE: RNA
<213> ORGANISM: Homo sapiens

<400> SEQUENCE: 193
ggacgauauu gaacaauggu u                                              21

<210> SEQ ID NO 194
<211> LENGTH: 21
<212> TYPE: RNA
<213> ORGANISM: Homo sapiens

<400> SEQUENCE: 194
ccagccaccu gaaguccaaa a                                              21

<210> SEQ ID NO 195
<211> LENGTH: 21
<212> TYPE: RNA
<213> ORGANISM: Homo sapiens

<400> SEQUENCE: 195
gagaauauuu cacccuucag a                                              21

<210> SEQ ID NO 196
<211> LENGTH: 21
<212> TYPE: RNA
<213> ORGANISM: Homo sapiens

<400> SEQUENCE: 196
agaaaccacu ggauggagaa u                                              21

<210> SEQ ID NO 197
<211> LENGTH: 21
<212> TYPE: RNA
<213> ORGANISM: Homo sapiens

<400> SEQUENCE: 197
cuacugggac ggaacagcuu u                                              21

<210> SEQ ID NO 198
<211> LENGTH: 21
<212> TYPE: RNA
<213> ORGANISM: Homo sapiens

<400> SEQUENCE: 198
agacuccagu gguaaucuac u                                              21

<210> SEQ ID NO 199
<211> LENGTH: 21
<212> TYPE: RNA
<213> ORGANISM: Homo sapiens

<400> SEQUENCE: 199
cuggaagacu ccaguggaaa u                                              21

<210> SEQ ID NO 200
<211> LENGTH: 21
<212> TYPE: RNA
<213> ORGANISM: Homo sapiens
```

```
<400> SEQUENCE: 200
gaaacuacuu ccugaaaaca a                                              21

<210> SEQ ID NO 201
<211> LENGTH: 21
<212> TYPE: RNA
<213> ORGANISM: Homo sapiens

<400> SEQUENCE: 201
ggaaacuacu uccugaaaac a                                              21

<210> SEQ ID NO 202
<211> LENGTH: 21
<212> TYPE: RNA
<213> ORGANISM: Homo sapiens

<400> SEQUENCE: 202
aaacacuuuu cgacauagug u                                              21

<210> SEQ ID NO 203
<211> LENGTH: 21
<212> TYPE: RNA
<213> ORGANISM: Homo sapiens

<400> SEQUENCE: 203
ggaguauuug gaugacagaa a                                              21

<210> SEQ ID NO 204
<211> LENGTH: 21
<212> TYPE: RNA
<213> ORGANISM: Homo sapiens

<400> SEQUENCE: 204
ucagaccuau ggaaacuacu u                                              21

<210> SEQ ID NO 205
<211> LENGTH: 21
<212> TYPE: RNA
<213> ORGANISM: Homo sapiens

<400> SEQUENCE: 205
ccauggccau cuacaagcag u                                              21

<210> SEQ ID NO 206
<211> LENGTH: 21
<212> TYPE: RNA
<213> ORGANISM: Homo sapiens

<400> SEQUENCE: 206
ccaagucugu gacuugcacg u                                              21

<210> SEQ ID NO 207
<211> LENGTH: 21
<212> TYPE: RNA
<213> ORGANISM: Homo sapiens

<400> SEQUENCE: 207
ggacagccaa gucugugacu u                                              21

<210> SEQ ID NO 208
<211> LENGTH: 21
<212> TYPE: RNA
<213> ORGANISM: Homo sapiens
```

```
<400> SEQUENCE: 208
cccuccuucu cccuuuuuau a                                              21

<210> SEQ ID NO 209
<211> LENGTH: 21
<212> TYPE: RNA
<213> ORGANISM: Homo sapiens

<400> SEQUENCE: 209
ccauccacua caacuacaug u                                              21

<210> SEQ ID NO 210
<211> LENGTH: 21
<212> TYPE: RNA
<213> ORGANISM: Homo sapiens

<400> SEQUENCE: 210
ccaccaucca cuacaacuac a                                              21

<210> SEQ ID NO 211
<211> LENGTH: 21
<212> TYPE: RNA
<213> ORGANISM: Homo sapiens

<400> SEQUENCE: 211
gagaauauuu cacccuucag a                                              21

<210> SEQ ID NO 212
<211> LENGTH: 21
<212> TYPE: RNA
<213> ORGANISM: Homo sapiens

<400> SEQUENCE: 212
ggagaauauu ucacccuuca g                                              21

<210> SEQ ID NO 213
<211> LENGTH: 21
<212> TYPE: RNA
<213> ORGANISM: Homo sapiens

<400> SEQUENCE: 213
cuacaugugu aacaguuccu g                                              21

<210> SEQ ID NO 214
<211> LENGTH: 21
<212> TYPE: RNA
<213> ORGANISM: Homo sapiens

<400> SEQUENCE: 214
acaacuacau guguaacagu u                                              21

<210> SEQ ID NO 215
<211> LENGTH: 21
<212> TYPE: RNA
<213> ORGANISM: Homo sapiens

<400> SEQUENCE: 215
ccacuacaac uacaugugua a                                              21

<210> SEQ ID NO 216
<211> LENGTH: 21
<212> TYPE: RNA
<213> ORGANISM: Homo sapiens
```

-continued

```
<400> SEQUENCE: 216
caccauccac uacaacuaca u                                              21

<210> SEQ ID NO 217
<211> LENGTH: 21
<212> TYPE: RNA
<213> ORGANISM: Homo sapiens

<400> SEQUENCE: 217
gaauauuuca cccuucagau c                                              21

<210> SEQ ID NO 218
<211> LENGTH: 21
<212> TYPE: RNA
<213> ORGANISM: Homo sapiens

<400> SEQUENCE: 218
agaauauuuc acccuucaga u                                              21

<210> SEQ ID NO 219
<211> LENGTH: 21
<212> TYPE: RNA
<213> ORGANISM: Homo sapiens

<400> SEQUENCE: 219
uaccaccauc cacuacaacu a                                              21

<210> SEQ ID NO 220
<211> LENGTH: 21
<212> TYPE: RNA
<213> ORGANISM: Homo sapiens

<400> SEQUENCE: 220
gauggagaau auuucacccu u                                              21

<210> SEQ ID NO 221
<211> LENGTH: 21
<212> TYPE: RNA
<213> ORGANISM: Homo sapiens

<400> SEQUENCE: 221
ccgaguggaa ggaaauuugc g                                              21

<210> SEQ ID NO 222
<211> LENGTH: 21
<212> TYPE: RNA
<213> ORGANISM: Homo sapiens

<400> SEQUENCE: 222
aacuacaugu guaacaguuc c                                              21

<210> SEQ ID NO 223
<211> LENGTH: 21
<212> TYPE: RNA
<213> ORGANISM: Homo sapiens

<400> SEQUENCE: 223
caacuacaug uguaacaguu c                                              21

<210> SEQ ID NO 224
<211> LENGTH: 21
<212> TYPE: RNA
<213> ORGANISM: Homo sapiens
```

```
<400> SEQUENCE: 224
acuacaacua cauguguaac a                                              21

<210> SEQ ID NO 225
<211> LENGTH: 21
<212> TYPE: RNA
<213> ORGANISM: Homo sapiens

<400> SEQUENCE: 225
cacuacaacu acauguguaa c                                              21

<210> SEQ ID NO 226
<211> LENGTH: 21
<212> TYPE: RNA
<213> ORGANISM: Homo sapiens

<400> SEQUENCE: 226
uccacuacaa cuacaugugu a                                              21

<210> SEQ ID NO 227
<211> LENGTH: 21
<212> TYPE: RNA
<213> ORGANISM: Homo sapiens

<400> SEQUENCE: 227
cauccacuac aacuacaugu g                                              21

<210> SEQ ID NO 228
<211> LENGTH: 21
<212> TYPE: RNA
<213> ORGANISM: Homo sapiens

<400> SEQUENCE: 228
accauccacu acaacuacau g                                              21

<210> SEQ ID NO 229
<211> LENGTH: 21
<212> TYPE: RNA
<213> ORGANISM: Homo sapiens

<400> SEQUENCE: 229
uggagaauau uucacccuuc a                                              21

<210> SEQ ID NO 230
<211> LENGTH: 21
<212> TYPE: RNA
<213> ORGANISM: Homo sapiens

<400> SEQUENCE: 230
auguguaaca guuccugcau g                                              21

<210> SEQ ID NO 231
<211> LENGTH: 21
<212> TYPE: RNA
<213> ORGANISM: Homo sapiens

<400> SEQUENCE: 231
cauguguaac aguuccugca u                                              21

<210> SEQ ID NO 232
<211> LENGTH: 21
<212> TYPE: RNA
<213> ORGANISM: Homo sapiens
```

-continued

```
<400> SEQUENCE: 232
uacaacuaca uguguaacag u                                              21

<210> SEQ ID NO 233
<211> LENGTH: 21
<212> TYPE: RNA
<213> ORGANISM: Homo sapiens

<400> SEQUENCE: 233
cuacaacuac auguguaaca g                                              21

<210> SEQ ID NO 234
<211> LENGTH: 21
<212> TYPE: RNA
<213> ORGANISM: Homo sapiens

<400> SEQUENCE: 234
auccacuaca acuacaugug u                                              21

<210> SEQ ID NO 235
<211> LENGTH: 21
<212> TYPE: RNA
<213> ORGANISM: Homo sapiens

<400> SEQUENCE: 235
accaccaucc acuacaacua c                                              21

<210> SEQ ID NO 236
<211> LENGTH: 21
<212> TYPE: RNA
<213> ORGANISM: Homo sapiens

<400> SEQUENCE: 236
aauauuucac ccuucagauc c                                              21

<210> SEQ ID NO 237
<211> LENGTH: 21
<212> TYPE: RNA
<213> ORGANISM: Homo sapiens

<400> SEQUENCE: 237
acuacaugug uaacaguucc u                                              21

<210> SEQ ID NO 238
<211> LENGTH: 21
<212> TYPE: RNA
<213> ORGANISM: Homo sapiens

<400> SEQUENCE: 238
auggagaaua uuucacccuu c                                              21

<210> SEQ ID NO 239
<211> LENGTH: 21
<212> TYPE: RNA
<213> ORGANISM: Homo sapiens

<400> SEQUENCE: 239
uguguaacag uuccugcaug g                                              21

<210> SEQ ID NO 240
<211> LENGTH: 21
<212> TYPE: RNA
<213> ORGANISM: Homo sapiens
```

-continued

```
<400> SEQUENCE: 240
uccgagugga aggaaauuug c                                               21

<210> SEQ ID NO 241
<211> LENGTH: 21
<212> TYPE: RNA
<213> ORGANISM: Homo sapiens

<400> SEQUENCE: 241
auccgagugg aaggaaauuu g                                               21

<210> SEQ ID NO 242
<211> LENGTH: 21
<212> TYPE: RNA
<213> ORGANISM: Homo sapiens

<400> SEQUENCE: 242
ucacacugga agacuccagu g                                               21

<210> SEQ ID NO 243
<211> LENGTH: 21
<212> TYPE: RNA
<213> ORGANISM: Homo sapiens

<400> SEQUENCE: 243
aucacacugg aagacuccag u                                               21

<210> SEQ ID NO 244
<211> LENGTH: 21
<212> TYPE: RNA
<213> ORGANISM: Homo sapiens

<400> SEQUENCE: 244
cacacuggaa gacuccagug g                                               21

<210> SEQ ID NO 245
<211> LENGTH: 21
<212> TYPE: RNA
<213> ORGANISM: Homo sapiens

<400> SEQUENCE: 245
ucaucacacu ggaagacucc a                                               21

<210> SEQ ID NO 246
<211> LENGTH: 21
<212> TYPE: RNA
<213> ORGANISM: Homo sapiens

<400> SEQUENCE: 246
ccaucaucac acuggaagac u                                               21

<210> SEQ ID NO 247
<211> LENGTH: 21
<212> TYPE: RNA
<213> ORGANISM: Homo sapiens

<400> SEQUENCE: 247
caucacacug gaagacucca g                                               21

<210> SEQ ID NO 248
<211> LENGTH: 21
<212> TYPE: RNA
<213> ORGANISM: Homo sapiens
```

-continued

```
<400> SEQUENCE: 248
caucaucaca cuggaagacu c                                              21

<210> SEQ ID NO 249
<211> LENGTH: 21
<212> TYPE: RNA
<213> ORGANISM: Homo sapiens

<400> SEQUENCE: 249
accaucauca cacuggaaga c                                              21

<210> SEQ ID NO 250
<211> LENGTH: 21
<212> TYPE: RNA
<213> ORGANISM: Homo sapiens

<400> SEQUENCE: 250
ucacacugga agacuccagu g                                              21

<210> SEQ ID NO 251
<211> LENGTH: 21
<212> TYPE: RNA
<213> ORGANISM: Homo sapiens

<400> SEQUENCE: 251
aucacacugg aagacuccag u                                              21

<210> SEQ ID NO 252
<211> LENGTH: 21
<212> TYPE: RNA
<213> ORGANISM: Homo sapiens

<400> SEQUENCE: 252
aucaucacac uggaagacuc c                                              21

<210> SEQ ID NO 253
<211> LENGTH: 21
<212> TYPE: RNA
<213> ORGANISM: Homo sapiens

<400> SEQUENCE: 253
cacacuggaa gacuccagug g                                              21

<210> SEQ ID NO 254
<211> LENGTH: 21
<212> TYPE: RNA
<213> ORGANISM: Homo sapiens

<400> SEQUENCE: 254
uucuugcgga gauucucuuc c                                              21

<210> SEQ ID NO 255
<211> LENGTH: 21
<212> TYPE: RNA
<213> ORGANISM: Homo sapiens

<400> SEQUENCE: 255
aguuguagug gaugguggua c                                              21

<210> SEQ ID NO 256
<211> LENGTH: 21
<212> TYPE: RNA
<213> ORGANISM: Homo sapiens
```

```
<400> SEQUENCE: 256
aaccauuguu caauaucguc c                                              21

<210> SEQ ID NO 257
<211> LENGTH: 21
<212> TYPE: RNA
<213> ORGANISM: Homo sapiens

<400> SEQUENCE: 257
uuuuggacuu cagguggcug g                                              21

<210> SEQ ID NO 258
<211> LENGTH: 21
<212> TYPE: RNA
<213> ORGANISM: Homo sapiens

<400> SEQUENCE: 258
ucugaagggu gaaauauucu c                                              21

<210> SEQ ID NO 259
<211> LENGTH: 21
<212> TYPE: RNA
<213> ORGANISM: Homo sapiens

<400> SEQUENCE: 259
auucuccauc cagugguuuc u                                              21

<210> SEQ ID NO 260
<211> LENGTH: 21
<212> TYPE: RNA
<213> ORGANISM: Homo sapiens

<400> SEQUENCE: 260
aaagcuguuc cgucccagua g                                              21

<210> SEQ ID NO 261
<211> LENGTH: 21
<212> TYPE: RNA
<213> ORGANISM: Homo sapiens

<400> SEQUENCE: 261
aguagauuac cacuggaguc u                                              21

<210> SEQ ID NO 262
<211> LENGTH: 21
<212> TYPE: RNA
<213> ORGANISM: Homo sapiens

<400> SEQUENCE: 262
auuaccacug gagucuucca g                                              21

<210> SEQ ID NO 263
<211> LENGTH: 21
<212> TYPE: RNA
<213> ORGANISM: Homo sapiens

<400> SEQUENCE: 263
uuguuuucag gaaguaguuu c                                              21

<210> SEQ ID NO 264
<211> LENGTH: 21
<212> TYPE: RNA
<213> ORGANISM: Homo sapiens
```

-continued

```
<400> SEQUENCE: 264
uguuuucagg aaguaguuuc c                                              21

<210> SEQ ID NO 265
<211> LENGTH: 21
<212> TYPE: RNA
<213> ORGANISM: Homo sapiens

<400> SEQUENCE: 265
acacuauguc gaaaaguguu u                                              21

<210> SEQ ID NO 266
<211> LENGTH: 21
<212> TYPE: RNA
<213> ORGANISM: Homo sapiens

<400> SEQUENCE: 266
uuucugucau ccaaauacuc c                                              21

<210> SEQ ID NO 267
<211> LENGTH: 21
<212> TYPE: RNA
<213> ORGANISM: Homo sapiens

<400> SEQUENCE: 267
aaguaguuuc cauaggucug a                                              21

<210> SEQ ID NO 268
<211> LENGTH: 21
<212> TYPE: RNA
<213> ORGANISM: Homo sapiens

<400> SEQUENCE: 268
acugcuugua gauggccaug g                                              21

<210> SEQ ID NO 269
<211> LENGTH: 21
<212> TYPE: RNA
<213> ORGANISM: Homo sapiens

<400> SEQUENCE: 269
acgugcaagu cacagacuug g                                              21

<210> SEQ ID NO 270
<211> LENGTH: 21
<212> TYPE: RNA
<213> ORGANISM: Homo sapiens

<400> SEQUENCE: 270
aagucacaga cuuggcuguc c                                              21

<210> SEQ ID NO 271
<211> LENGTH: 21
<212> TYPE: RNA
<213> ORGANISM: Homo sapiens

<400> SEQUENCE: 271
uauaaaaagg gagaaggagg g                                              21

<210> SEQ ID NO 272
<211> LENGTH: 21
<212> TYPE: RNA
<213> ORGANISM: Homo sapiens
```

-continued

```
<400> SEQUENCE: 272
acauguaguu guaguggaug g                                              21

<210> SEQ ID NO 273
<211> LENGTH: 21
<212> TYPE: RNA
<213> ORGANISM: Homo sapiens

<400> SEQUENCE: 273
uguaguugua guggauggug g                                              21

<210> SEQ ID NO 274
<211> LENGTH: 21
<212> TYPE: RNA
<213> ORGANISM: Homo sapiens

<400> SEQUENCE: 274
ucugaagggu gaaauauucu c                                              21

<210> SEQ ID NO 275
<211> LENGTH: 21
<212> TYPE: RNA
<213> ORGANISM: Homo sapiens

<400> SEQUENCE: 275
cugaagggug aaauauucuc c                                              21

<210> SEQ ID NO 276
<211> LENGTH: 21
<212> TYPE: RNA
<213> ORGANISM: Homo sapiens

<400> SEQUENCE: 276
caggaacugu uacacaugua g                                              21

<210> SEQ ID NO 277
<211> LENGTH: 21
<212> TYPE: RNA
<213> ORGANISM: Homo sapiens

<400> SEQUENCE: 277
aacuguuaca cauguaguug u                                              21

<210> SEQ ID NO 278
<211> LENGTH: 21
<212> TYPE: RNA
<213> ORGANISM: Homo sapiens

<400> SEQUENCE: 278
uuacacaugu aguuguagug g                                              21

<210> SEQ ID NO 279
<211> LENGTH: 21
<212> TYPE: RNA
<213> ORGANISM: Homo sapiens

<400> SEQUENCE: 279
auguaguugu aguggauggu g                                              21

<210> SEQ ID NO 280
<211> LENGTH: 21
<212> TYPE: RNA
<213> ORGANISM: Homo sapiens
```

```
<400> SEQUENCE: 280
gaucugaagg gugaaauauu c                                          21

<210> SEQ ID NO 281
<211> LENGTH: 21
<212> TYPE: RNA
<213> ORGANISM: Homo sapiens

<400> SEQUENCE: 281
aucugaaggg ugaaauauuc u                                          21

<210> SEQ ID NO 282
<211> LENGTH: 21
<212> TYPE: RNA
<213> ORGANISM: Homo sapiens

<400> SEQUENCE: 282
uaguuguagu ggaugguggu a                                          21

<210> SEQ ID NO 283
<211> LENGTH: 21
<212> TYPE: RNA
<213> ORGANISM: Homo sapiens

<400> SEQUENCE: 283
aagggugaaa uauucuccau c                                          21

<210> SEQ ID NO 284
<211> LENGTH: 21
<212> TYPE: RNA
<213> ORGANISM: Homo sapiens

<400> SEQUENCE: 284
cgcaaauuuc cuuccacucg g                                          21

<210> SEQ ID NO 285
<211> LENGTH: 21
<212> TYPE: RNA
<213> ORGANISM: Homo sapiens

<400> SEQUENCE: 285
ggaacuguua cacauguagu u                                          21

<210> SEQ ID NO 286
<211> LENGTH: 21
<212> TYPE: RNA
<213> ORGANISM: Homo sapiens

<400> SEQUENCE: 286
gaacuguuac acauguaguu g                                          21

<210> SEQ ID NO 287
<211> LENGTH: 21
<212> TYPE: RNA
<213> ORGANISM: Homo sapiens

<400> SEQUENCE: 287
uguuacacau guaguuguag u                                          21

<210> SEQ ID NO 288
<211> LENGTH: 21
<212> TYPE: RNA
<213> ORGANISM: Homo sapiens
```

```
<400> SEQUENCE: 288
guuacacaug uaguuguagu g                                          21

<210> SEQ ID NO 289
<211> LENGTH: 21
<212> TYPE: RNA
<213> ORGANISM: Homo sapiens

<400> SEQUENCE: 289
uacacaugua guuguagugg a                                          21

<210> SEQ ID NO 290
<211> LENGTH: 21
<212> TYPE: RNA
<213> ORGANISM: Homo sapiens

<400> SEQUENCE: 290
cacauguagu uguaguggau g                                          21

<210> SEQ ID NO 291
<211> LENGTH: 21
<212> TYPE: RNA
<213> ORGANISM: Homo sapiens

<400> SEQUENCE: 291
cauguaguug uaguggaugg u                                          21

<210> SEQ ID NO 292
<211> LENGTH: 21
<212> TYPE: RNA
<213> ORGANISM: Homo sapiens

<400> SEQUENCE: 292
ugaaggguga aauauucucc a                                          21

<210> SEQ ID NO 293
<211> LENGTH: 21
<212> TYPE: RNA
<213> ORGANISM: Homo sapiens

<400> SEQUENCE: 293
caugcaggaa cuguuacaca u                                          21

<210> SEQ ID NO 294
<211> LENGTH: 21
<212> TYPE: RNA
<213> ORGANISM: Homo sapiens

<400> SEQUENCE: 294
augcaggaac uguuacacau g                                          21

<210> SEQ ID NO 295
<211> LENGTH: 21
<212> TYPE: RNA
<213> ORGANISM: Homo sapiens

<400> SEQUENCE: 295
acuguuacac auguaguugu a                                          21

<210> SEQ ID NO 296
<211> LENGTH: 21
<212> TYPE: RNA
<213> ORGANISM: Homo sapiens
```

```
<400> SEQUENCE: 296 cguuacaca uguaguugua g                                        21

<210> SEQ ID NO 297
<211> LENGTH: 21
<212> TYPE: RNA
<213> ORGANISM: Homo sapiens

<400> SEQUENCE: 297
acacauguag uuguagugga u                                       21

<210> SEQ ID NO 298
<211> LENGTH: 21
<212> TYPE: RNA
<213> ORGANISM: Homo sapiens

<400> SEQUENCE: 298
guaguuguag uggauggugg u                                       21

<210> SEQ ID NO 299
<211> LENGTH: 21
<212> TYPE: RNA
<213> ORGANISM: Homo sapiens

<400> SEQUENCE: 299
ggaucugaag ggugaaauau u                                       21

<210> SEQ ID NO 300
<211> LENGTH: 21
<212> TYPE: RNA
<213> ORGANISM: Homo sapiens

<400> SEQUENCE: 300
aggaacuguu acacauguag u                                       21

<210> SEQ ID NO 301
<211> LENGTH: 21
<212> TYPE: RNA
<213> ORGANISM: Homo sapiens

<400> SEQUENCE: 301
gaagggugaa auauucucca u                                       21

<210> SEQ ID NO 302
<211> LENGTH: 21
<212> TYPE: RNA
<213> ORGANISM: Homo sapiens

<400> SEQUENCE: 302
ccaugcagga acuguuacac a                                       21

<210> SEQ ID NO 303
<211> LENGTH: 21
<212> TYPE: RNA
<213> ORGANISM: Homo sapiens

<400> SEQUENCE: 303
gcaaauuucc uuccacucgg a                                       21

<210> SEQ ID NO 304
<211> LENGTH: 21
<212> TYPE: RNA
<213> ORGANISM: Homo sapiens
```

<400> SEQUENCE: 304
caaauucccu uccacucgga u                                                  21

<210> SEQ ID NO 305
<211> LENGTH: 21
<212> TYPE: RNA
<213> ORGANISM: Homo sapiens

<400> SEQUENCE: 305
cacuggaguc uuccagugug a                                                  21

<210> SEQ ID NO 306
<211> LENGTH: 21
<212> TYPE: RNA
<213> ORGANISM: Homo sapiens

<400> SEQUENCE: 306
acuggagucu uccaguguga u                                                  21

<210> SEQ ID NO 307
<211> LENGTH: 21
<212> TYPE: RNA
<213> ORGANISM: Homo sapiens

<400> SEQUENCE: 307
ccacuggagu cuuccagugu g                                                  21

<210> SEQ ID NO 308
<211> LENGTH: 21
<212> TYPE: RNA
<213> ORGANISM: Homo sapiens

<400> SEQUENCE: 308
uggagucuuc cagugugaug a                                                  21

<210> SEQ ID NO 309
<211> LENGTH: 21
<212> TYPE: RNA
<213> ORGANISM: Homo sapiens

<400> SEQUENCE: 309
agucuuccag ugugaugaug g                                                  21

<210> SEQ ID NO 310
<211> LENGTH: 21
<212> TYPE: RNA
<213> ORGANISM: Homo sapiens

<400> SEQUENCE: 310
cuggagucuu ccagugugau g                                                  21

<210> SEQ ID NO 311
<211> LENGTH: 21
<212> TYPE: RNA
<213> ORGANISM: Homo sapiens

<400> SEQUENCE: 311
gagucuucca gugugaugau g                                                  21

<210> SEQ ID NO 312
<211> LENGTH: 21
<212> TYPE: RNA
<213> ORGANISM: Homo sapiens -continued

```
<400> SEQUENCE: 312
gucuuccagu gugaugaugg u                                              21

<210> SEQ ID NO 313
<211> LENGTH: 21
<212> TYPE: RNA
<213> ORGANISM: Homo sapiens

<400> SEQUENCE: 313
cacuggaguc uuccagugug a                                              21

<210> SEQ ID NO 314
<211> LENGTH: 21
<212> TYPE: RNA
<213> ORGANISM: Homo sapiens

<400> SEQUENCE: 314
acuggagucu uccaguguga u                                              21

<210> SEQ ID NO 315
<211> LENGTH: 21
<212> TYPE: RNA
<213> ORGANISM: Homo sapiens

<400> SEQUENCE: 315
ggagucuucc agugugauga u                                              21

<210> SEQ ID NO 316
<211> LENGTH: 21
<212> TYPE: RNA
<213> ORGANISM: Homo sapiens

<400> SEQUENCE: 316
ccacuggagu cuuccagugu g                                              21

<210> SEQ ID NO 317
<211> LENGTH: 19
<212> TYPE: RNA
<213> ORGANISM: artificial
<220> FEATURE:
<223> OTHER INFORMATION: Chemically synthesized

<400> SEQUENCE: 317
gugccaaccu gaugcagcu                                                 19

<210> SEQ ID NO 318
<211> LENGTH: 19
<212> TYPE: RNA
<213> ORGANISM: Artificial Sequence
<220> FEATURE:
<223> OTHER INFORMATION: Chemically synthesized

<400> SEQUENCE: 318
agcugcauca gguuggcac                                                 19

<210> SEQ ID NO 319
<211> LENGTH: 23
<212> TYPE: RNA
<213> ORGANISM: artificial
<220> FEATURE:
<223> OTHER INFORMATION: Chemically synthesized

<400> SEQUENCE: 319
ggagaauauu ucacccuuca gau                                            23
```

```
<210> SEQ ID NO 320
<211> LENGTH: 23
<212> TYPE: RNA
<213> ORGANISM: artificial
<220> FEATURE:
<223> OTHER INFORMATION: Chemically synthesized

<400> SEQUENCE: 320
uggagaauau uucacccuuc aga                                             23

<210> SEQ ID NO 321
<211> LENGTH: 23
<212> TYPE: RNA
<213> ORGANISM: artificial
<220> FEATURE:
<223> OTHER INFORMATION: Chemically synthesized

<400> SEQUENCE: 321
auggagaaua uuucacccuu cag                                             23

<210> SEQ ID NO 322
<211> LENGTH: 23
<212> TYPE: RNA
<213> ORGANISM: artificial
<220> FEATURE:
<223> OTHER INFORMATION: Chemically synthesized

<400> SEQUENCE: 322
gauggagaau auuucacccu uca                                             23

<210> SEQ ID NO 323
<211> LENGTH: 23
<212> TYPE: RNA
<213> ORGANISM: artificial
<220> FEATURE:
<223> OTHER INFORMATION: Chemically synthesized

<400> SEQUENCE: 323
gagaauauuu cacccuucag auc                                             23

<210> SEQ ID NO 324
<211> LENGTH: 23
<212> TYPE: RNA
<213> ORGANISM: artificial
<220> FEATURE:
<223> OTHER INFORMATION: Chemically synthesized

<400> SEQUENCE: 324
aguguggugg ugcccuauga gcc                                             23

<210> SEQ ID NO 325
<211> LENGTH: 23
<212> TYPE: RNA
<213> ORGANISM: artificial
<220> FEATURE:
<223> OTHER INFORMATION: Chemically synthesized

<400> SEQUENCE: 325
uaguguggug gugcccuaug agc                                             23

<210> SEQ ID NO 326
<211> LENGTH: 23
<212> TYPE: RNA
<213> ORGANISM: artificial
<220> FEATURE:
<223> OTHER INFORMATION: Chemically synthesized
```

```
<400> SEQUENCE: 326
auaguguggu ggugcccuau gag                                              23

<210> SEQ ID NO 327
<211> LENGTH: 23
<212> TYPE: RNA
<213> ORGANISM: artificial
<220> FEATURE:
<223> OTHER INFORMATION: Chemically synthesized

<400> SEQUENCE: 327
cauagugugg uggugcccua uga                                              23

<210> SEQ ID NO 328
<211> LENGTH: 23
<212> TYPE: RNA
<213> ORGANISM: artificial
<220> FEATURE:
<223> OTHER INFORMATION: Chemically synthesized

<400> SEQUENCE: 328 guguggggu gcccuaugag ccg                                               23

<210> SEQ ID NO 329
<211> LENGTH: 23
<212> TYPE: RNA
<213> ORGANISM: artificial
<220> FEATURE:
<223> OTHER INFORMATION: Chemically synthesized

<400> SEQUENCE: 329
ugacagaaac acuuucgac aua                                               23

<210> SEQ ID NO 330
<211> LENGTH: 23
<212> TYPE: RNA
<213> ORGANISM: artificial
<220> FEATURE:
<223> OTHER INFORMATION: Chemically synthesized

<400> SEQUENCE: 330
augacagaaa cacuuuucga cau                                              23

<210> SEQ ID NO 331
<211> LENGTH: 23
<212> TYPE: RNA
<213> ORGANISM: artificial
<220> FEATURE:
<223> OTHER INFORMATION: Chemically synthesized

<400> SEQUENCE: 331
gaugacagaa acacuuuucg aca                                              23

<210> SEQ ID NO 332
<211> LENGTH: 23
<212> TYPE: RNA
<213> ORGANISM: artificial
<220> FEATURE:
<223> OTHER INFORMATION: Chemically synthesized

<400> SEQUENCE: 332
ggaugacaga aacacuuuuc gac                                              23
```

```
<210> SEQ ID NO 333
<211> LENGTH: 23
<212> TYPE: RNA
<213> ORGANISM: artificial
<220> FEATURE:
<223> OTHER INFORMATION: Chemically synthesized

<400> SEQUENCE: 333
gacagaaaca cuuucgaca uag                                            23

<210> SEQ ID NO 334
<211> LENGTH: 23
<212> TYPE: RNA
<213> ORGANISM: artificial
<220> FEATURE:
<223> OTHER INFORMATION: Chemically synthesized

<400> SEQUENCE: 334
uccgagugga aggaaauuug cgu                                           23

<210> SEQ ID NO 335
<211> LENGTH: 23
<212> TYPE: RNA
<213> ORGANISM: artificial
<220> FEATURE:
<223> OTHER INFORMATION: Chemically synthesized

<400> SEQUENCE: 335
auccgagugg aaggaaauuu gcg                                           23

<210> SEQ ID NO 336
<211> LENGTH: 23
<212> TYPE: RNA
<213> ORGANISM: artificial
<220> FEATURE:
<223> OTHER INFORMATION: Chemically synthesized

<400> SEQUENCE: 336
uauccgagug gaaggaaauu ugc                                           23

<210> SEQ ID NO 337
<211> LENGTH: 23
<212> TYPE: RNA
<213> ORGANISM: artificial
<220> FEATURE:
<223> OTHER INFORMATION: Chemically synthesized

<400> SEQUENCE: 337
uuauccgagu ggaaggaaau uug                                           23

<210> SEQ ID NO 338
<211> LENGTH: 23
<212> TYPE: RNA
<213> ORGANISM: artificial
<220> FEATURE:
<223> OTHER INFORMATION: Chemically synthesized

<400> SEQUENCE: 338
ccgaguggaa ggaaauuugc gug                                           23

<210> SEQ ID NO 339
<211> LENGTH: 23
<212> TYPE: RNA
<213> ORGANISM: artificial
<220> FEATURE:
<223> OTHER INFORMATION: Chemically synthesized
```

```
-continued

<400> SEQUENCE: 339
aucaucacac uggaagacuc cag                                              23

<210> SEQ ID NO 340
<211> LENGTH: 23
<212> TYPE: RNA
<213> ORGANISM: artificial
<220> FEATURE:
<223> OTHER INFORMATION: Chemically synthesized

<400> SEQUENCE: 340
caucaucaca cuggaagacu cca                                              23

<210> SEQ ID NO 341
<211> LENGTH: 23
<212> TYPE: RNA
<213> ORGANISM: artificial
<220> FEATURE:
<223> OTHER INFORMATION: Chemically synthesized

<400> SEQUENCE: 341
ccaucaucac acuggaagac ucc                                              23

<210> SEQ ID NO 342
<211> LENGTH: 23
<212> TYPE: RNA
<213> ORGANISM: artificial
<220> FEATURE:
<223> OTHER INFORMATION: Chemically synthesized

<400> SEQUENCE: 342
accaucauca cacuggaaga cuc                                              23

<210> SEQ ID NO 343
<211> LENGTH: 23
<212> TYPE: RNA
<213> ORGANISM: artificial
<220> FEATURE:
<223> OTHER INFORMATION: Chemically synthesized

<400> SEQUENCE: 343
ucaucacacu ggaagacucc agu                                              23

<210> SEQ ID NO 344
<211> LENGTH: 23
<212> TYPE: RNA
<213> ORGANISM: artificial
<220> FEATURE:
<223> OTHER INFORMATION: Chemically synthesized

<400> SEQUENCE: 344
ucccaagcaa uggaugauuu gau                                              23

<210> SEQ ID NO 345
<211> LENGTH: 23
<212> TYPE: RNA
<213> ORGANISM: artificial
<220> FEATURE:
<223> OTHER INFORMATION: Chemically synthesized

<400> SEQUENCE: 345
gucccaagca auggaugauu uga                                              23
```

```
<210> SEQ ID NO 346
<211> LENGTH: 23
<212> TYPE: RNA
<213> ORGANISM: artificial
<220> FEATURE:
<223> OTHER INFORMATION: Chemically synthesized

<400> SEQUENCE: 346
cgucccaagc aauggaugau uug                                          23

<210> SEQ ID NO 347
<211> LENGTH: 23
<212> TYPE: RNA
<213> ORGANISM: artificial
<220> FEATURE:
<223> OTHER INFORMATION: Chemically synthesized

<400> SEQUENCE: 347
ccgucccaag caauggauga uuu                                          23

<210> SEQ ID NO 348
<211> LENGTH: 23
<212> TYPE: RNA
<213> ORGANISM: artificial
<220> FEATURE:
<223> OTHER INFORMATION: Chemically synthesized

<400> SEQUENCE: 348
cccaagcaau ggaugauuug aug                                          23

<210> SEQ ID NO 349
<211> LENGTH: 23
<212> TYPE: RNA
<213> ORGANISM: artificial
<220> FEATURE:
<223> OTHER INFORMATION: Chemically synthesized

<400> SEQUENCE: 349
ucagaccuau ggaaacuacu ucc                                          23

<210> SEQ ID NO 350
<211> LENGTH: 23
<212> TYPE: RNA
<213> ORGANISM: artificial
<220> FEATURE:
<223> OTHER INFORMATION: Chemically synthesized

<400> SEQUENCE: 350
uucagaccua uggaaacuac uuc                                          23

<210> SEQ ID NO 351
<211> LENGTH: 23
<212> TYPE: RNA
<213> ORGANISM: artificial
<220> FEATURE:
<223> OTHER INFORMATION: Chemically synthesized

<400> SEQUENCE: 351
uuucagaccu auggaaacua cuu                                          23

<210> SEQ ID NO 352
<211> LENGTH: 23
<212> TYPE: RNA
<213> ORGANISM: artificial
<220> FEATURE:
<223> OTHER INFORMATION: Chemically synthesized
```

```
<400> SEQUENCE: 352
uuuucagacc uauggaaacu acu                                          23

<210> SEQ ID NO 353
<211> LENGTH: 23
<212> TYPE: RNA
<213> ORGANISM: artificial
<220> FEATURE:
<223> OTHER INFORMATION: Chemically synthesized

<400> SEQUENCE: 353
cagaccuaug gaaacuacuu ccu                                          23

<210> SEQ ID NO 354
<211> LENGTH: 23
<212> TYPE: RNA
<213> ORGANISM: artificial
<220> FEATURE:
<223> OTHER INFORMATION: Chemically synthesized

<400> SEQUENCE: 354
aucugaaggg ugaaauauuc ucc                                          23

<210> SEQ ID NO 355
<211> LENGTH: 23
<212> TYPE: RNA
<213> ORGANISM: artificial
<220> FEATURE:
<223> OTHER INFORMATION: Chemically synthesized

<400> SEQUENCE: 355
ucugaagggu gaaauauucu cca                                          23

<210> SEQ ID NO 356
<211> LENGTH: 23
<212> TYPE: RNA
<213> ORGANISM: artificial
<220> FEATURE:
<223> OTHER INFORMATION: Chemically synthesized

<400> SEQUENCE: 356
cugaagggug aaauauucuc cau                                          23

<210> SEQ ID NO 357
<211> LENGTH: 23
<212> TYPE: RNA
<213> ORGANISM: artificial
<220> FEATURE:
<223> OTHER INFORMATION: Chemically synthesized

<400> SEQUENCE: 357
ugaaggguga aauauucucc auc                                          23

<210> SEQ ID NO 358
<211> LENGTH: 23
<212> TYPE: RNA
<213> ORGANISM: artificial
<220> FEATURE:
<223> OTHER INFORMATION: Chemically synthesized

<400> SEQUENCE: 358
gaucugaagg gugaaauauu cuc                                          23
```

```
<210> SEQ ID NO 359
<211> LENGTH: 23
<212> TYPE: RNA
<213> ORGANISM: artificial
<220> FEATURE:
<223> OTHER INFORMATION: Chemically synthesized

<400> SEQUENCE: 359
ggcucauagg gcaccaccac acu                                             23

<210> SEQ ID NO 360
<211> LENGTH: 23
<212> TYPE: RNA
<213> ORGANISM: artificial
<220> FEATURE:
<223> OTHER INFORMATION: Chemically synthesized

<400> SEQUENCE: 360
gcucauaggg caccaccaca cua                                             23

<210> SEQ ID NO 361
<211> LENGTH: 23
<212> TYPE: RNA
<213> ORGANISM: artificial
<220> FEATURE:
<223> OTHER INFORMATION: Chemically synthesized

<400> SEQUENCE: 361
cucauagggc accaccacac uau                                             23

<210> SEQ ID NO 362
<211> LENGTH: 23
<212> TYPE: RNA
<213> ORGANISM: artificial
<220> FEATURE:
<223> OTHER INFORMATION: Chemically synthesized

<400> SEQUENCE: 362
ucauagggca ccaccacacu aug                                             23

<210> SEQ ID NO 363
<211> LENGTH: 23
<212> TYPE: RNA
<213> ORGANISM: artificial
<220> FEATURE:
<223> OTHER INFORMATION: Chemically synthesized

<400> SEQUENCE: 363
cggcucauag ggcaccacca cac                                             23

<210> SEQ ID NO 364
<211> LENGTH: 23
<212> TYPE: RNA
<213> ORGANISM: artificial
<220> FEATURE:
<223> OTHER INFORMATION: Chemically synthesized

<400> SEQUENCE: 364
uaugucgaaa aguguuucug uca                                             23

<210> SEQ ID NO 365
<211> LENGTH: 23
<212> TYPE: RNA
<213> ORGANISM: artificial
<220> FEATURE:
<223> OTHER INFORMATION: Chemically synthesized
```

```
<400> SEQUENCE: 365
augucgaaaa guguuucugu cau                                              23

<210> SEQ ID NO 366
<211> LENGTH: 23
<212> TYPE: RNA
<213> ORGANISM: artificial
<220> FEATURE:
<223> OTHER INFORMATION: Chemically synthesized

<400> SEQUENCE: 366
ugucgaaaag uguuucuguc auc                                              23

<210> SEQ ID NO 367
<211> LENGTH: 23
<212> TYPE: RNA
<213> ORGANISM: artificial
<220> FEATURE:
<223> OTHER INFORMATION: Chemically synthesized

<400> SEQUENCE: 367
gucgaaaagu guuucuguca ucc                                              23

<210> SEQ ID NO 368
<211> LENGTH: 23
<212> TYPE: RNA
<213> ORGANISM: artificial
<220> FEATURE:
<223> OTHER INFORMATION: Chemically synthesized

<400> SEQUENCE: 368
cuaugucgaa aaguguuucu guc                                              23

<210> SEQ ID NO 369
<211> LENGTH: 23
<212> TYPE: RNA
<213> ORGANISM: artificial
<220> FEATURE:
<223> OTHER INFORMATION: Chemically synthesized

<400> SEQUENCE: 369
acgcaaauuu ccuuccacuc gga                                              23

<210> SEQ ID NO 370
<211> LENGTH: 23
<212> TYPE: RNA
<213> ORGANISM: artificial
<220> FEATURE:
<223> OTHER INFORMATION: Chemically synthesized

<400> SEQUENCE: 370
cgcaaauuuc cuuccacucg gau                                              23

<210> SEQ ID NO 371
<211> LENGTH: 23
<212> TYPE: RNA
<213> ORGANISM: artificial
<220> FEATURE:
<223> OTHER INFORMATION: Chemically synthesized

<400> SEQUENCE: 371
gcaaauuucc uuccacucgg aua                                              23
```

```
<210> SEQ ID NO 372
<211> LENGTH: 23
<212> TYPE: RNA
<213> ORGANISM: artificial
<220> FEATURE:
<223> OTHER INFORMATION: Chemically synthesized

<400> SEQUENCE: 372
caaauuuccu uccacucgga uaa                                          23

<210> SEQ ID NO 373
<211> LENGTH: 23
<212> TYPE: RNA
<213> ORGANISM: artificial
<220> FEATURE:
<223> OTHER INFORMATION: Chemically synthesized

<400> SEQUENCE: 373
cacgcaaauu uccuuccacu cgg                                          23

<210> SEQ ID NO 374
<211> LENGTH: 23
<212> TYPE: RNA
<213> ORGANISM: artificial
<220> FEATURE:
<223> OTHER INFORMATION: Chemically synthesized

<400> SEQUENCE: 374
cuggagucuu ccagugugau gau                                          23

<210> SEQ ID NO 375
<211> LENGTH: 23
<212> TYPE: RNA
<213> ORGANISM: artificial
<220> FEATURE:
<223> OTHER INFORMATION: Chemically synthesized

<400> SEQUENCE: 375
uggagucuuc cagugugaug aug                                          23

<210> SEQ ID NO 376
<211> LENGTH: 23
<212> TYPE: RNA
<213> ORGANISM: artificial
<220> FEATURE:
<223> OTHER INFORMATION: Chemically synthesized

<400> SEQUENCE: 376
ggagucuucc agugugauga ugg                                          23

<210> SEQ ID NO 377
<211> LENGTH: 23
<212> TYPE: RNA
<213> ORGANISM: artificial
<220> FEATURE:
<223> OTHER INFORMATION: Chemically synthesized

<400> SEQUENCE: 377
gagucuucca gugugaugau ggu                                          23

<210> SEQ ID NO 378
<211> LENGTH: 23
<212> TYPE: RNA
<213> ORGANISM: artificial
<220> FEATURE:
<223> OTHER INFORMATION: Chemically synthesized
```

```
<400> SEQUENCE: 378
acuggagucu uccaguguga uga                                              23

<210> SEQ ID NO 379
<211> LENGTH: 23
<212> TYPE: RNA
<213> ORGANISM: artificial
<220> FEATURE:
<223> OTHER INFORMATION: Chemically synthesized

<400> SEQUENCE: 379
aucaaaucau ccauugcuug gga                                              23

<210> SEQ ID NO 380
<211> LENGTH: 23
<212> TYPE: RNA
<213> ORGANISM: artificial
<220> FEATURE:
<223> OTHER INFORMATION: Chemically synthesized

<400> SEQUENCE: 380
ucaaaucauc cauugcuugg gac                                              23

<210> SEQ ID NO 381
<211> LENGTH: 23
<212> TYPE: RNA
<213> ORGANISM: artificial
<220> FEATURE:
<223> OTHER INFORMATION: Chemically synthesized

<400> SEQUENCE: 381
caaaucaucc auugcuuggg acg                                              23

<210> SEQ ID NO 382
<211> LENGTH: 23
<212> TYPE: RNA
<213> ORGANISM: artificial
<220> FEATURE:
<223> OTHER INFORMATION: Chemically synthesized

<400> SEQUENCE: 382
aaaucaucca uugcuuggga cgg                                              23

<210> SEQ ID NO 383
<211> LENGTH: 23
<212> TYPE: RNA
<213> ORGANISM: artificial
<220> FEATURE:
<223> OTHER INFORMATION: Chemically synthesized

<400> SEQUENCE: 383
caucaaauca uccauugcuu ggg                                              23

<210> SEQ ID NO 384
<211> LENGTH: 23
<212> TYPE: RNA
<213> ORGANISM: artificial
<220> FEATURE:
<223> OTHER INFORMATION: Chemically synthesized

<400> SEQUENCE: 384
ggaaguaguu uccauagguc uga                                              23
```

```
<210> SEQ ID NO 385
<211> LENGTH: 23
<212> TYPE: RNA
<213> ORGANISM: artificial
<220> FEATURE:
<223> OTHER INFORMATION: Chemically synthesized

<400> SEQUENCE: 385
gaaguaguuu ccauaggucu gaa                                         23

<210> SEQ ID NO 386
<211> LENGTH: 23
<212> TYPE: RNA
<213> ORGANISM: artificial
<220> FEATURE:
<223> OTHER INFORMATION: Chemically synthesized

<400> SEQUENCE: 386
aaguaguuuc cauaggucug aaa                                         23

<210> SEQ ID NO 387
<211> LENGTH: 23
<212> TYPE: RNA
<213> ORGANISM: artificial
<220> FEATURE:
<223> OTHER INFORMATION: Chemically synthesized

<400> SEQUENCE: 387
aguaguuucc auaggucuga aaa                                         23

<210> SEQ ID NO 388
<211> LENGTH: 23
<212> TYPE: RNA
<213> ORGANISM: artificial
<220> FEATURE:
<223> OTHER INFORMATION: Chemically synthesized

<400> SEQUENCE: 388
aggaaguagu uuccauaggu cug                                         23
```